US012622589B2

(12) United States Patent
Anliker et al.

(10) Patent No.: US 12,622,589 B2
(45) Date of Patent: May 12, 2026

(54) METHOD AND EXAMINATION APPARATUS FOR MEDICAL EXAMINATION OF AN ANIMAL

(71) Applicant: Boehringer Ingelheim Vetmedica GmbH, Ingelheim am Rhein (DE)

(72) Inventors: Urs Anliker, Frauenkappelen (CH); Stefan Bauer, Bern (CH); Marco Burgener, Bern (CH); Christian Kauth, Villars-sur-Glâne (CH); Jeannine Fleth-James, Mainz (DE); Reinhard Forberger, Ingelheim am Rhein (DE); Silke Haag-Diergarten, Frankfurt am Main (DE); Dagmar Polotzek, Frankfurt am Main (DE); Daniela Katharina Rahmel, Ockenheim (DE); Tanja Margrit Zimmering, Heidesheim am Rhein (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 1014 days.

(21) Appl. No.: 17/070,973

(22) Filed: Oct. 15, 2020

(65) Prior Publication Data

US 2021/0113094 A1 Apr. 22, 2021

(30) Foreign Application Priority Data

Oct. 17, 2019 (EP) ..................................... 19203849
Oct. 17, 2019 (EP) ..................................... 19203861

(51) Int. Cl.
A61B 5/021 (2006.01)
A61B 5/00 (2006.01)
(Continued)

(52) U.S. Cl.
CPC .............. A61B 5/021 (2013.01); A61B 5/024 (2013.01); A61B 5/0295 (2013.01); A61B 5/352 (2021.01);
(Continued)

(58) Field of Classification Search
CPC ......... A61B 5/021; A61B 5/364; A61B 5/352; A61B 5/366; A61B 5/024; A61B 5/0295; A61B 5/7246; A61B 2503/40
See application file for complete search history.

(56) References Cited

U.S. PATENT DOCUMENTS 5,237,997 A 8/1993 Greubel et al.
6,331,162 B1 12/2001 Mitchell
(Continued)

FOREIGN PATENT DOCUMENTS

CN 1849998 A 10/2006
CN 101793975 A 8/2010
(Continued)

OTHER PUBLICATIONS

Guoqiang Yu et al., "Time-dependent blood flow and oxygenation in human skeletal muscles measured with noninvasive near-infrared diffuse optical spectroscopies", Journal of Biomedical Optics, Apr. 11, 2005, pp. 024027-1 to 024027-12, vol. 10, United States, XP055242986.
(Continued)

*Primary Examiner* — Alex M Valvis
*Assistant Examiner* — Jonathan M Haney
(74) *Attorney, Agent, or Firm* — Calderon Safran & Wright P.C.

(57) ABSTRACT

A method for medical examination, in particular determination of the blood pressure of an animal that preferably has a paw and is in particular an animal of the subfamily of the Felinae. In the method, a curve comprising information
(Continued)

about the arterial blood flow of the animal, in particular a photoplethysmogram, is recorded, and the curve is cut into several curve sections in such a way that each curve section corresponds to a heartbeat. According to another independent aspect, a sensor or a subset of sensors is selected from several sensors of the same kind to perform the examination.

20 Claims, 15 Drawing Sheets

(51) Int. Cl.

| | |
|---|---|
| *A61B 5/024* | (2006.01) |
| *A61B 5/0295* | (2006.01) |
| *A61B 5/352* | (2021.01) |
| *A61B 5/364* | (2021.01) |
| *A61B 5/366* | (2021.01) |

(52) U.S. Cl.
CPC .............. *A61B 5/364* (2021.01); *A61B 5/366* (2021.01); *A61B 5/7246* (2013.01); *A61B 2503/40* (2013.01)

(56) References Cited

U.S. PATENT DOCUMENTS

| | | | |
|---|---|---|---|
| 8,005,624 | B1 | 8/2011 | Starr |
| 8,723,717 | B2 | 5/2014 | Saito |
| 8,838,209 | B2 | 9/2014 | Mestha et al. |
| 8,870,782 | B2 | 10/2014 | Futatsuyama et al. |
| 9,011,346 | B2 | 4/2015 | Wiard et al. |
| 9,241,637 | B2 | 1/2016 | Wiard et al. |
| 9,645,232 | B2 | 5/2017 | Saito |
| 9,833,151 | B2 | 12/2017 | Wiard et al. |
| 10,349,847 | B2 | 7/2019 | Kwon et al. |
| 2002/0037095 | A1 | 3/2002 | Cheng |
| 2003/0144583 | A1 | 7/2003 | Cheng et al. |
| 2008/0183232 | A1 | 7/2008 | Voss et al. |
| 2010/0100160 | A1 | 4/2010 | Edman et al. |
| 2010/0292578 | A1 | 11/2010 | Sato |
| 2011/0260176 | A1 | 10/2011 | Onoe et al. |
| 2012/0078123 | A1 | 3/2012 | Futatsuyama et al. |
| 2012/0245439 | A1* | 9/2012 | Andre .................. A61B 5/0022 600/595 |
| 2013/0030259 | A1 | 1/2013 | Thomsen et al. |
| 2013/0261415 | A1 | 10/2013 | Ashe et al. |
| 2013/0310700 | A1 | 11/2013 | Wiard et al. |
| 2015/0282718 | A1 | 10/2015 | Wiard et al. |
| 2015/0359457 | A1* | 12/2015 | Blumenthal .......... A63F 13/218 73/172 |
| 2016/0038037 | A1 | 2/2016 | Kovacs |
| 2016/0045117 | A1* | 2/2016 | Liu .................... A61B 5/02405 600/502 |
| 2016/0095522 | A1 | 4/2016 | Wiard et al. |
| 2016/0128582 | A1 | 5/2016 | Chod et al. |
| 2016/0256108 | A1* | 9/2016 | Yun ........................ G16H 50/20 |
| 2016/0374619 | A1 | 12/2016 | Borkholder et al. |
| 2017/0000350 | A1 | 1/2017 | Kwon et al. |
| 2017/0079591 | A1 | 3/2017 | Gruhlke et al. |
| 2017/0127959 | A1 | 5/2017 | Paulussen et al. |
| 2017/0188963 | A1 | 7/2017 | Banet et al. |
| 2017/0238818 | A1* | 8/2017 | Gaurav ................ A61B 5/7264 |
| 2017/0245767 | A1* | 8/2017 | Ferber .................. A61B 5/7257 |
| 2017/0360316 | A1 | 12/2017 | Gu et al. |
| 2018/0125376 | A1* | 5/2018 | Denney, Jr. ........... A61B 5/085 |
| 2018/0132736 | A1 | 5/2018 | Silverman |
| 2018/0199824 | A1 | 7/2018 | Centen et al. |
| 2018/0296136 | A1 | 10/2018 | Foxlin et al. |
| 2018/0303428 | A1* | 10/2018 | Yamashita ............... A61B 5/11 |
| 2018/0360323 | A1 | 12/2018 | Lui |
| 2019/0008431 | A1 | 1/2019 | Bechtel et al. |
| 2019/0038151 | A1 | 2/2019 | Lee et al. |
| 2019/0099116 | A1 | 4/2019 | Wiese et al. |
| 2020/0205681 | A1 | 7/2020 | Putila |
| 2020/0305740 | A1 | 10/2020 | Quan et al. |
| 2021/0244302 | A1* | 8/2021 | Lizio .................... A61B 5/7239 |
| 2021/0345929 | A1 | 11/2021 | Wróblewski et al. |

FOREIGN PATENT DOCUMENTS

| | | |
|---|---|---|
| CN | 106020564 A | 10/2016 |
| CN | 108801421 A | 11/2018 |
| CN | 110251105 A | 9/2019 |
| JP | 2002-172094 A | 6/2002 |
| JP | 2008104667 A | 5/2008 |
| JP | 2008-237686 A | 10/2008 |
| JP | 2013169464 A | 9/2013 |
| JP | 2017-000415 A | 1/2017 |
| WO | 85/03211 A1 | 8/1985 |
| WO | 2015/127193 A1 | 8/2015 |
| WO | 2017/171228 A1 | 10/2017 |
| WO | 2019/170903 A1 | 12/2019 |

OTHER PUBLICATIONS

Anonymously, "Bootstrapping (statistics)", https://web.archive.org/web/20190408054026/https://en.wikepedia.or(wiki/Bootstrapping_(statistics), Wikipedia, XP093129092, Publication date Apr. 8, 2019, 13 pages.

Resampling (statistics) [retrieved from internet on Apr. 7, 2025]. Retrieved from <https://en.wikipedia.org/w/index.php?title=Resampling_(statistics)&oldid=917587664>. Sep. 24, 2019.

* cited by examiner

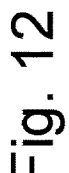
Fig. 12
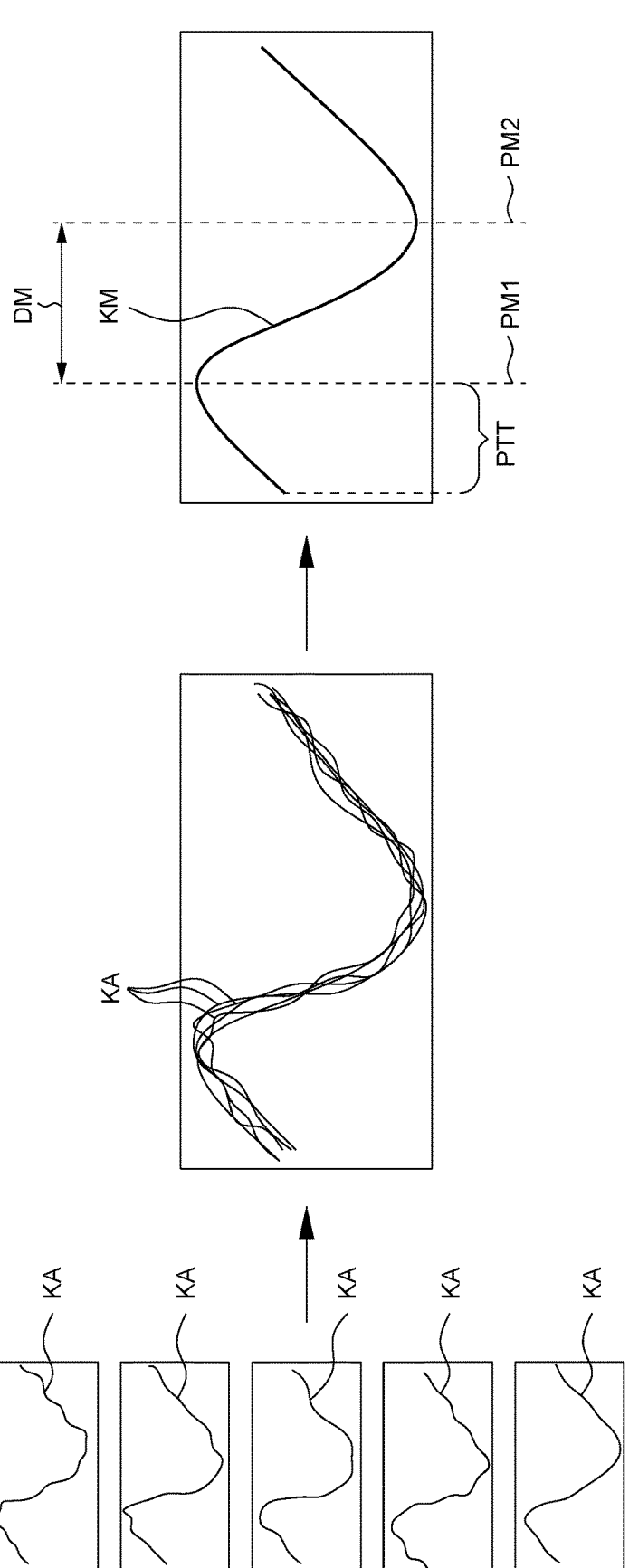

METHOD AND EXAMINATION APPARATUS FOR MEDICAL EXAMINATION OF AN ANIMAL

BACKGROUND OF THE INVENTION

Field of the Invention

The present invention relates to a method for medical examination of an animal as well as an examination apparatus, a computer program and a computer-readable storage medium.

Generally, it is an aim of the present invention to enable or simplify a noninvasive blood pressure measurement in pets such as cats or dogs. In humans, an inflatable cuff, which is placed around the arm, is often used for non-invasive blood pressure measurement. However, measuring blood pressure with a cuff is not unproblematic for dogs and in particular for cats, because these animals are not used to such examinations and in particular for cats it can thus be difficult to put on a cuff. On the other hand, the application of a cuff is also associated with stress for the animal, which should be avoided if possible, as the stress can falsify the result of the measurement.

However, the present invention is not limited to the application to pets such as cats or dogs, but can in principle be used for any kind of animal, in particular humans as well. Furthermore, the present invention is not limited to a blood pressure measurement, but is generally designed or suitable for medical examination, in particular an optical, non-invasive and/or percutaneous examination, particularly preferably photoplethysmography and/or pulse oximetry.

Description of Related Art

In addition to a blood pressure measurement using a cuff, other methods for non-invasive determination of blood pressure are already known in the prior art.

International Patent Application Publication WO 85/03211 A1 relates to a method for determining the arterial blood pressure, in which heartbeats are measured by means of an electrocardiography and an arterial blood flow is measured by means of a photoplethysmography. The blood pressure is then determined from the time interval between a heartbeat and a pulse wave in the arteries triggered thereby and measured by the photoplethysmography. This is done by taking advantage of the fact that the blood pressure is correlated with the time span between the heartbeat and the resulting pulse wave in the arteries triggered thereby.

The time between a heartbeat and the resulting pulse wave in the arteries is also called pulse transit time.

International Patent Application Publication WO 89/08424 A1 and corresponding U.S. Pat. No. 5,237,997 relate to a method for the continuous measurement of blood pressure in humans. To determine one of the three blood pressure quantity (systolic, diastolic or mean blood pressure), the pulse transit time is measured continuously, making use of a proband-specific calibration curve which indicates the pulse transit time as a function of the blood pressure quantity used. To measure the pulse transit time, an ECG is recorded by means of two electrodes placed over the patient's heart and a sensor is attached to the earlobe with an ear clip. A small light source of the sensor shines through the earlobe and the transmission of the earlobe, which varies proportionally with the blood pressure, is measured by a photodiode. The temporal transmission curve shows the arrival of the pulse wave at the earlobe relative to the systole registered by the ECG signal. Thus, the pulse transit time is determined for the distance between the heart and the earlobe.

SUMMARY OF THE INVENTION

It is an object of the present invention to provide a solution by which a reliable, accurate, fast and/or non-invasive, in particular cuff-free, medical examination, in particular blood pressure measurement, of animals such as dogs or cats is made possible and the examination or measurement is made as pleasant as possible for the animal.

The above object is solved by a method, an examination apparatus, a computer program and a computer-readable storage medium as described herein.

In particular, the present invention relates to a method for the medical examination of an animal. In particular, a blood pressure of the animal is determined with the method. The determined blood pressure can in particular be a diastolic blood pressure.

Furthermore, the method is preferably configured and/or suitable for the examination of animals having a paw, preferably animals from the superfamily of the Feloidea (cat-like) or Canoidea (dog-like), in particular animals from the family of the Felidae (cats) or Canidae (dogs), particularly preferably animals from the subfamily of the Felinae (small cats) or the tribe of the Canini (true dogs), in this tribe particularly animals of the genus *Canis* (wolf-like and jackal-like), particularly preferably domestic cats or domestic dogs.

In principle, however, the method is suitable for the medical examination, in particular blood pressure determination, of any animals, in particular humans.

In the method according to the invention, an arterial blood flow of the animal is optically examined, preferably with a sensor device. Particularly preferably, a photoplethysmography is performed. Hereby, the application of a cuff can be avoided. Furthermore, the sensor device allows the animal to move freely during the examination. Thus, the examination can be made pleasant and, consequently, stress-free for the animal. This in turn is conducive to an accurate and reliable examination, in particular blood pressure determination.

Further, the method involves recording a curve comprising information about the arterial blood flow of the animal, in particular a photoplethysmogram (PPG), and cutting the curve into several curve sections in such a way that each curve section corresponds to a heartbeat, in particular a single and/or exactly one heartbeat. This is conducive to a reliable and accurate examination, in particular blood pressure determination.

For evaluation of the curve, preferably an averaging is performed on the basis of several curve sections. By the averaging, the evaluation is simplified and/or the accuracy of the evaluation is increased. In particular, noise in the signals and/or curve sections can be suppressed and/or filtered and motion artifacts can be compensated.

It is preferred that a subset of the curve sections is selected for evaluation. In particular, unselected curve sections can be discarded. This increases the accuracy and/or reliability of the method, in particular also if the examination conditions lead to temporary disturbances, for example if the animal to be examined moves.

Preferably, a resampling method, in particular bootstrapping, is used for evaluation, wherein subsamples, in particular bootstrap samples, are generated from the curve sections. This is conducive to the reliability and accuracy of the method.

A subsample preferably has less than 200, preferably less than 100, in particular less than 60, and/or more than 15, preferably more than 30, particularly preferably about 45, curve sections. It has been shown in a surprising way that in the present case even such a small number of curve sections leads to a reliable and accurate result with relatively low computational effort.

It is further preferred that less than 1000, preferably less than 500, in particular less than 250, particularly preferably less than 100, very particularly preferably less than 75, and/or more than 10, preferably more than 30, particularly preferably about 50, subsamples are generated. It has been shown in a surprising way that even with such a small number of subsamples a reliable and accurate result is achieved.

From the curve sections and/or subsamples, a curve feature is preferably determined. Preferably, a curve feature is determined for each subsample and/or an average value is determined from several curve features, which are preferably of the same kind. This increases the accuracy and reliability when determining the curve feature.

Preferably, a measure of dispersion of the curve feature, in particular an interquartile range and/or a standard deviation, is determined. Here it is particularly preferred that several curves are recorded simultaneously and/or successively and one of the curves is selected for further evaluation on the basis of the measure of dispersion. This increases the reliability and accuracy in the determination of the curve feature and/or blood pressure.

Particularly preferred, the blood pressure is determined on the basis of the curve feature by means of a preferably empirically determined correlation function.

Preferably, a cardiogram, in particular an electrocardiogram, is recorded simultaneously with the curve, preferably wherein the curve is cut into curve sections using information from the cardiogram. The cardiogram makes it easier to divide the curve into sections corresponding to heartbeats.

Particularly preferably, QRS complexes of the cardiogram or electrocardiogram, in particular R peaks of QRS complexes, are used to determine times of heartbeats, preferably wherein the curve is cut into curve sections at the times determined by means of the QRS complexes. This is conducive to a simple and accurate determination of the curve feature.

The cardiogram is preferably checked automatically for usefulness. In particular, if the cardiogram is not useful, the cardiogram and, preferably, the curve comprising the information about the arterial blood flow that corresponds to the cardiogram and/or to the respective time segments is discarded. Preferably, a new or different cardiogram is then recorded or another time segment of the cardiogram is then used. Also, a new curve is preferably recorded and/or another time segment of the curve is used that corresponds to the other time segment of the cardiogram. As a result, the usefulness of the cardiogram preferably is a prerequisite for using the curve comprising information about the arterial blood flow for further evaluation. This increases the reliability and accuracy of the method.

Preferably, the curve comprising information about the arterial blood flow is automatically checked for usefulness, wherein, if the curve is not useful, the curve is discarded and a new curve is recorded. This is conducive to a reliability and accuracy of the method.

Preferably, several curves are recorded—simultaneously and/or consecutively—and curve sections from different or several recorded curves are used for evaluation. This is conducive to an increased reliability and accuracy of the method.

With the method, preferably an arterial blood flow of the animal is optically examined with a sensor device. In particular, a photoplethysmography is performed. This eliminates the need for a cuff, making the examination pleasant and stress-free for the animal. This is conducive to an accurate and reliable examination, in particular the determination of blood pressure.

The sensor device preferably comprises one or more emitters of the same kind for emitting electromagnetic radiation and several detectors of the same kind for detecting the radiation emitted by the emitter(s), in particular wherein the emitter(s) and the detectors form several sensors of the same kind.

Preferably, a sensor or a subset of sensors is selected. This is conducive to an accurate and reliable examination, in particular blood pressure determination, and preferably reduces the effort involved in measuring and/or evaluating signals.

Preferably, the sensors each have a sensor or detection region, wherein the sensor region of the sensors are each located at different locations and together form a recording/sensing region, so that with each sensor a different partial region of the sensing region is recorded/sensed or can be recorded/sensed. For medical examination, in particular blood pressure determination, a certain part of the sensing region is selected. In particular, this makes it possible to dispense with a very precise positioning of the paw and/or fixing of the paw relative to the sensors and/or the sensor device. Thus, the examination can be made very pleasant for the animal and thus stress-free. This is conducive to a reliable and accurate examination, in particular blood pressure determination, and preferably reduces the effort involved in measuring and/or evaluating signals.

Preferably, it is checked whether a paw is located in a sensor or detection region of a sensor. For this check, a signal recorded with the sensor is analyzed. In particular, an absolute signal strength of the signal is examined for exceeding or falling below a threshold value. In particular, this makes it possible to dispense with a very precise positioning of the paw and/or fixing of the paw relative to the sensors and/or the sensor device. Thus, the examination can be made very pleasant for the animal and thus stress-free. This is conducive to an efficient, fast, accurate and/or reliable examination, in particular blood pressure determination.

Preferably, the sensors are used to record several curves or one curve at a time, which contain information about an arterial blood flow, in particular photoplethysmograms (PPGs). At least one of the curves or a part of this can be selected for evaluation. In particular, (only) a subset of all recorded curves or parts thereof is selected for evaluation and/or unselected curves or parts thereof are discarded. In particular, this allows to compensate motion artifacts or errors caused by a movement of the animal and/or paw during measurement and/or recording. This is conducive to an accurate and reliable examination, in particular blood pressure determination.

Particularly preferably, a quality of the recorded curves is determined by means of a statistical analysis and the curve with the highest quality is selected for evaluation. In principle, several curves of the same or similar quality can be selected. In particular, this allows to compensate motion artifacts or errors caused by a movement of the animal and/or paw during measurement and/or recording. This is conducive to a reliable and accurate examination, in particular blood pressure determination.

A curve selected for evaluation is preferably divided into curve sections, particularly preferably wherein only a subset of the curve sections of the selected curves is used for evaluation. In particular, this allows to compensate motion artifacts or errors caused by a movement of the animal and/or paw during measurement and/or recording. This is conducive to an accurate and reliable examination, in particular blood pressure determination.

It is preferable to record several curves—in particular one after the other—and to divide the curves into curve sections, whereby curve sections of curves recorded one after the other with the same sensor are used for evaluation. This is conducive to a reliable and accurate examination, in particular the determination of blood pressure. In particular, this make it possible to apply the method when the animal moves during the examination, too, and thus individual curves or curve sections become unusable.

Alternatively, or additionally, several curves can be recorded simultaneously and curves can be divided into curve sections, wherein curve sections of curves recorded simultaneously with different sensors are used for evaluation. This is conducive to a reliable and accurate examination, in particular the determination of blood pressure. In particular, this make it possible to apply the method when the animal moves during the examination, too, and thus individual curves or curve sections become unusable.

Because several curves are recorded simultaneously and/or consecutively and curve sections of one or more of these curves can be used for evaluation, the proposed method is particularly flexible. The curves simultaneously recorded with different sensors are in particular recorded at different locations, so that the curves preferably represent different regions of the cat paw. This allows a reliable and accurate examination, in particular blood pressure determination, even if the paw is not optimally positioned for one or more of the sensors and/or the paw is moved during the examination.

Preferably, a curve feature, in particular a pulse transit time, is determined by means of the curve(s). From the curve feature, in particular the pulse transit time, the blood pressure is preferably determined by means of a preferably empirically determined correlation function.

The curves are preferably each cut into curve sections that correspond to a, in particular exactly one, heartbeat. From these several curve sections, an average value is preferably calculated. In particular, this allows to compensate motion artifacts or errors caused by a movement of the animal and/or paw during measurement and/or recording. This is conducive to a reliable and accurate examination, in particular blood pressure determination.

It is particularly preferred to record a cardiogram at the same time as the curves and to cut the curves into curve sections using information from the cardiogram. This is conducive to a reliable and accurate examination, in particular the determination of blood pressure.

According to another aspect, the present invention relates to an examination apparatus for medical examination, in particular determination of a blood pressure of animals, in particular animals having a paw, particularly preferably animals from the subfamily Felinae, particularly preferably domestic cats.

The examination apparatus has a sensor device for the optical examination of an arterial blood flow of the animal, in particular for performing a photoplethysmography.

For this purpose, the examination apparatus preferably has at least one emitter for emitting electromagnetic radiation, in particular light including infrared radiation, and at least one detector for detecting the radiation emitted by the emitter, in particular light including infrared radiation.

Furthermore, the examination apparatus has means and/or a measuring and/or evaluation device which are suitable for carrying out the steps of the method according to the invention.

According to another aspect, which can also be realized independently, the present invention relates to an examination apparatus for the medical examination of animals. The examination apparatus is in particular designed for the determination of a blood pressure. Furthermore, the examination apparatus is preferably designed and/or suitable for the examination of animals with one paw from the superfamily of the Feloidea (cat-like) or Canoidea (dog-like), in particular animals from the family of the Felidae (cats) or Canidae (dogs), particularly preferably animals from the subfamily of the Felinae (small cats) or the tribe of the Canini (true dogs), in this tribe particularly animals of the genus *Canis* (wolf-like and jackal-like), particularly preferably domestic cats or domestic dogs.

In principle, however, the examination apparatus according to the invention is suitable for the medical examination, in particular the determination of blood pressure, of any animals, in particular humans as well.

The examination apparatus has a sensor device for optical examination of an arterial blood flow of the animal. The examination apparatus is preferably designed for percutaneous and/or non-invasive examination of the blood flow and/or animal. The sensor device and/or examination apparatus is particularly preferably designed for performing a photoplethysmography.

The sensor device comprises one or more emitters of the same kind for emitting electromagnetic radiation and several detectors of the same kind for detecting the radiation emitted by the emitter(s), the emitter(s) and the detectors forming several sensors of the same kind.

According to the invention, it is provided that the examination apparatus has a control which is designed to select a sensor or a subset of sensors. This is conducive to a reliable, fast and accurate examination, in particular blood pressure determination.

The sensors preferably have several emitters each. This is conducive to a reliable and accurate examination, in particular the determination of blood pressure.

Alternatively, or additionally, the emitters are each part of several sensors. This way, the number of required emitters can be reduced and/or kept low, which simplifies the design of the examination apparatus and makes the examination apparatus more cost effective.

Preferably, each sensor has a sensor region, wherein the sensor regions of the sensors are each located at different locations and together form a sensing region, so that each sensor region forms a different partial region of the sensing region and different partial regions of the sensing region are selectable by means of the control. In particular, this makes it possible to dispense with a very precise positioning of the paw and/or fixing of the paw relative to the sensors and/or the sensor device. Thus, the examination can be made very pleasant for the animal and thus stress-free. This is conducive to a reliable and accurate examination, in particular blood pressure determination.

The examination apparatus and/or control is preferably designed to perform the method according to the invention.

The examination apparatus preferably has means adapted to execute the method according to the invention.

According to another aspect, the present invention relates to a computer program comprising instructions which, when executed by the computer program, cause the examination apparatus to execute the steps of the method.

According to another aspect, the present invention relates to a computer-readable storage medium having the computer program stored thereon or on which instructions are stored which, when executed, cause the examination apparatus to execute the steps of the method.

As a result, the present invention makes it possible to measure blood pressure in animals, in particular also in animals which, according to experience, have a high urge to move and/or a low stress tolerance with regard to manipulation of the animal's body, as is the case in particular with domestic dogs and domestic cats.

Here, in the past, a blood pressure measurement was always associated with considerable stress for the animal. The present invention solves this problem by a complete departure from known approaches in which animals are fixed and/or sensor technology is fixed to animals. The present invention provides a remedy in an unpredictable and surprising way by combining measures which—instead of requiring a restriction of movement—do not restrict the freedom of movement at least essentially. Instead of fixing the animal, measurement problems that may be caused by a possible movement of the animal during the examination are technically solved. In particular, so-called movement artifacts, i.e. measurement inaccuracies and measurement errors caused by movement, are eliminated and/or compensated.

In order to achieve this goal, different measures are described and/or applied, which can be realized individually, but interdigitate with each other and thus enable a particularly reliable and equally low-stress blood pressure determination in a synergistic way.

So on the one hand it is preferably intended that the position of the animal, in particular thus the position of the paw, is not strictly given. Instead, several sensors are used and the sensor that is suitable for a measurement can be selected.

This is preferably combined with further measures, each of which can be implemented individually and combined in a particularly advantageous way, in order to preferably ultimately determine a curve feature from the measured curve(s), and in particular to determine a blood pressure on the basis of the curve feature.

Particularly advantageous and the basis of some of the further measures is the subdivision or cutting of signals or curves into curve sections on the basis of the simultaneously determined cardiogram. Another basis of most of the proposed measures is the averaging between the curve sections.

In addition, there is in particular the selection of suitable curve sections and/or the selection from several alternative results determined for the curve feature and/or filter measures and/or statistical methods. In particular, these and further measures described in detail lead to the fact that a simple placing of a paw or paws on or at the sensor device and/or putting the animal on the examination apparatus is sufficient to achieve a meaningful determination of the curve feature and a reliable determination of the blood pressure therefrom. This seemed to be impossible in this form before.

An "animal" in the sense of the present invention is preferably a vertebrate, in particular a mammal, particularly preferably a land mammal. In particular, the term "animal" within the meaning of the present invention also includes humans. Preferably, the animal to be examined has a paw.

Preferably, the animal to be examined is an animal from the superfamily of the Feloidea (cat-like) or Canoidea (dog-like), in particular an animal from the family of the Felidae (cats) or Canidae (dogs), in particular preferred is an animal from the subfamily of the Felinae (small cats) or the tribe of the Canini (true dogs), in this tribe in particular an animal of the genus *Canis* (wolf-like and jackal-like), particularly preferred a domestic cat or a domestic dog.

An "emitter" in the sense of the present invention is preferably a structure which is emits or is designed to emit electromagnetic radiation, in particular in the optical and/or infrared range. Preferably, an emitter is formed by a light-emitting diode, a laser diode, or generally a light-generating element. However, an emitter can also be formed by the end of an optical fiber at which light guided by the optical fiber exits—at least as far as a position of the emitter is concerned. Depending on the point of view, the combination of the light guide with its associated light source is then the emitter. In principle, the term "emitter" in the sense of the present invention is therefore preferably to be understood broadly.

A "detector" in the sense of the present invention is preferably a structure which is designed to detect electromagnetic radiation, in particular in the optical and/or infrared range. Preferably, a detector is formed by a photodiode. In principle, however, a detector can also be formed by another structure which is designed for the detection of electromagnetic radiation emitted in particular by the emitter, for example a photocathode, a photocell, a CCD sensor or the like. The detector may also have a light guide with one end where light guided by the light guide can enter. In this case, the end of the light guide is the detector, at least as far as a position of the detector is concerned.

An "emission region" of an emitter in the sense of the present invention is preferably a region into which radiation emitted by the emitter reaches or can reach. Preferably, an emitter emits radiation in a certain direction, for example in a certain angular range. The emission region is therefore preferably defined or limited by one or more emission angles. The emission region can be essentially conical.

A "detection region" of a detector in the sense of the present invention is preferably a region from which radiation reaches or can reach the detector. A detection region is preferably defined or limited by one or more detection angles. The detection region can be essentially conical.

A "sensor" in the sense of the present invention is preferably a combination of at least one emitter with at least one detector. In particular, a detector with one or more emitters forms a sensor in the sense of the present invention. A sensor preferably comprises exactly one detector and at least one emitter. The emitter is designed to emit electromagnetic radiation with a wavelength at which the detector is sensitive and/or can detect this electromagnetic radiation.

A "sensor region" of a sensor in the sense of the present invention is preferably a region which is detectable/sensable by means of the sensor or in which a measurement can be made by means of a sensor. In particular, a sensor region is a region in which the emission region of an emitter and the detection region of a detector of the sensor overlap. A sensor region can be formed by a continuous region or by several disjunctive or separated regions.

A "sensor device" in the sense of the present invention is preferably a device having one or more sensors. In particular, a sensor device is a device for optical examination of a body part of an animal. The sensor device is in particular designed for performing a photoplethysmography.

A "sensing region" of the sensor device in the sense of the present invention is preferably a region which is detectable/ sensable by means of the sensor device and/or the emitters and/or the detectors. The sensing region is in particular a region in which an emission region of an emitter and a detection region of a detector overlap. Preferably, the sensing region is formed by one or more emission regions and one or more detection regions that overlap. The sensing region can be connected or can be formed by several separate regions. In particular, the sensing region can be formed by one or more overlapping regions of essentially conical emission and detection regions.

A "periodic" arrangement of emitters and/or detectors in the sense of the present invention is preferably an arrangement in which the emitters and/or detectors are arranged in a structure which is repeated at at least substantially equal intervals. Such periodicity can be present in one or more directions, which are in particular orthogonal to each other.

An "optical examination" in the sense of the present invention is preferably an examination in which a body part of an animal is irradiated with electromagnetic radiation in the optical range and/or range visible to humans and/or in the infrared range, in particular with a wavelength between 380 nm and 1400 nm, and in which the radiation reflected and/or scattered by the body part and/or radiation transmitted through the body part is measured by means of a detector. The optical examination is preferably a reflectometric examination. Conclusions can then be drawn from the reflected, scattered and/or transmitted radiation, for example with regard to the arterial blood flow. In particular, electromagnetic radiation of a defined wavelength or a defined wavelength range is used in an optical examination. Particularly preferably, an optical examination is a non-invasive and/or percutaneous examination of the inside of the body.

A "photoplethysmography" in the sense of the present invention is a method for optical examination of an arterial blood flow of an animal. In particular, a photoplethysmography is a method for non-invasive optical examination in which a body part of an animal is irradiated with electromagnetic radiation, in particular in the range visible to humans and/or the infrared range, and the radiation scattered and/or (in particular diffusely) reflected and/or transmitted by the body part is measured by means of a detector. The reflection and/or scattering and/or transmission, in particular the proportion of the electromagnetic radiation reflected or transmitted in the direction of the detector, depends, among other things, on the arterial blood flow, in particular the volume of the arterial blood and/or the oxygen saturation of the arterial blood. Preferably, the variation of the arterial blood flow and/or the change in volume and/or the change in oxygen saturation of the arterial blood changes the signal measured by the detector, so that variations in the measured signal and/or the course of the measured signal allow conclusions to be drawn about the arterial blood flow. Accordingly, pulse oximetry is also an (extended) photoplethysmography in the sense of the present invention.

In the sense of the present invention, a pulse oximetry comprises at least one photoplethysmography. In a pulse oximetry, the oxygen content in the blood is determined, wherein two photoplethysmographies are carried out, in particular simultaneously, to determine the oxygen content, wherein different wavelengths are used for these two photoplethysmographies. From the different absorption rates at the two wavelengths, the oxygen saturation of the blood can then be determined.

A "photoplethysmogram" in the sense of the present invention is in particular the curve recorded or measured during the performance of a photoplethysmography.

However, also known from the state of the art are optical examinations, for example to determine the oxygen content in the blood, that do not represent or include photoplethysmography. In particular, the methods of cerebral oximetry and tissue oximetry do not include photoplethysmography. These methods are also not suitable for examination of the arterial blood flow, in particular due to the wavelengths of the electromagnetic radiation used.

A "cardiogram" in the sense of the present invention is preferably a curve representing the activity of the heart of the animal. Particularly preferably, the cardiogram is recorded electrically, in particular by means of electrodes which are brought into contact with the skin of the animal, and/or is an electrocardiogram. In principle, however, other methods for recording a cardiogram are also conceivable, for example an impedance cardiogram or an acoustic recording, so that the cardiogram is a phonocardiogram.

A "detection element" in the sense of the present invention is preferably an element for detecting an activity of the heart of the animal. A detection element is in particular suitable or designed for recording a cardiogram. A detection element is preferably formed by an electrode. However, the detection element may also be formed by a microphone or other sound sensor or the like or have this/these.

An "arterial blood flow" in the sense of the present invention is preferably the flow of blood through the arteries. Arteries are in particular blood vessels that lead the blood away from the heart. In particular, the arterial blood flow is a blood flow of the animal to be examined.

A "blood pressure" in the sense of the present invention is preferably a pressure (force per area) of the blood in a blood vessel, in particular a blood vessel of the animal to be examined. The blood vessel is preferably an artery. Preferably, the blood pressure is a blood pressure in the larger arteries. The blood pressure can be a systolic, diastolic and/or mean blood pressure. In particular, it has been surprisingly shown in the context of the present invention that the proposed method and/or examination apparatus can also be used for the determination of a diastolic blood pressure. This is, however, not mandatory.

A "curve" in the sense of the present invention is preferably the time course of a signal measured by means of a detector or sensor. The term "curve" also includes data-technical equivalents such as individual data points, which (together) represent or correspond to the course. A curve is preferably a temporal course over several heartbeats.

A "curve section" in the sense of the present invention is preferably a section or part of a curve, i.e. in particular also a time course of a signal measured by a detector or sensor. In particular, a curve section is a section of a curve corresponding to a heartbeat, in particular beginning at the time of a heartbeat and preferably ending at the time of a subsequent heartbeat.

A "curve comprising information about an arterial blood flow" in the sense of the present invention is in particular a curve which allows conclusions to be drawn about the arterial blood flow, in particular the arrival of a pulse wave, the change in the blood volume in the arteries, the change in the oxygen saturation of the blood in the arteries or the like. A photoplethysmogram is a particularly preferred example of a curve comprising information about arterial blood flow.

A "curve feature" in the sense of the present invention is preferably a feature of a curve and/or a section of a curve, which in particular comprises information about an arterial blood flow. The curve feature is preferably a feature which is related to a pulse transit time and/or a blood pressure, and/or is correlated with a pulse transit time and/or a blood pressure. In particular, a curve feature is a feature by means
of which the blood pressure can be determined. The curve
feature is particularly preferably a feature of the curve and/or
the curve section that corresponds to a course and/or a form
of the curve and/or the curve section and/or contains infor-
mation about a form of the curve and/or the curve section.
For example, the curve feature can be a position of an
(absolute) extremum, a distance between (absolute)
extrema, a position or an absolute value of a (maximum)
slope, a distance between extrema and/or zero points of the
first and/or second derivative of the curve or a feature of a
Fourier transform of the curve.

Particularly preferably, the curve feature corresponds to a
pulse transit time.

A "pulse transit time" in the sense of the present invention
is preferably the time required by a pulse wave to travel a
distance in the vascular system. Herein, the pressure wave
which passes through the arteries—starting from the heart
due to a heartbeat—is denoted as pulse wave. The velocity
of this pressure wave is in particular higher than the flow
velocity with which the blood flows through the arteries. The
pulse transit time is often abbreviated as "PTT". In particu-
lar, in the present invention, the term pulse transit time
comprises the time between a heartbeat and the arrival of the
pulse wave caused by this heartbeat at a specific location of
an artery, i.e. the time required for the pulse wave to travel
the distance from the heart to the location of the artery.
Preferably, however, the term pulse transit time also includes
the time distance between the arrival of the pulse wave at a
first location and a second location.

A "pulse wave velocity" in the sense of the present
invention is preferably the quotient between the distance
travelled by the pulse wave and the pulse transit time
required by the pulse wave to travel this distance. The pulse
wave velocity is often abbreviated as "PWV".

A "subset" in the sense of the present invention is pref-
erably a proper subset, in particular thus a subset which does
not contain all elements of a superset assigned to the subset.
In particular, a subset of sensors of the sensor device is a set
of sensors that does not contain or have all sensors of the
sensor device.

A "percutaneous" examination in the sense of the present
invention is preferably an examination through the skin. In
an optical percutaneous examination, the interior of the body
is preferably irradiated through the skin with electromag-
netic radiation in the (for humans) optically visible range
and/or infrared range and scattered, transmitted and/or
reflected portions thereof are detected.

A "non-invasive" examination within the meaning of the
present invention is preferably an examination in which the
animal to be examined is not damaged or injured.

A "resampling method" in the sense of the present inven-
tion is preferably an, in particular mathematical and/or
statistical, method, in which statistical properties of "sample
statistics", such as estimators or test statistics, are deter-
mined on the basis of a repeated drawing of samples,
so-called subsamples, from an initial sample. A "sample
statistic" in this sense is preferably any measurable function
of random variables of a sample, the statistic preferably
being used for a statistical purpose. Preferably, in a resam-
pling method, the sample statistic is calculated repeatedly on
the basis of the drawn subsamples and, in particular, the
results are used to examine their distribution properties.

The above-mentioned aspects and features as well as
further aspects and features resulting from the claims and the
following description can be realized independently from
each other and in different combinations.

Further advantages, features, properties and aspects of the
present invention result from the claims and the following
description of preferred embodiments with reference to the
accompanying drawings.

BRIEF DESCRIPTION OF THE DRAWINGS

FIG. 12 is a schematic representation of an averaging of
curve sections.

DETAILED DESCRIPTION OF THE
INVENTION

In the partly not true to scale, only schematic figures, the
same reference signs are used for identical or similar parts,
wherein corresponding or comparable characteristics and
advantages can be achieved, even if a repeated description
is omitted.

Figure 1:
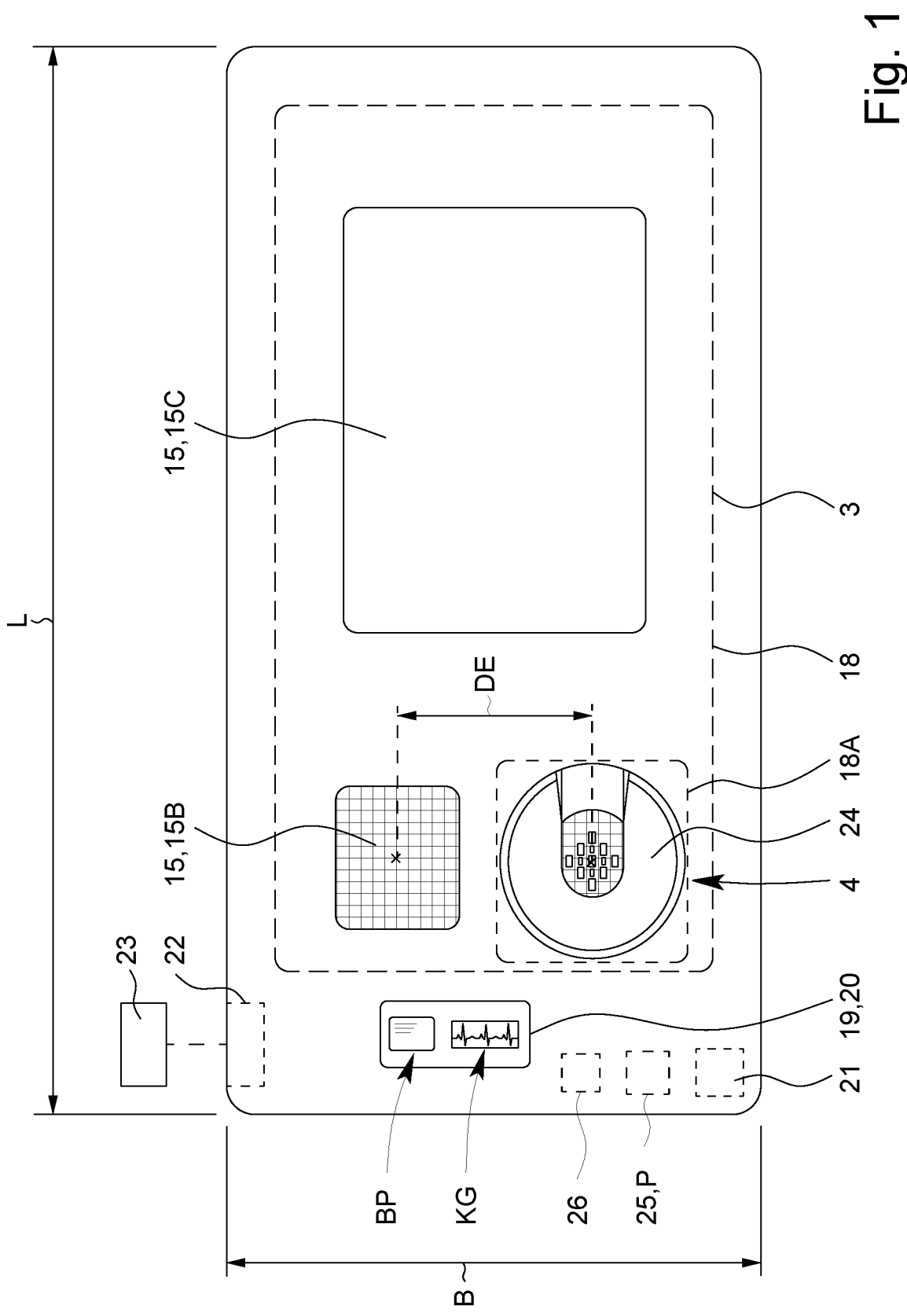
FIG. 1 is a schematic top view of an examination appa-
ratus according to the invention.

FIG. 1 shows a schematic top view of an examination
apparatus 1.

The examination apparatus 1 is preferably designed for
medical examination, in particular for determining a blood
pressure BP, of an animal T, in particular an animal T having
a paw 2, preferably an animal T from the subfamily of the
Felinae, particularly preferably a domestic cat.

In principle, however, the examination apparatus 1 is
suitable for the medical examination of any animal T, in
particular humans, in particular those in which a blood
pressure BP can be determined. For examination using the
examination apparatus 1, it is particularly advantageous if
the animal T has a paw or the like.

However, the examination apparatus 1 may also be
designed and/or suitable for the medical examination, in
particular for the determination of blood pressure BP, of
other animals T, in particular domestic animals, such as
dogs, mice, rats, rabbits, guinea pigs or the like and/or
specially adapted for the examination of these animals T.

The blood pressure BP can be a systolic, diastolic and/or mean blood pressure BP. In particular, it has been surprisingly shown in the context of the present invention that the proposed method and/or examination apparatus can also be used for the determination of a diastolic blood pressure BP. This is, however, not mandatory.

Figure 2:
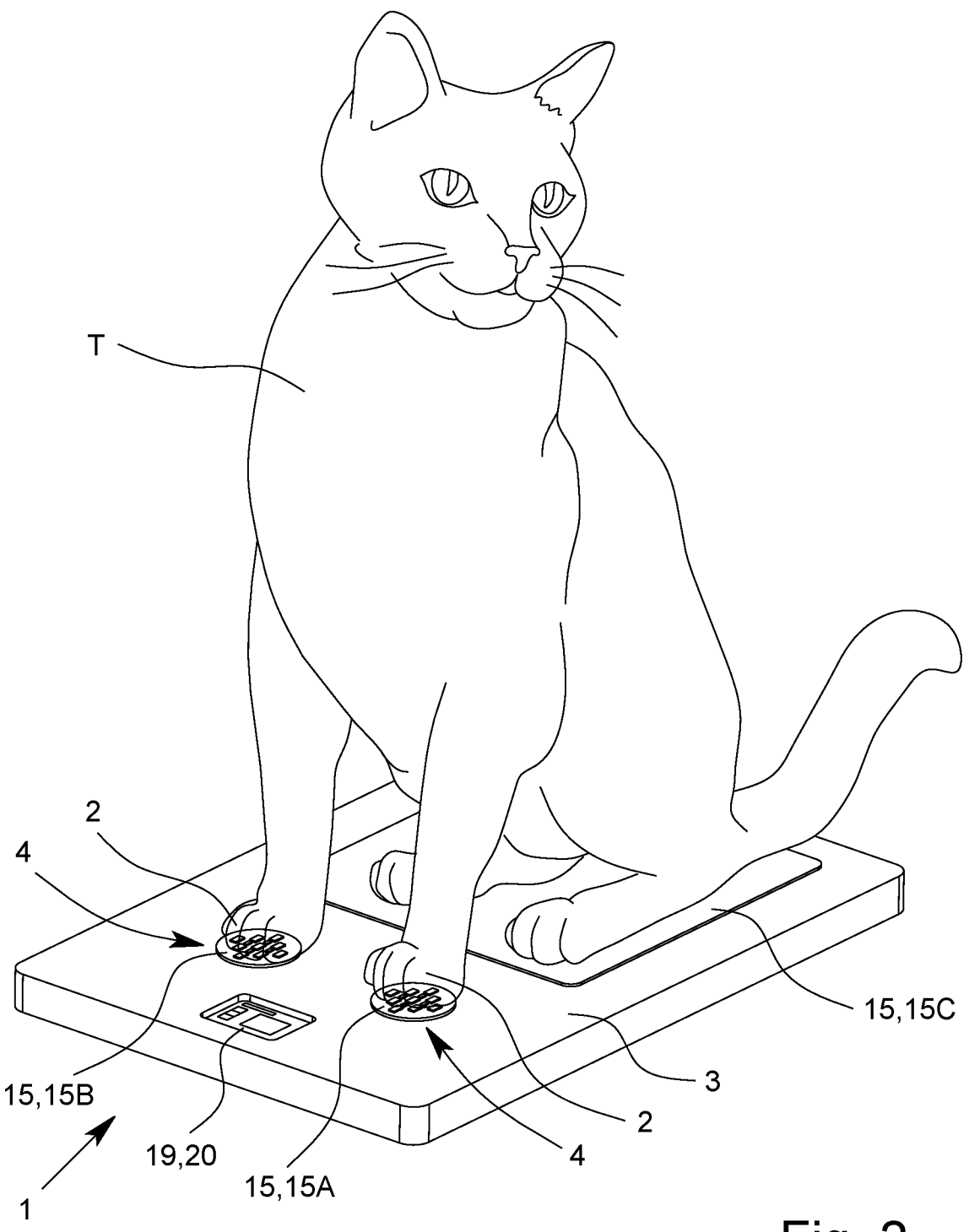
FIG. 2 is a schematic perspective view of an examination
apparatus according to the invention with an animal placed
thereon.

In FIG. 2, an examination apparatus 1 according to the invention is shown in a schematic perspective view with an animal T arranged on it.

Preferably, the examination apparatus 1 is designed as a support for at least one paw 2 or any other part of the body, in particular a part similar to a paw, for example a hand or a finger, of the animal T.

Particularly preferably, the examination apparatus 1 and/or support is designed in such a way that the animal T to be examined can be completely placed and/or positioned on the examination apparatus 1 and/or support, in particular thus all legs of the animal T can be positioned on the examination apparatus 1. However, this is not mandatory. In principle, it is also possible that the examination apparatus 1 is designed so that only one or two paws 2 can be placed or positioned on the examination apparatus 1.

The examination apparatus 1 is preferably designed as mat or plate or mat-like or plate-like or in the form of a mat or plate. In particular, a plate or mat is understood to be a device whose width and length exceed the height by a multiple. A plate is preferably understood to be an at least substantially rigid apparatus. A mat is preferably understood to be an at least partially flexible apparatus. For example, if the examination apparatus 1 is designed as a mat, it may be at least partially rollable and/or foldable.

Preferably, the examination apparatus 1 has a rest surface 3. The animal T, in particular a domestic dog, a domestic cat or another animal T of comparable or smaller size, can be, preferably completely, placed on the rest surface 3.

Preferably, the examination apparatus 1 and/or rest surface 3 is at least essentially flat and/or planar.

Preferably, the examination apparatus 1 has the rest surface 3 on one upper side and/or the rest surface 3 is formed by an upper side of the examination apparatus 1 or a part thereof.

The rest surface 3 is or forms in its position of use, in particular during the examination, preferably an at least substantially horizontal surface. The position of use is a preferred position of the examination apparatus 1, in which the animal T can be placed on the examination apparatus 1 for examination. The position of use is in particular shown in FIG. 2.

The examination apparatus 1 and/or rest surface 3 preferably has a width B of more than 20 cm, preferably more than 40 cm, and/or less than 80 cm, preferably less than 60 cm.

The examination apparatus 1 and/or rest surface 3 preferably has a length L of more than 40 cm, preferably more than 60 cm, and/or less than 120 cm, preferably less than 80 cm. In principle, a different width B and/or a different length L of the examination apparatus 1 and/or rest surface 3 are also conceivable.

It is preferably intended that during the examination the examination apparatus 1 contacts the paw 2 and/or the body part only on one side, and/or rests or is arranged only on one side. The examination apparatus 1 is therefore preferably designed for one-sided contact with the animal T and/or its paw 2.

The examination apparatus 1 is preferably free of fixing means and/or fastening means. Preferably, the examination apparatus 1 is not designed to clasp the paw 2. Preferably, the examination apparatus 1 does neither have a clip for attachment to the paw 2 nor a cuff for application to the paw 2 or other fixing means or fastening means for attaching, fixing or fastening an examination means such as a sensor or an electrode to the animal T. In contrast, it is preferred that the examination apparatus 1 has a contact and rest surface 3, by which the examination is made possible when the paw 2 or body part is put on or placed on the device.

The design of the examination apparatus 1 as a support and/or with a rest surface 3 for the animal T makes the examination particularly pleasant and thus stress-free for the animal T. Preferably, it is not intended that the animal T is fixed to the examination apparatus 1 for examination or that a part of the examination apparatus 1, such as a sensor or the like, is attached or fixed to the animal T. It has been shown that such a method causes stress in an animal T, so that the examination would be unpleasant for the animal T and, in addition, the blood pressure BP would be influenced by the stress. In contrast, by designing the examination apparatus 1 according to the invention, the examination can be made very pleasant and stress-free for the animal T.

Preferably, the examination apparatus 1 or rest surface 3 is designed in such a way that the animal T can move freely on the examination apparatus 1 and/or rest surface 3.

By the design of the examination apparatus 1 described in more detail below, in particular the design and/or arrangement of the sensor device 4 and/or the electrodes 15, it is accomplished that an examination of the animal T, in particular a reliable and/or accurate blood pressure determination, is made possible while avoiding fixation of the animal T or can be made without fixation of the animal T and/or can be made or is made possible when the animal T moves during the examination by means of the examination apparatus 1.

The examination apparatus 1 preferably has a sensor device 4. The sensor device 4 is designed for the optical examination of an arterial blood flow BF of the animal T, in particular for recording a curve K that contains information about an arterial blood flow BF of the animal T. In particular, the sensor device 4 is designed to perform a photoplethysmography and/or to record a photoplethysmogram.

A curve K comprising information about the arterial blood flow BF is shown as an example in FIG. 9 and will be explained in more detail later.

The sensor device 4 and/or examination apparatus 1 is preferably designed to enable or allow movement of the animal T during the examination and/or to enable a reliable and accurate examination, in particular blood pressure determination, and/or to reduce, avoid and/or compensate for movement artifacts.

The examination apparatus 1 has the sensor device 4 preferably in the area of the rest surface 3. Thus, an examination with the sensor device 4 can be performed when the paw 2 or the body part is placed on the surface.

The sensor device 4 is preferably arranged at the examination apparatus 1 or integrated into the examination apparatus 1 in such a way that a paw 2 of the animal T can be positioned at, above and/or in the immediate vicinity of the sensor device 4, in particular if the animal T is located on the examination apparatus 1 and/or rest surface 3. In the example shown in FIG. 1, the sensor device 4 is positioned in such a way that the left forepaw 2 of the animal T can be positioned above the sensor device 4 without any problems and in a position that is pleasant and/or natural for the animal T. However, the sensor device 4 can also be provided at another position.

Figure 7:
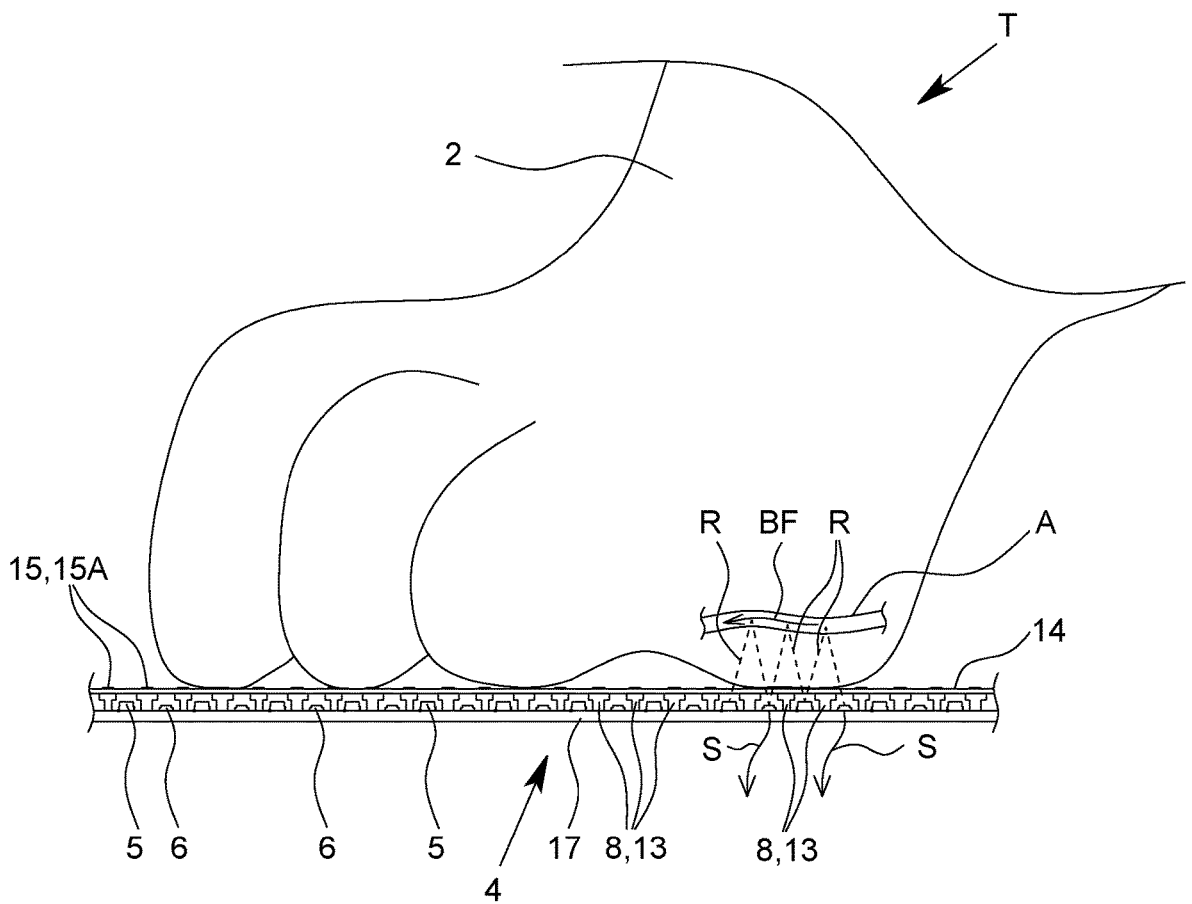
FIG. 7 is a schematic sectional view of the sensor device
with a paw placed thereon.

FIGS. 2 and 7 show, by way of example, the positioning of a paw 2 during an examination by means of the sensor device 4. For the examination by means of the sensor device 4, the paw 2 is preferably positioned in such a way that one or preferably several pads of the paw 2 contact the sensor device 4, in particular a cover 14 and/or electrode 15.

The examination apparatus 1 may also have several, in particular two, sensor devices 4, for example a sensor device 4 for the left forepaw 2 and a sensor device 4 for the right forepaw 2 of an animal T to be examined. In this case, the sensor devices 4 are preferably of a similar or identical design. This is in particular shown in FIG. 2.

The sensor device 4 is preferably designed for a reflective measurement of an arterial blood flow BF.

The sensor device 4 has at least one emitter 5 for emitting electromagnetic radiation R—in particular light including ultraviolet light and/or infrared light—and at least one detector 6 for detecting electromagnetic radiation R, preferably emitted by the emitter 6—in particular light including ultraviolet light and/or infrared light.

The emitter 5 is preferably designed as a light emitting diode or laser diode.

The detector 6 is preferably designed as a photodiode.

Preferably, the emitters 5 can be activated and/or deactivated and/or switched on and/or off separately, in particular by means of MOSFETs assigned to the emitters 5.

Figure 3:
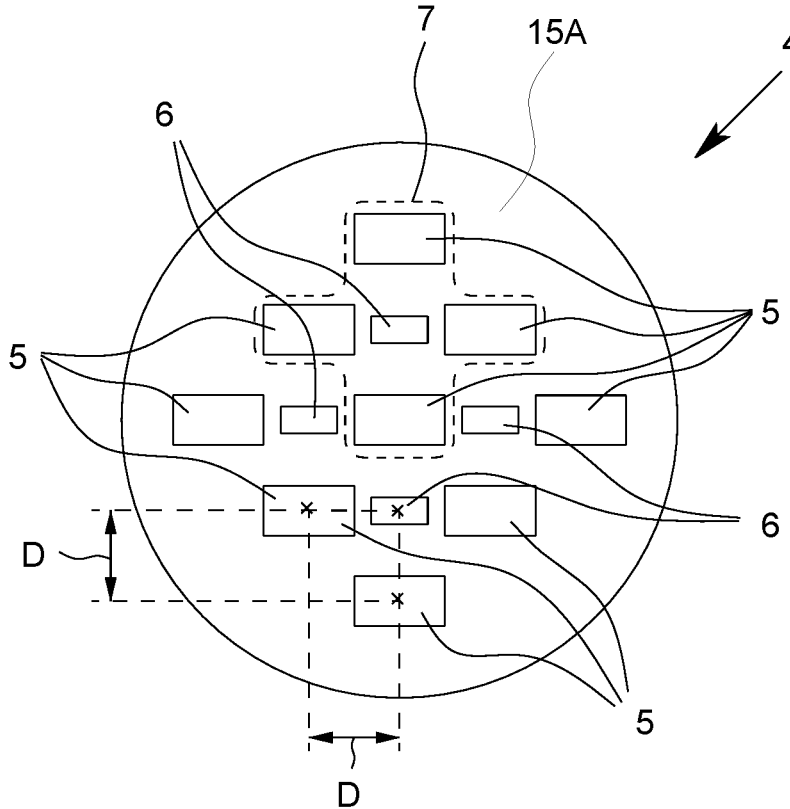
FIG. 3 is a schematic top view of a sensor device
according to a first embodiment.
Figure 4:
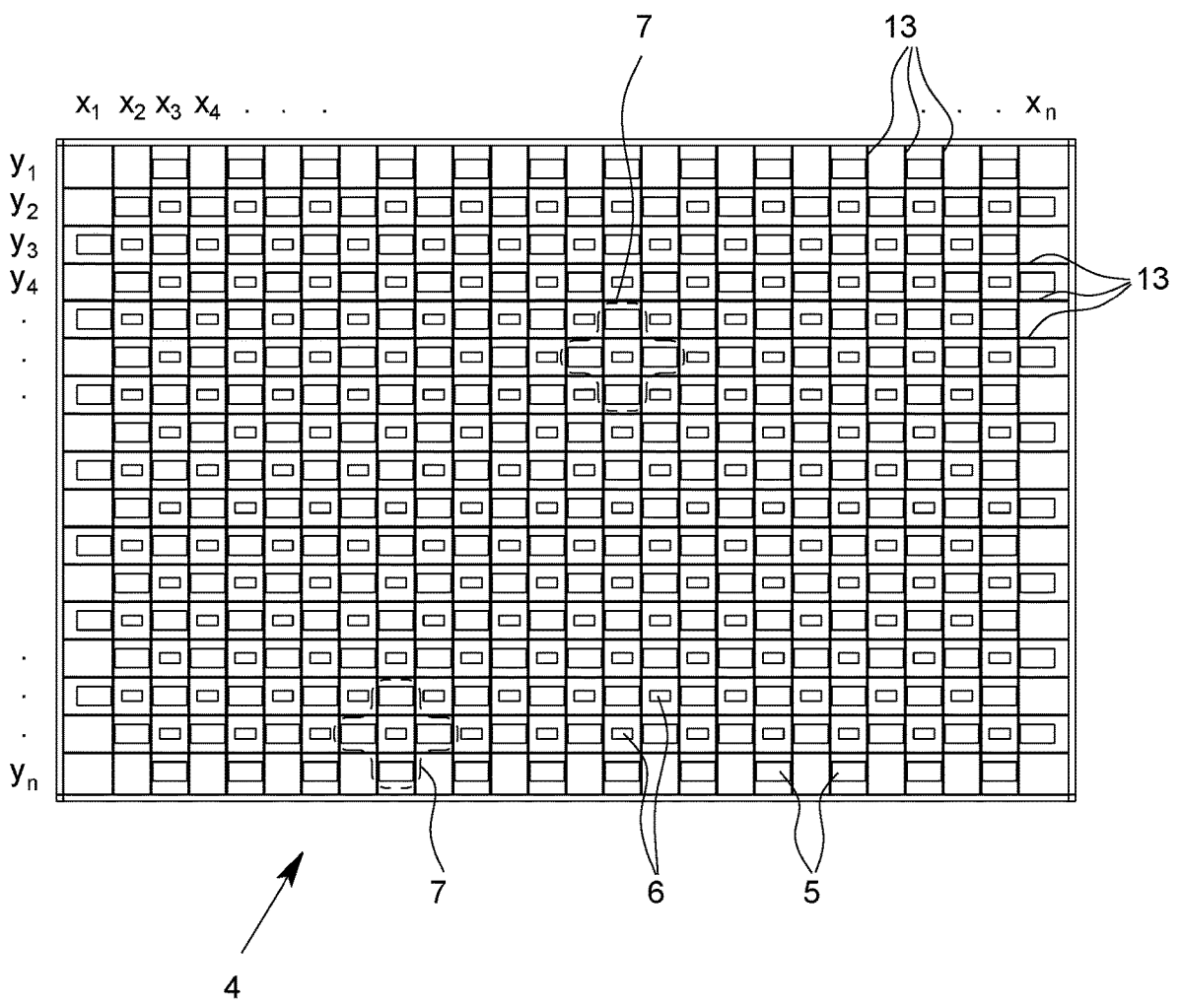
FIG. 4 is a schematic top view of a sensor device
according to a second embodiment.

FIGS. 3 and 4 show an example of a schematic top view of a sensor device 4 in different embodiments. The sensor devices 4 according to FIGS. 3 and 4 are basically the same or similar in design and differ primarily only in the number of emitters 5 and detectors 6.

Preferably, the sensor device 4 has several emitters 5 and several detectors 6. In principle, however, it is also possible that the sensor device 4 has exactly one emitter 5 and exactly one detector 6 or exactly one emitter 5 and several detectors 6 or several emitters 5 and exactly one detector 6.

Preferably, however, the sensor device 4 has at least nine, in the example shown in FIGS. 1 and 3 exactly nine, emitters 5 and/or at least four, in the example shown in FIGS. 1 and 3 exactly four, detectors 6.

The emitters 5 and detectors 6 are preferably arranged in a common plane.

The emitters 5 and detectors 6 are preferably arranged in a recurring and/or repeating structure. Particularly preferably, the emitters 5 and detectors 6 are arranged periodically or in a periodic structure.

Preferably, the emitters 5 and the detectors 6 are arranged in the form of a matrix or in a matrix or an array with or in (virtual) columns and rows. Preferably, the matrix or array has more than two columns and/or more than two rows.

The emitters 5 and detectors 6 are preferably arranged alternately. Preferably, the emitters 5 and detectors 6 form one or more in particular rectilinear rows, with emitters 5 and detectors 6 alternating in each row. The rows can also be curved and/or emulate an organic shape, such as that of a paw 2.

Preferably, —as the case may be with the exception of the emitters 5 and/or detectors 6, which are the outermost and/or arranged at the edge of the sensor device 4 and/or rows and/or matrix—the detectors 6 are each (directly) surrounded by several emitters 5 and/or the emitters 5 are each (directly) surrounded by several detectors 6.

Particularly preferably, several emitters 5 are assigned to each detector 6 or vice versa. This allows preferably the multiple use of emitters 5 and/or detectors 6.

An emitter 5 and detector 6 are in particular assigned to each other if the emitter 5 and the detector 6 are arranged in such a way that the radiation R emitted by the emitter 5, in particular after scattering or reflection in a paw 2, reaches or can reach the detector 6. Particularly preferably, those emitters 5 are assigned to a detector 6 that have the smallest distance D to this detector 6 and/or are (directly) adjacent to this detector 6. Analogously, in particular those detectors 6 are assigned to an emitter 5 that have the smallest distance D to this emitter 5 and/or are (directly) adjacent to this emitter 5.

The distance D between an emitter 5 and a detector 6 is understood in particular as the distance between a center point or geometric center of the emitter 5 or its emission surface and a center point or geometric center of the detector 6 or its detection surface. Preferably, the emitters 5 and detectors 6 are formed by components of different sizes and/or rectangular components, as also indicated by the differently sized rectangles in FIGS. 1 to 4, wherein the emitters 5 and detectors 6 are arranged in such a way that the center points or geometric centers of gravity of these components, indicated by points in FIG. 3, have the same distance D from each other.

Preferably, the emitters 5 assigned to a detector 6 have the same distance D to the detector 6. Analogously, this also applies to the detectors 6 that are assigned to an emitter 5.

The distance D is preferably more than 2 mm, preferably more than 3 mm, in particular more than 4 mm, and/or less than 10 mm, preferably less than 8 mm, in particular less than 7 mm. The distance D is particularly preferably between 4 mm and 6 mm.

Preferably, the emitters 5 of the sensor device 4 are of the same design or kind. Particularly preferably, the emitters 5 of the sensor device 4 are identical in construction and/or designed for emission at the same wavelength or in the same wavelength range.

Preferably, the detectors 6 of the sensor device 4 are of the same design or kind. Particularly preferably, the detectors 6 are identical in construction and/or designed for detection at the same radiation R or wavelength, in particular emitted by the emitters 5.

The sensor device 4 is preferably designed for examination with electromagnetic radiation R in the infrared range. Particularly preferably, the emitters 5 are designed for emission of infrared radiation and/or the detectors 6 are designed for detection of infrared radiation.

Infrared radiation is in particular electromagnetic radiation R with a wavelength between 780 nm and 1400 nm.

Preferably, the emitters 5 are designed for the emission of electromagnetic radiation R with a wavelength of more than 900 nm and/or less than 1200 nm or 1100 nm. Particularly preferably, the emitters 5 are designed for the emission of electromagnetic radiation R with a wavelength of more than 920 nm and/or less than 960 nm, in particular (approximately) 940 nm. Alternatively, or additionally, however, it is also possible that the emitters 5 or a subset of the emitters 5 is/are designed to emit electromagnetic radiation R with a wavelength of more than 1030 nm and/or less than 1070 nm, in particular (approximately) 1050 nm.

The detectors 6 are preferably designed to detect the radiation R emitted by the emitters 5.

Preferably, the sensor device 4 has at least one, preferably several, sensors 7. A sensor 7 has at least one emitter 5 and at least one detector 6 or is formed hereby. Particularly preferably, a sensor 7 has exactly one detector 6 and several emitters 5, in the example shown in FIG. 3 and FIG. 4 exactly four emitters 5.

Preferably, the emitters 5 of a sensor 7 are arranged symmetrically around the detector 6 of the sensor 7 and/or the emitters 5 of the sensor 7 have the same distance D to the detector 6 of the sensor 7.

In particular, the sensor device 4 has several sensors 7 which are of the same type or kind, in particular identical in construction. Particularly preferably, all sensors 7 of the sensor device 4 are identical. Here, however, other solutions are also possible.

In the example shown in FIG. 3, the sensor device 4 has exactly four sensors 7, one of the four sensors 7 being indicated by the dotted line in FIG. 2. Also in FIG. 4 some sensors 7 are indicated by dashed lines.

Preferably, an emitter 5 is assigned to several sensors 7 and/or the emitters 5 each form a part of several sensors 7 (apart from emitters 5, which are arranged at the outermost edge of the sensor device 4). In particular, each emitter 5 is assigned to the adjacent detectors 6 in the row or column and/or to the detectors 6 with the smallest distance D. In the illustration example, the emitters 5—apart from the emitters 5 arranged at the edge—are assigned to four detectors 6 each.

In the embodiment shown, several emitters 5 are assigned to each detector 6, wherein these emitters 5—except for the outermost emitters 5 or emitters 5 arranged at the edge—are, in turn, each assigned to several detectors 6. Hereby, several sensors 7, in particular of the same kind or type, are formed, wherein the emitters 5—except for the outermost emitters 5 or emitters 5 arranged at the edge—are each part of several sensors 7. In the example shown in FIG. 3, the emitter 5 arranged in the center of the sensor device 4 is assigned to each of the four detectors 6. The emitters 5 located in FIG. 3 at the very top, very bottom, very left and very right are assigned to only one detector 6 each. The remaining four emitters 5 in FIG. 3 are assigned to two detectors 6 each. In this way, four sensors 7, in particular of the same kind or type, are formed in FIG. 3.

While FIG. 3 shows the basic design of the sensor device 4 or the basic arrangement of the emitters 5, detectors 6 and/or sensors 7, the sensor device 4 preferably has a considerably larger number of emitters 5, detectors 6 and/or sensors 7, as shown in FIG. 4 as an example. In this way a large sensor area can be realized, so that the exact positioning of a paw 2 for examination and/or blood pressure determination is not or less decisive, but a larger area can be examined by means of the sensor device 4. This makes it possible that the paw 2 of the animal T does not have to be fixed, so that the stress during the examination is reduced for the animal T and a faster, more accurate, more reliable and for the animal T as pleasant as possible examination, in particular blood pressure determination, can be realized.

The sensor device 4 preferably has more than 30, in particular more than 60, and/or less than 500, preferably less than 200, more preferred less than 100, in particular less than 100, particularly preferably about 80, emitters 5.

Preferably, the sensor device 4 has more than 20, preferably more than 40, and/or less than 500, preferably less than 200, in particular less than 100, particularly preferably about 60, detectors 6.

Preferably, the number of sensors 7 corresponds to the number of detectors 6, since preferably a detector 6 with several emitters 5 forms a sensor 7. However, if an emitter 5 with several detectors 6 forms a sensor 7, the number of sensors 7 preferably corresponds to the number of emitters 5.

The sensor device 4 and/or matrix of emitters 5 and detectors 6 preferably has an area of more than 10 cm², in particular more than 20 cm², particularly preferably more than 30 cm², very particularly preferably more than 40 cm², and/or less than 200 cm², preferably less than 150 cm², more preferably less than 100 cm², particularly less than 80 cm².

Preferably, an area density of the emitters 5, an area density of the detectors 6, an area density of the sensors 7 and/or a common area density of the emitters 5 and detectors 6 is more than 0.5/cm², preferably more than 1/cm², in particular more than 2/cm², and/or less than 40/cm², preferably less than 20/cm², in particular less than 10/cm². Herein, the number of emitters 5 and/or detectors 6 and/or sensors 7 per area is in particular denoted as area density.

The number, arrangement, area and/or area density of the sensor device 4, emitters 5, detectors 6 and/or sensors 7 preferably allow a reliable and accurate examination, in particular photoplethysmography and/or determination of blood pressure BP, to be performed without fixation of the paw 2 of the animal T relative to an examination means such as a sensor, so that the animal T can preferably move freely relative to the sensor device 4 during the examination. This makes the examination particularly pleasant and stress-free for the animal T, which improves the measuring accuracy.

The emitters 5 and/or detectors 6 are preferably each divided into several groups or preferably form several groups, which are in particular separately from each other and/or separately connected.

Preferably, the emitters 5 are divided into two groups and/or the emitters 5 form two groups.

Preferably, the detectors 6 are divided into five groups and/or the detectors 6 form five groups.

The emitters 5 within a group and/or the detectors 6 within a group are preferably connected or interconnected serially.

Figure 5:
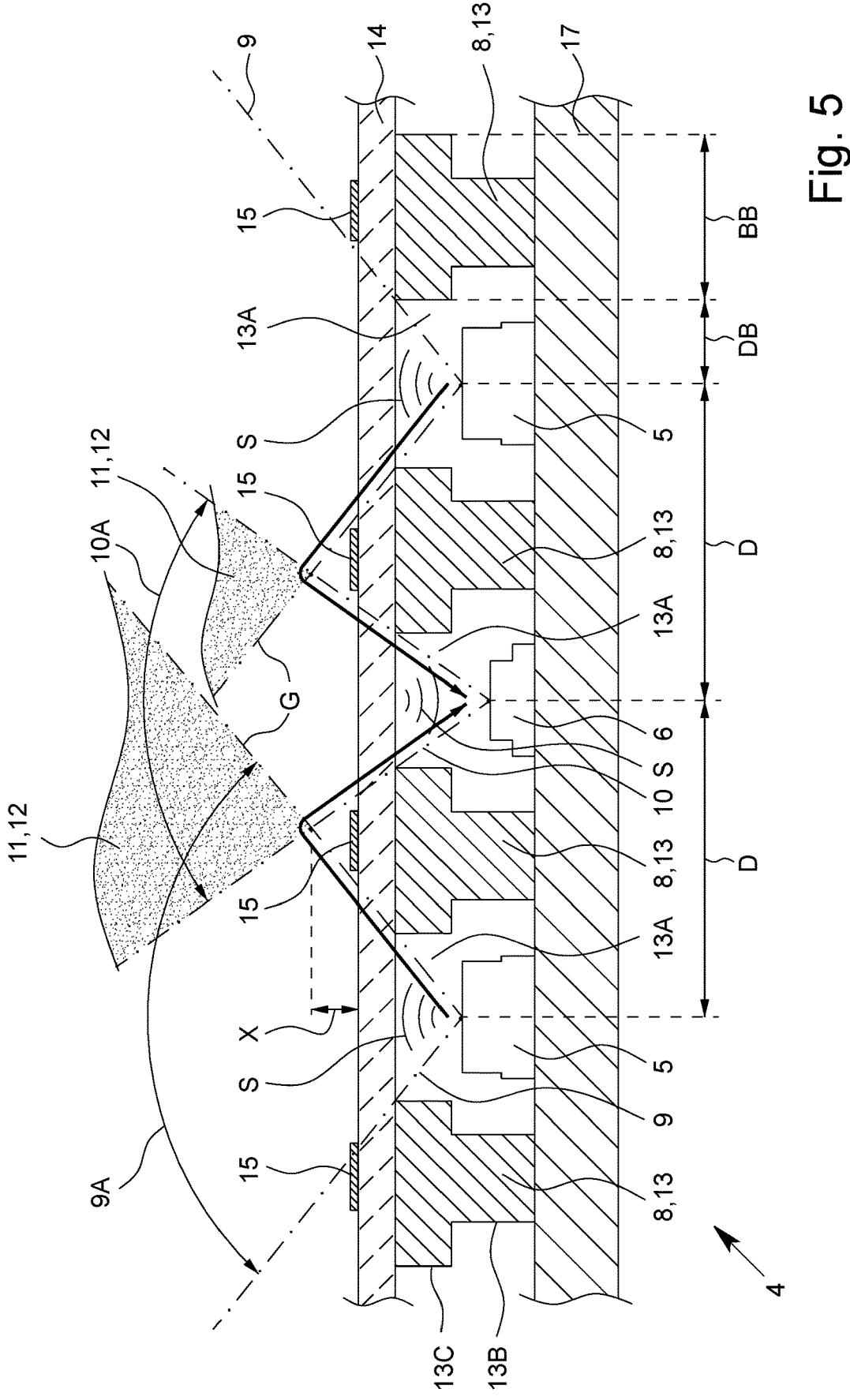
FIG. 5 is a schematic sectional view through the sensor
device.

FIG. 5 shows a schematic section through the sensor device 4.

Figure 6:
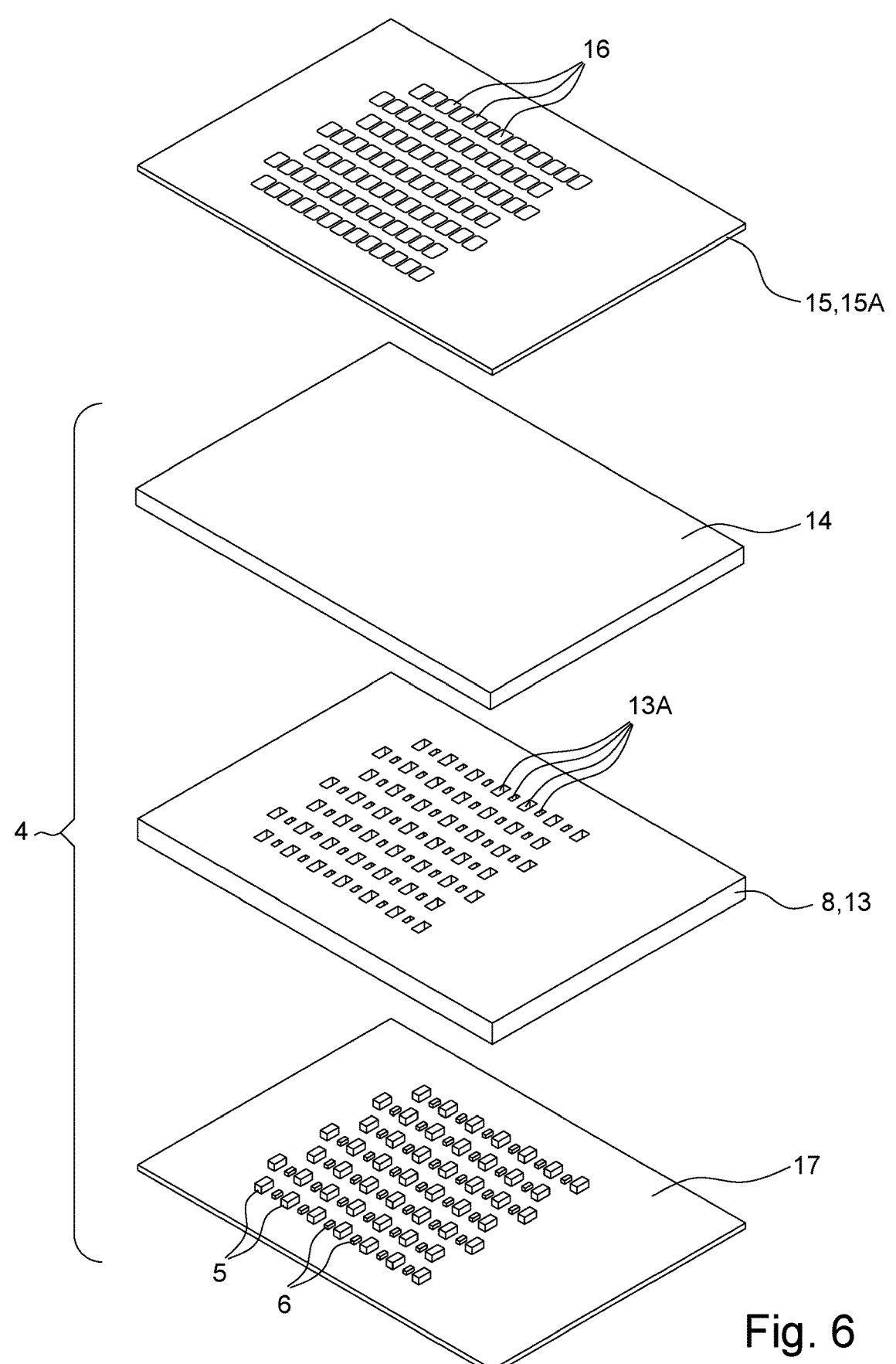
FIG. 6 is a schematic exploded view of the sensor device
with an electrode arranged thereon.

FIG. 6 shows the sensor device 4 in a schematic exploded view.

The sensor device 4 preferably has a limiting device 8.

At this point, it should be noted that the limiting device 8 as well as the associated features and advantages are in principle realizable independently of the above described design of the sensor device 4. In particular, the limiting device 8 can also be advantageous for a sensor device 4 with exactly one emitter 5 and exactly one detector 6. Consequently, the terms "emitter" and "detector" are preferably used in the singular in the following. Of course, the explanations also apply to designs of the sensor device 4 with several emitters 5 and/or several detectors 6, in particular to a sensor device 4 designed as described above.

The limiting device 8 is preferably designed to determine, define and/or limit an emission region 9 of the emitter 5, a detection region 10 of the detector 6, a sensor region 11 of the sensor 7 and/or a sensing region 12 of the sensor device 4. In particular, the limiting device 8 is designed as an aperture for the emitter 5 and/or detector 6.

For this purpose, the limiting device 8 in the illustration example has a barrier 13 described in more detail below or is formed hereby. Alternatively, or additionally, however, the limiting device 8 can also have one or more lenses not shown, in particular converging lenses, which lead to a corresponding limitation of an emission region 9 and/or detection region 10, in particular by focusing radiation R.

The emission region 9 of an emitter 5 is generally the range into which radiation R can be emitted by the emitter 5. For example, the emission region 9 of an emitter 5 can be at least essentially conical and/or defined by one or—in particular in the case of a non-conical emission region 9—several emission angle(s) 9A.

The detection region 10 of a detector 6 is generally the range from which radiation R can reach the detector 6 and/or from which radiation R can be detected with the detector 6. For example, the detection region 10 of a detector 6 can be at least essentially conical and/or defined by one or—in particular in the case of a non-conical detection region 10—several detection angle(s) 10A.

Preferably, the emitter 5 and/or the detector 6 naturally have a certain emission region 9 or detection region 10, respectively. Preferably, this natural emission region 9 and/or detection region 10 is limited or restricted by the limiting device 8 or the limiting device 8 is designed for this purpose. Therefore, the terms "emission region" and "detection region" in the sense of the present invention preferably refer to the emission region 9 or detection region 10 defined or limited by the limiting device 8 and not to the natural emission region 9 or detection region 10 of the emitter 5 or detector 6 per se.

The emission region 9 is indicated in FIG. 5 by the V-shaped dotted lines starting from the emitter 5. The dotted lines represent the border of the emission region 9, which is in particular defined by the limiting device 8. In particular, the emission region 9 is the area enclosed or limited by the lines.

The detection region 10 is indicated in FIG. 5 by the V-shaped dotted lines starting from the detector 6. The dotted lines represent the border of the detection region 10, which is in particular defined the limiting device 8. In particular, the detection region 10 is the area enclosed or limited by the lines.

The emission region 9 of an emitter 5 is preferably limited by (imaginary) lines, in particular those shown in FIG. 5 as dash-dotted lines, which represent the ray path of the outermost rays of a beam of rays that can leave the sensor device 4 starting from a center point or geometric center of an emission area of the emitter 5. In particular, the lines represent an edge or a border of the emission region 9. In particular, the emission region 9 is the region enclosed or limited by the lines.

In case the limiting device 8 is realized by a barrier 13, as shown in FIG. 5, these outermost beams are those beams that are not blocked by the limiting device 8 starting from the center point or geometric center, so that the lines representing these beams in FIG. 5 touch an edge or corner of the limiting device 8 or barrier 13.

If the limiting device 8 has, or is formed by, a lens as an alternative or in addition to the barrier 13, these outermost rays are those rays that pass through the outermost edge of the lens from the center point or geometric center of an emission surface of the emitter 5.

The detection region 10 of a detector 6 is preferably limited by (imaginary) lines, in particular those shown in FIG. 5 as dash-dotted lines, which represent the optical path of the outermost rays of a beam of rays that can reach a detection surface of the detector 6, in particular a center point or geometric center thereof, from outside the sensor device 4. In particular, the lines represent an edge or a border of the detection region 10. In particular, the detection region 10 is the region enclosed or limited by the lines.

In case the limiting device 8 is realized by a barrier 13, as shown in FIG. 5, these outermost rays are those rays that are not blocked by the limiting device 8 and thus can reach the center point or geometric center of the detection surface of the detector 6, so that the lines in FIG. 5 representing these rays touch a rim or edge or corner of the limiting device 8 or barrier 13.

If the limiting device 8 has or is formed by a lens as an alternative or in addition to the barrier 13, these outermost rays are those rays that can pass through the outermost edge of the lens from outside the sensor device 4 and reach the center point or geometric center of the detection surface of the detector 6.

The emission angle 9A is preferably the angle between the (imaginary, in particular outside the sensor device 4 running) lines, which represent the borders of the emission region 9. This is in particular shown in FIG. 5.

Preferably, the detection angle 10A is the angle between the (imaginary, in particular outside the sensor device 4 running) lines that represent the borders of the detection region 10. This is in particular shown in FIG. 5.

In the above definition of the emission region 9 and detection region 10, an idealized approach was chosen, with reference being made to a center point or geometric center of an emission area or detection area, which in reality deviates from a point shape and forms an—albeit very small—extended area. This makes it possible that in reality radiation R from the emitter 5 can also reach an area outside the emission region 9 as defined above and/or radiation R from outside the detection region 10 as defined above can reach the detector 6, in particular scattered light. However, the above definitions of emission region 9 and detection region 10 remain unaffected by this. Furthermore, the emission region 9 and detection region 10 as defined above also represent in reality the region into which the vast majority of the radiation R emitted by the emitter 5 is emitted and/or from which radiation R can reach the detector 6.

The sensor region 11 of a sensor 7 is generally the region that can be examined or sensed with the sensor 7. Preferably, only objects located in sensor region 11 can be examined by means of sensor 7. In particular, the sensor region 11 of a sensor 7 is the region in which the emission region(s) 9 of the emitter(s) 5 of the sensor 7 and the detection region(s) 10 of the detector(s) 6 of the sensor 7 overlap.

In FIG. 5, by way of example, arrows indicate how radiation R can pass from an emitter 5 to a detector 6. The arrows very schematically show the path of a light beam which is emitted by the emitter 5, reaches a detection region 10 and thus a region where the emission region 9 and the detection region 10 overlap, and is scattered or reflected there in the direction of detector 6 by an object not shown and in this way reaches the detector 6.

In principle, it is possible that, deviating from the idealized view chosen here, in reality objects outside the sensor region 11 as defined above are at least partially detected or detectable by a sensor 7. On the one hand, this can take place by the fact that, as already described above, a small amount of radiation R in reality can also reach a region outside the defined emission region 9 and/or radiation R from outside the defined detection region 10 can also reach the detector 6. On the other hand, however, it can also happen, for example in case of multiple scattering in an object, that an object or a part of an object is detected with a sensor 7 which is located outside the defined sensor region 11.

The sensing region 12 of the sensor device 4 is the range which can be examined and/or detected/sensed with the sensor device 4. In particular, the sensing region 12 comprises the emission regions 9, detection regions 10 and/or sensor regions 11 or is formed thereby.

Preferably, the sensing region 12 is the total/entirety of the sensor regions 11 of the sensors 7 of the sensor device 4.

The sensing region 12 can be formed by a continuous/connected region. This is the case if the sensor regions 11 of the sensors 7 of the sensor device 4 overlap.

However, it is also possible that the sensing region 12 is not connected or is formed by separate or non-connected regions or sensor regions 11. This is the case if at least some of the sensor regions 11 of the sensors 7 do not overlap with other sensor regions 11.

The sensing region 12 preferably has a border G. The border G is preferably formed by the edge or the entirety of the edges of the sensor regions 11. The border G is in particular a point or a line where an emission region 9 and a detection region 10 intersect. This is in particular shown in FIG. 5.

The sensing region 12 and/or its border G preferably has a distance X from the sensor device 4. In particular, a (minimum) penetration depth of the radiation R emitted by the emitters 5 and/or detected by the detectors 6 into the paw 2 during the examination can be achieved or ensured. In particular, this minimum penetration depth or distance X prevents light reflected or scattered from a surface of the paw 2 from reaching the detector 6. This improves the accuracy and reliability of the examination, in particular the determination of blood pressure.

The distance X is preferably a minimum distance of the sensing region 12 or its border G from the sensor device 4. Preferably, the border G of the sensing region 12 does not run straight or parallel to the sensor device 4, as can be seen in particular from FIG. 5. In the sectional view as shown in FIG. 5, the border G runs particularly zigzag. This is particularly due to the fact that the sensor regions 11 of the sensors 23 preferably increase (in section) in a V-shape with increasing distance from the sensor device 4. Consequently, the sensing region 12 preferably has different distances from the sensor device 4 at different positions of the sensor device 4, wherein the distance X is the smallest of these different distances.

The limiting device 8 is preferably designed such that the distance X of the border G of the sensing region 12 from the sensor device 4 is more than 0.5 mm, preferably more than 1 mm, and/or less than 10 mm, preferably less than 5 mm, in particular less than 3 mm.

The limiting device 8 preferably limits—in particular in the sectional plane shown in FIG. 5—an emission angle 9A of the emitter 5 and/or a detection angle 10A of the detector 6 to less than 90°, preferably less than 75°, in particular about 60°. The sectional plane shown in FIG. 5 is perpendicular to the plane defined by the matrix of emitters 5 and detectors 6 and intersects the emitters 5 and detectors 6 along a row or column of the matrix.

The limiting device 8 is preferably formed by one or more barriers 13. The barrier 13 is arranged between an emitter 5 and a detector 6. Preferably, a barrier 13 is arranged between each detector 6 and the respective adjacent emitters 5.

The barrier 13 is impermeable to the radiation R emitted by the emitter 5, in particular to infrared radiation.

The barrier 13 is preferably arranged or designed in such a way that the above-mentioned distance X of the border G of the detection range 8 from the sensor device 4 is reached or realized.

The dimensions of the limiting device 8 or barrier 13, in particular its height HB and/or width BB, as well as the distance DB of the limiting device 8 or barrier 13 from the emitter 5 and the detector 6 and the distance D of the emitter 5 from the detector 6 are preferably matched to each other in such a way that the emission region 9 of the emitter 5 and the detection region 10 of the detector 6 overlap in such a way that the above-mentioned distance X of the border G of the sensing region 12 from the sensor device 4 and/or the above-mentioned emission angle 9A and/or detection angle 10A is/are reached or realized.

Preferably, the barrier 13 fulfills several functions and/or has several sections 13B, 13C, which in particular realize these functions.

A function of the barrier 13 is preferably the shielding of the emitter 5 from the detector 6, in particular in such a way that no radiation R emitted by the emitter 5 can reach the detector 6 directly or without intermediate scattering and/or reflection. For this purpose, the barrier 13 preferably has a shielding section 13B. The shielding section 13B is therefore preferably designed to shield the detector 6 from the emitter 5 or to prevent direct crosstalk from the emitter 5 to the detector 6. The shielding section 13B is preferably located between the emitter 5 and the detector 6. The shielding section 13B preferably runs at least substantially parallel to a main emission direction of the emitter 5 and/or transversely, in particular at least substantially perpendicular, to the plane formed by the emitters 5 and detectors 6.

Another function of the barrier 13 is preferably, as already mentioned above, to limit the emission region 9, detection region 10, sensor region 11 and/or sensing region 12. In other words, the barrier 13 and/or a section thereof preferably represents an aperture for the emitter 5 and/or the detector 6. For this purpose, the barrier 13 preferably has an aperture section 13C. The aperture section 13C is preferably designed and/or arranged in such a way that the emission region 9 of the emitter 5 and/or the detection region 10 of the detector 6 is limited or restricted, in particular in the manner described above. The aperture section 13C preferably forms an aperture. In particular, the aperture section 13C preferably runs transversely, preferably at least substantially perpendicularly, to the main emission direction of the emitter 5 and/or at least substantially parallel to the plane formed by the emitters 5 and detectors 6.

The shielding section 13B and the aperture section 13C are preferably designed in one piece and/or formed by different sections of the same component. In particular, the aperture section 13C can be wider than the shielding section 13B, resulting in a T-shaped cross-section of the barrier 13, as shown in FIG. 5. However, this is not mandatory.

The limiting device 8 and/or barrier 13, in particular the aperture section 13C, preferably has a width BB of more than 1 mm, in particular more than 2 mm, and/or less than 5 mm, in particular less than 4 mm. Furthermore, the limiting device 8 and/or barrier 13 preferably has a height HB of more than 1 mm, preferably more than 2 mm, and/or less than 5 mm, in particular less than 4 mm.

Preferably, the barriers 13 form or limit areas 13A that are transparent and/or translucent for the radiation R emitted by the emitters 5 and/or detected by the detectors 6. These transparent areas 13A are each arranged corresponding to the emitters 5 and detectors 6, so that they are located in the sensor device 4 above the emitters 5 and detectors 6, respectively, and the material located between the transparent areas 13A or surrounding the transparent areas 13A forms the limiting device 8 and/or the barriers 13. This is shown as an example in FIGS. 5 and 6.

The examination apparatus 1 and/or sensor device 4 preferably has a barrier element 13D. Preferably, the barrier element 13D has or forms the barrier 13 or barriers 13.

The barrier element 13D is preferably a one-piece, in particular flat and/or plate-like, part having the transparent areas 13A.

The transparent areas 13A are preferably formed by through holes of the barrier element 13D. In principle, however, it is alternatively or additionally possible that the transparent areas 13A are formed by or comprise a material that is transparent for the radiation R emitted by the emitters 5 and/or detected by the detectors 6, for example glass, plexiglass or the like.

The limiting device 8 and/or barriers 13 and/or the barrier element 13D and/or the transparent areas 13A preferably form a grid or grating corresponding to the emitters 5 and/or detectors 6, in particular a grating aperture.

Preferably, the sensor device 4 has a cover 14 which is transparent for the radiation R emitted by the emitter 5 and/or detected by the detector 6. The cover 14 can be made of glass, plexiglass, a transparent plastic or the like.

Preferably, the cover 14 covers the sensor device 4 completely, continuously and/or gaplessly.

The cover 14 is preferably designed to protect the sensor device 4 and/or the emitters 5 and/or detectors 6 from soiling and/or damage. The cover 14 preferably forms or has an at least substantially flat and/or even, in particular smooth, surface to support the paw 2.

Particularly preferably, the distance X of the border G of the sensing region 12 from the sensor device 4 is or corresponds to the distance of the border G of the detection zone 12 from the cover 14, in particular the distance from the side of the cover 14 facing away from the emitter 5 and/or detector 6.

Preferably, the examination apparatus 1 has one or more detection elements for detecting activity of the heart of the animal T, in particular for recording a cardiogram KG.

The cardiogram KG preferably represents an activity of the heart, in particular of the animal T to be examined by means of the examination apparatus 1, and/or comprises information about the activity of the heart.

Figure 9:
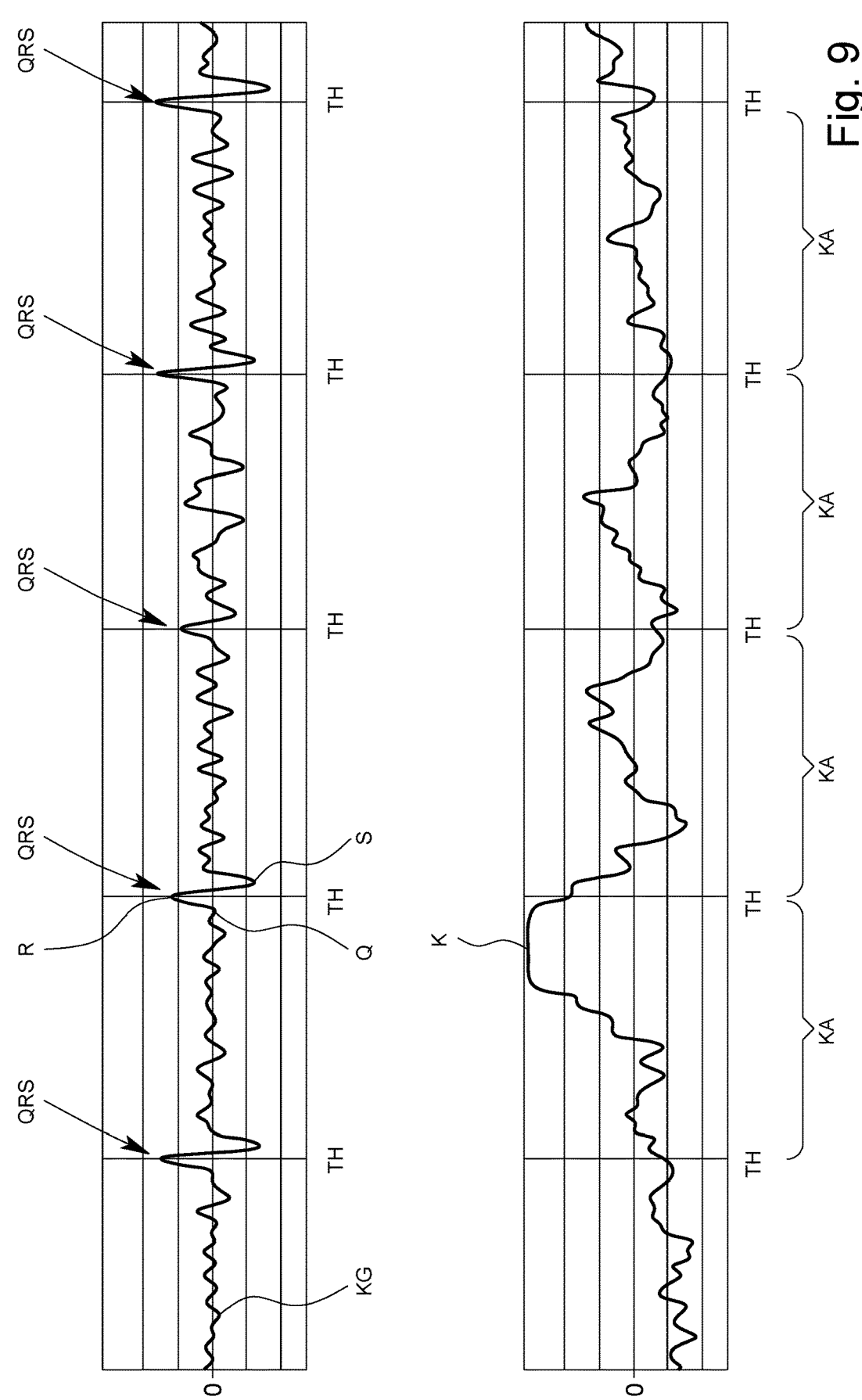
FIG. 9 is a schematic representation of a cardiogram and
a curve comprising information about arterial blood flow.

FIG. 9 shows an example of a cardiogram KG.

In particular, the heartbeats or the times at which heartbeats can be read or derived or determined from the cardiogram KG.

The cardiogram KG is preferably an electrocardiogram. In principle, however, the cardiogram KG can also be an impedance cardiogram, a phonocardiogram, a ballistocardiogram or the like.

The detection elements are preferably formed by electrodes 15. In principle, however, the detection element(s) can also be formed by or have one or more microphones or other sound sensors or the like.

Preferably, the examination apparatus 1 thus has at least one electrode 15, preferably at least two electrodes 15. In the illustration example, the examination apparatus 1 has three electrodes 15. In principle, however, the examination apparatus 1 can also have a significantly larger number of electrodes 15.

Preferably, a cardiogram KG can be recorded by means of the electrodes 15 and/or the electrodes 15 are designed to record a cardiogram KG, in particular wherein the cardiogram KG is an electrocardiogram.

The electrodes 15 are preferably flat and/or laminar. In particular, the electrodes 15 consist of or have an electrically conductive material.

Preferably, at least one of the electrodes 15 is designed as a tissue electrode. This is indicated schematically in FIG. 1 by hatching of electrodes 15. Preferably, all electrodes 15 are designed as fabric electrodes. This has proven to be particularly advantageous for the examination of animals T such as cats or dogs, since hereby the examination can be made particularly pleasant for the animals T. In particular, it has turned out that animals T are easily irritated by metallic and/or shiny surfaces, which can be avoided by using tissue electrodes.

The at least two electrodes 15 are denoted below as first electrode A and second electrode 15B for better differentiation. The electrodes 15A and 15B can be identical or have different designs.

Explanations with reference to the first electrode 15A therefore preferably also apply to the second electrode 15B and vice versa.

Preferably, the electrodes 15A, 15B are each designed to contact a paw 2 of the animal T. Particularly preferably, the first electrode 15A is designed for contacting the left forepaw and the second electrode 15B is designed for contacting the right forepaw.

Optionally, the examination apparatus 1 has a third electrode 15C. The third electrode 15C is preferably designed as reference electrode or collection electrode. The third electrode 15C is preferably designed to simultaneously contact several parts of the body of the animal T to be examined, in particular several paws 2, in particular the two hindpaws of the animal T.

The electrodes 15 are preferably arranged in such a way that when the animal T is placed on the examination apparatus 1, in particular in a position natural for the animal T, such as a sitting or lying position, one paw 2 of the animal T contacts one of the electrodes 15. In this way, the examination can be made particularly pleasant for the animal T.

The arrangement, size and design of the electrodes 15 are preferably adapted to the anatomy of the animal T to be examined, in particular a domestic cat, so that the examination can take place in a natural, preferably pleasant, position for the animal T and/or the animal T can move freely relative to the electrodes 15 during the examination.

The electrodes 15, in particular the first electrode 15A and the second electrode 15B, are preferably arranged at a distance DE of more than 2 cm, in particular more than 5 cm, and/or less than 25 cm, in particular less than 20 cm, particularly preferably less than 15 cm, very particularly preferably about 10 cm.

The distance DE between two electrodes 15 is referred to in particular as the distance DE between the center points or geometric centers of the electrodes 15 or their surface. This is shown schematically in FIG. 1.

The distance DE of the electrodes 15, in particular of the first electrode 15A from the second electrode 15B, is preferably fixed and/or not variable.

The (respective) electrode 15A, 15B preferably has an area of more than 10 cm$^2$, in particular more than 15 cm$^2$, and/or less than 100 cm$^2$, in particular less than 80 cm$^2$, particularly preferably less than 50 cm$^2$.

The third electrode 15C preferably has an area of more than 50 cm$^2$, in particular more than 100 cm$^2$, and/or less than 1000 cm$^2$, preferably less than 500 cm$^2$, in particular less than 200 cm$^2$.

The third electrode 15C preferably has a larger area than the first and/or second electrode 15A, 15B, in particular more than double or triple, particularly preferably more than four times, the area of the first and/or second electrode 15A, 15B.

Preferably, the first electrode 15A is arranged in such a way that, at a paw 2, in particular the left or right forepaw, a cardiogram KG can be recorded by means of the first electrode 15A and, simultaneously, the optical examination can be performed and/or the curve K, in particular a photoplethysmogram (PPG), can be recorded by means of the sensor device 4.

FIG. 7 shows by way of example a paw 2 that is positioned in such a way that a cardiogram KG can be recorded by means of the first electrode 15A and, simultaneously, the optical examination can be performed and/or the curve K can be recorded by means of the sensor device 4.

The first electrode 15A is preferably designed as tissue electrode.

A tissue electrode is preferably an electrode that has or is formed by a tissue. In particular, in the case of a tissue electrode, a contact surface for contact with a body part, in particular the paw 2, has a tissue or is formed hereby. The tissue is preferably a conductive tissue, for example a tissue in which conductive threads are incorporated and/or a tissue coated with a conductive layer.

The first electrode 15A is preferably arranged on the sensor device 4 and/or on the cover 14, particularly preferably on the side of the cover 14 facing away from the emitter 5 and detector 6. This is in particular shown in FIGS. 5 to 7.

The first electrode 15A is preferably arranged (only) between the emitter 5 and the detector 6 and/or opposite the barrier 13 in a projection perpendicular to the cover 14 and/or to the plane formed by the emitters 5 and detectors 6. Alternatively, or additionally, the electrode 15A is transparent for the radiation R emitted by the emitter 5. Hereby, the optical examination of the animal T and/or the paw 2 by means of the sensor device 4 is not affected by the first electrode 15A.

The first electrode 15A preferably has areas 16 that are transparent to the radiation R emitted by the emitters 5 and/or detected by the detectors 6. These transparent areas 16 are arranged corresponding to the emitters 5 and detectors 6, so that they are located (in a projection perpendicular to the plane of the emitters 5 and/or detectors 6 and/or to the cover 14) above the emitters 5 and detectors 6, respectively. This is in particular shown in FIGS. 5 and 6.

The transparent areas 16 of the first electrode 15A are preferably formed by through holes of the electrode 15A. In principle, it is alternatively or additionally possible that the transparent areas 16 or the entire first electrode 15A are formed by or comprise a material that is transparent for the radiation R emitted by the emitters 5 and/or detected by the detectors 6.

The first electrode 15A and/or the transparent areas 16 preferably form a grating or grid corresponding to the emitters 5 and/or detectors 6.

Optionally, the examination apparatus 1 has a positioning aid 24. The positioning aid 24 is designed to support correct positioning of the animal T or the paw 2 for examination. In particular, the positioning aid 24 is designed to indicate or mark an area for positioning a paw 2 or several paws 2, in particular the left forepaw and/or the right forepaw. The positioning aid 24 is preferably arranged near the sensor device 4 and/or preferably surrounds the sensor device 4. Alternatively, or additionally, the position of one or more of the electrodes 15 can be indicated by the positioning aid 24.

The positioning aid 24 is preferably formed by an elevation or recess of the examination apparatus 1 and/or rest surface 3. The positioning aid 24 can, for example, be funnel-like or have the shape of a funnel.

However, the positioning aid 24 is only optional and not mandatory.

The examination apparatus 1 preferably has a circuit board 17, in particular a printed circuit board (PCB).

Preferably, the circuit board 17 carries the sensor device 4 and/or the sensor device 4 is located on the circuit board 17.

Preferably, the circuit board 17 carries the first and/or second electrode 15A, 15B or the first and/or second electrode 15A, 15B are arranged on the circuit board 17. Optionally, the circuit board 17 carries additionally also the third electrode 15C and/or the third electrode 15C is also arranged on the circuit board 17.

The circuit board 17 preferably has or forms peripherals and/or electrical lines required for the operation of the sensor device 4, in particular the emitters 5 and/or detectors 6 and/or sensors 7, and/or the electrodes 15A, 15B and/or for the evaluation of the signals measured by the detectors 6 and/or electrodes 15.

The examination apparatus 1 preferably has a scale 18. The scale 18 is preferably an electronic scale 18.

The scale 18 is preferably designed for weighing an animal T positioned or placed on the examination apparatus 1.

The examination apparatus 1 and/or scale 18 is preferably designed for a body fat measurement, i.e., for determining the body fat percentage of the animal T on the scale 18. The body fat measurement or determination of the body fat percentage is preferably carried out via a bioimpedance measurement. In particular, two or more of the electrodes 15, 15A, 15B, 15C can be used for this purpose.

The examination apparatus 1 preferably has a force sensor 18A. The force sensor 18A is preferably designed to measure or detect a force, in particular a weight force, exerted by the animal T on the examination apparatus 1.

The force sensor 18A can form part of the scale 18 or be integrated into the scale 18, but can also be provided as an alternative or in addition to the scale 18.

The force sensor 18A can, for example, be designed as a piezo element or strain gauge or the like.

The examination apparatus 1 can also have several force sensors 18A, in particular of the same kind or type. Preferably, one or more force sensors 18A are arranged under the sensor device 4 or the sensor devices 4, under the rest surface 3 and/or under the electrodes 15 (each) and/or the force sensors 18A are integrated into the sensor device(s) 4 and/or rest surface 3 and/or electrodes 15. In particular, the force sensor 18A can be designed by such an arrangement to determine a presence and/or positioning of the animal T and/or to support such a determination.

The examination apparatus 1 preferably has a display device 19. The display device 19 is in particular designed for optical display. The display device 19 is preferably formed by a display, e.g., an LCD display, an LED display, an OLED display or the like.

The display device 19 is preferably designed to display values measured or determined by means of the examination apparatus 1, such as a cardiogram KG, a heart rate, a blood pressure BP, a weight, a body fat percentage or the like. In particular, the display of a blood pressure BP and a cardiogram KG by means of the display device 19 are shown schematically in FIG. 1.

Alternatively, or additionally, the display device 19 can be designed for user guidance, e.g., to display instructions for the operation or use of the examination apparatus 1, selection menus, error messages, warning messages or the like.

Furthermore, the examination apparatus 1 preferably has an input device 20. The input device 20 is preferably designed for making settings and/or adjustments and/or for controlling the examination apparatus 1. The input device 20 is preferably arranged in the immediate vicinity of the display device 19 and/or integrated into the display device 19.

For example, the input device 20 can be formed by one or more keys, buttons, switches, or the like. However, the display device 19 is particularly preferably designed as a touch display or touch-sensitive display, so that the display device 19 has or forms the input device 20 and/or the input device 20 is integrated into the display device 19.

The examination apparatus 1 preferably has a power supply device 21. The power supply device 21 is designed to supply the examination apparatus 1 with electrical energy.

Preferably, the power supply device 21 has an energy storage device for storing electrical energy, for example an accumulator, a battery or the like. In particular, the power supply device 21 is designed for charging the accumulator or battery, particularly preferably for inductive charging. For this purpose, the power supply device 21 preferably has a corresponding charging device. Alternatively, or additionally, the power supply device 21 can also have or form a connection for connecting the power supply device 21 to an external power supply, e.g., the mains. In particular, the connection can comprise or form the charging device or a part thereof.

The examination apparatus 1 preferably has a control device 25 for controlling the examination apparatus 1 and/or the examination. The control device 25 is preferably formed by a processor P and/or preferably has a processor P. The processor P is preferably a microprocessor. The control device 25 and/or the processor P is/are preferably designed to control the sensor device 4, in particular the emitters 5, detectors 6 and/or sensors 7, to control the electrodes 15 and/or to control the scale 18.

Accordingly, the control device 25 is preferably coupled with the sensor device 4, the emitters 5, the detectors 6, the sensors 7, the electrodes 15, the scale 18 and/or the force sensor 18A.

Furthermore, the power supply device 21 is preferably designed to supply power to the control device 25. In particular, the control device 25 is coupled to the power supply device 21.

The control device 25 is preferably designed to control the display device 19 and/or coupled to the display device 19. Preferably, the control device 25 is coupled to the input device 20 and/or can be operated by means of the input device 20.

The control device 25 is preferably designed for processing and/or forwarding the signals measured by the sensor device 4 and/or the electrodes 15.

The examination apparatus 1 preferably has a memory and/or a storage medium 26 for data storage. Preferably, the storage medium 26 is coupled with the control device 25. In particular, the storage medium 26 is designed for at least temporary storage of signals measured by the sensor device 4 and/or the electrodes 15.

The storage medium 26 can have several separate components and/or be formed hereby.

Preferably, the storage medium 26 has one or more permanently installed memory modules and/or storage elements, for example a hard disk (HDD), a solid-state drive (SSD), a RAM module and/or a flash memory or the like.

Alternatively, or additionally, the storage medium 26 may have or be formed by one or more storage elements that are separate from and/or connectable to the examination apparatus 1, such as a USB stick or the like.

In principle, the storage medium 26 may be formed by or comprise one or more arbitrary storage devices for storing electronic data, such as CD-ROMs, hard disks, USB sticks, flash memory, cloud memory, external databases or other computer equipment separate from the examination apparatus 1 or external thereto and/or mobile end devices with an integrated memory, such as PCs, data centers, supercomputers, cloud computers, servers, cell phones, smart phones, tablets, laptops or the like.

The examination apparatus 1 is preferably designed for the analysis and/or evaluation of the signals measured with the electrodes 15, the sensor device 4 and/or the scale 18. The evaluation of the signals is preferably performed by means of the control device 25 and/or the processor P and/or is controlled hereby, in particular by using the storage medium 26.

The examination apparatus 1 preferably has an interface device 22 for connecting the examination apparatus 1 with one or more external devices 23. The interface device 22 may have several, in particular different, interfaces. The interfaces can be wired or wireless interfaces. For example, the interface device can have one or more serial interfaces, one or more USB interfaces, one or more HDMI interfaces and/or some or more other interfaces, which are in particular designed for (in particular wired) data exchange between the external device 23 and the examination apparatus 1. Alternatively, or additionally, the interface device 22 may also have one or more wireless interfaces, such as WiFi interfaces, Bluetooth interfaces, in particular Bluetooth Low Energy Interfaces (BLE interfaces), NFC interfaces or the like.

In other words, the examination apparatus 1 is preferably designed for data exchange with an external device 23, in particular by means of the interface device 22.

The examination apparatus 1 is preferably designed to transmit the data or signals measured with the sensor device 4 and/or the electrodes 15 and/or the results or evaluations determined on the basis of these data or signals to the external device 23, in particular by means of the interface device 22.

The external device 23 is preferably a device that is separate, in particular physically separate, from the examination apparatus 1.

The external device 23 may be designed to control the examination apparatus 1 and/or to record and/or evaluate and/or analyze and/or display or otherwise output signals and/or data measured by the examination apparatus 1 and/or results transmitted by the examination apparatus 1. Preferably, the external device 23 is designed to display a cardiogram KG and/or a blood pressure BP, as shown schematically in FIG. 8.

The external device 23 is preferably designed as a mobile end device, for example a smartphone, tablet or laptop, and/or as a PC, server, computer network, cloud, Internet portal, app and/or other computer device.

Alternatively, or additionally, the external device 23 is designed as a storage medium 26 such as a memory stick. In particular, the external device 23 can form or have the storage medium 26 or a part thereof.

Preferably, the examination apparatus 1 has the external device 23 or the external device 23 forms a part of the examination apparatus 1 or the external device 23 is assigned to the examination apparatus 1.

Preferably, evaluation of the signals measured by the examination apparatus 1, in particular by the sensor device 4 and/or the electrodes 15, 15A, 15B, 15C, is performed in or by the examination apparatus 1 itself. Alternatively, or additionally, the evaluation or parts thereof can also take place outside the examination apparatus 1 and/or by means of the external device 23.

Figure 8:
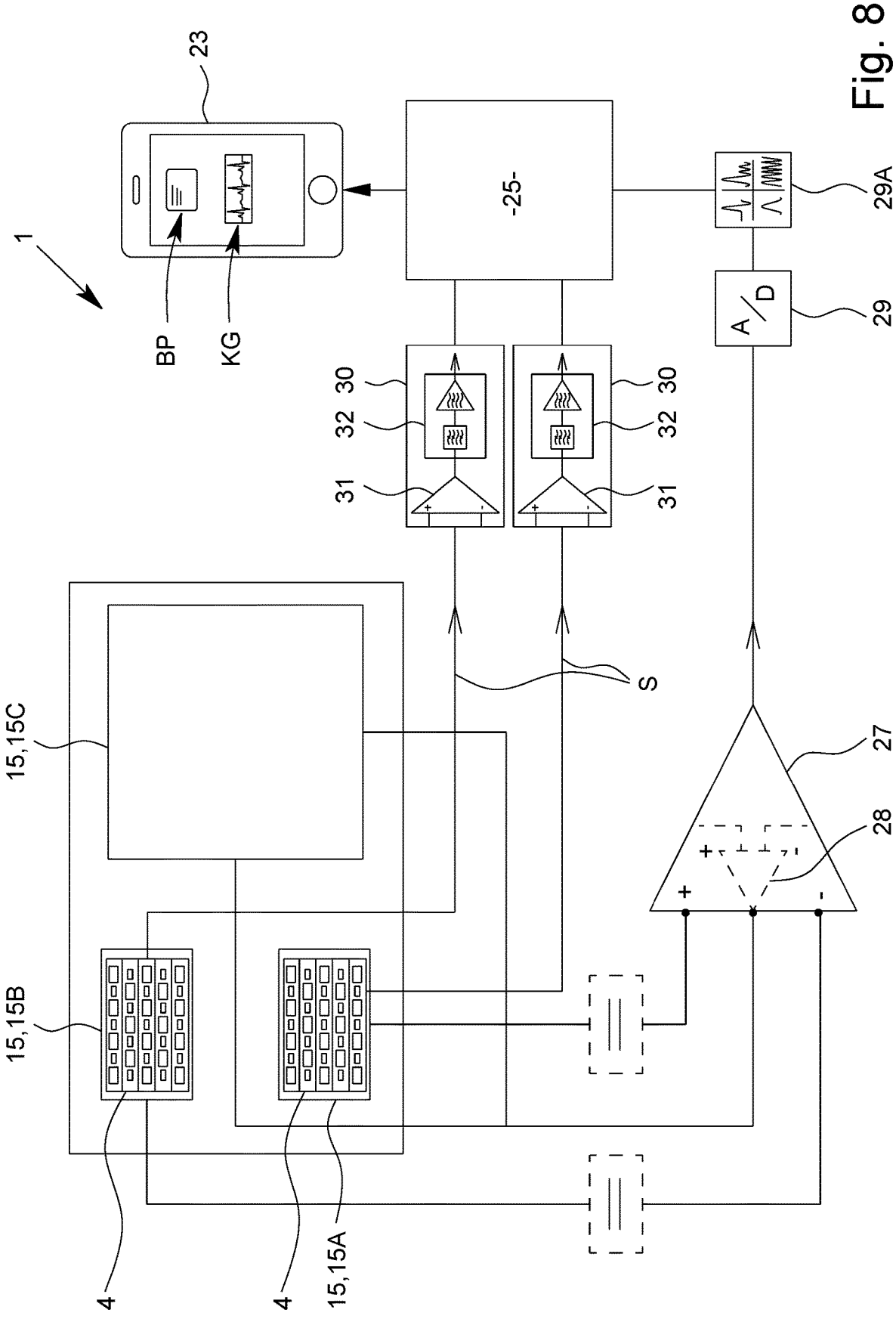
FIG. 8 is a schematic, block diagram-like representation
of the examination apparatus.

In FIG. 8, a wiring of the electrodes 15 as well as a processing of the signals measured by the sensor device(s) 4 and the electrodes 15 are shown in a schematic, block diagram-like representation.

The examination apparatus 1 preferably has a preprocessing device 27. The preprocessing device 27 preferably has or is formed by an amplifier, in particular a differential amplifier. The differential amplifier is particularly preferably formed by an operational amplifier or has such an amplifier. However, other solutions are also possible.

The preprocessing device 27 is preferably coupled or connected to the electrodes 15 and is in particular designed for preprocessing the signals measured by the electrodes 15, 15A, 15B, 15C. In particular, the preprocessing device 27 is designed to amplify the difference between signals measured with different electrodes 15, in particular voltages such as biopotentials, particularly preferably to amplify the difference between the signal measured with the first electrode 15A and the signal measured with the second electrode 15B.

Optionally, the electrodes 15 are coupled to the preprocessing device 27 via a capacitance or a capacitor. This is indicated in FIG. 8 by the capacitance symbols in dotted boxes.

Furthermore, the preprocessing device 27 is preferably designed for filtering the signals measured by the electrodes 15.

Preferably, but only optionally, the preprocessing device 27 has a common mode suppression device 28.

The common mode suppression device 28 is preferably designed to suppress or filter out a DC current component or DC voltage component of the signals measured by the various electrodes 15.

The examination apparatus 1 preferably has an A/D converter 29. The A/D converter 29 is preferably designed to convert an, in particular an analog, signal, preprocessed by the electrodes 15 and possibly by the preprocessing device 27, into a digital signal. The A/D converter 29 is preferably downstream of the preprocessing device 27.

The signal measured with the electrodes 15, in particular the cardiogram KG recorded with electrodes 15, is preferably further evaluated and/or processed, in particular after conversion into a digital signal. In particular, a usefulness check can be performed, e.g., by a check device 29A. During the usefulness check, it is preferably determined whether the cardiogram KG is useful, i.e. whether it can be meaningfully evaluated and/or contains useful information. This is shown schematically in FIG. 8 by the box in the lower right corner.

Preferably, the examination apparatus 1, as an alternative or in addition to the preprocessing device 27, has one or more further preprocessing devices 30. The preprocessing device 30 is preferably designed for the preprocessing of signals S measured by the sensor device 4 or detectors 6 and/or sensors 7.

The preprocessing device 30 preferably has an amplifier 31. The amplifier 31 is preferably designed to amplify a signal S measured by a detector 6 or sensor 7. In particular, the amplifier 31 is a transimpedance amplifier and/or converts a current into a voltage.

Preferably, the preprocessing device 30 has a filter device 32 for filtering the signal S, which is in particular amplified by the amplifier 31.

The filter device 32 preferably has several different electrical filters. In particular, the filter device 32 may have or form one or more passive filters and/or one or more active filters. The filter device 32 may, for example, comprise or form one or more bandpass filters, bandstop filters, high-pass filters and/or low-pass filters.

Preferably, each detector 6 or sensor 7 is assigned a preprocessing device 30 or each detector 6 or sensor 7 has a preprocessing device 30.

Preferably, an evaluation of the signals S measured by the sensor device 4 and preferably preprocessed by the preprocessing device 30, in particular the curves K, is performed together with the cardiogram KG and/or under consideration of the cardiogram KG.

The result of the evaluation can then, for example, be forwarded to an external device 23, as already described above and schematically indicated in FIG. 8.

The examination apparatus 1 is preferably designed to perform the method described below. Alternatively, or additionally, the examination apparatus 1 can be used to perform the method described below. This use can also be realized independently of further aspects of the present invention.

The following describes in particular a method according to the invention.

The method is preferably performed using the examination apparatus 1 described above. The above-described examination apparatus 1 is particularly advantageous for carrying out the method, in particular for selecting one or more sensors 7 and/or evaluating one or more curves K. However, the method can also be carried out independently of the described examination apparatus 1 and can preferably also be carried out with an examination apparatus 1 that is designed differently from the one described above.

The examination apparatus 1 is preferably designed to perform the method described below. Alternatively, or additionally, the examination apparatus 1 can be used to perform the method described below. This use can also be realized independently of further aspects of the present invention.

In particular, the examination apparatus 1 has means to perform the steps of the method. These means preferably comprise or are formed by a computer program.

The means and/or the computer program preferably comprise instructions which, when executed, cause the examination apparatus 1 to perform the described method.

According to another aspect, the computer program and/or the instructions are stored on computer-readable storage medium 26 or the computer-readable storage medium 26 comprises the computer program and/or instructions.

For medical examination, in particular blood pressure determination, by means of the examination apparatus 1, it is preferably intended that the animal T, in particular a domestic cat or a domestic dog, is placed on the examination apparatus 1. In particular, the animal T is placed completely on the examination apparatus 1, i.e. preferably in such a way that all limbs, in particular paws 2, are on the examination apparatus 1 and/or the entire weight of the animal T is carried by the examination apparatus 1.

Particularly preferably, the animal T is positioned on the examination apparatus 1 in such a way that a paw 2, in particular a forepaw, of the animal T rests on the sensor device 4 and/or is positioned directly above the sensor device 4 and/or a curve K comprising information about the arterial blood flow BF can be recorded on the paw 2.

Preferably, the animal T is positioned in such a way that each of the electrodes 15, 15A, 15B, 15C contacts a body part, in particular a paw 2, of the animal T, so that a cardiogram KG can be recorded by means of the electrodes 15. In particular, the animal T is positioned so that one of the forepaws contacts the first electrode 15A, the other forepaw contacts the second electrode 15B and, if the examination apparatus 1 has a third electrode 15C, one or both hindpaws contact the third electrode 15C.

After positioning the animal T, the medical examination and/or blood pressure determination is preferably started. Optionally it can be provided that after the positioning of the animal T first of all it is shortly awaited, so that the animal T can calm down and only after a waiting period the medical examination and/or blood pressure determination is begun. In particular, a curve K is recorded for the medical examination or blood pressure determination, which comprises information about an arterial blood flow BF of the animal T. This curve K is in particular a photoplethysmogram (PPG).

In the bottom of FIG. 9, a curve K is shown as an example.

Particularly preferably, a reflection measurement is performed for recording the curve K, or the examination apparatus 1 is designed for this purpose. This means in particular that the sensor device 4 is only located on one side of the paw 2 and/or has no components located on opposite sides of the paw 2.

Preferably, the examination or measurement is performed with radiation R in the infrared range.

It is particularly preferable that a cardiogram KG of animal T is recorded by means of the examination apparatus 1, in particular at the same time as the recording of the curve K comprising information about the arterial blood flow BF of the animal T.

In the top of FIG. 9, a cardiogram KG is shown as an example.

The examination apparatus 1 may have a processor P which receives and/or processes information and/or signals S and/or curves K from the examination apparatus 1, in particular the sensor device 4, the sensors 7, the detectors 6 and/or electrodes 15. Alternatively, or additionally, the processor P and/or the examination apparatus 1 has the storage medium 26, which has a computer program representing a proposed method, which can be executed with the processor P to carry out the method. In particular, the computer program is stored on the storage medium 26. Furthermore, results can be formed with the processor P. These results can be output, in particular via the display device 19, and/or transmitted, in particular to the external device 23.

The storage medium 26 can be integrated in the examination apparatus 1 or be separate from it, e.g., a storage means, such as a memory stick or an external database, a server or the like, that is connectable to the examination apparatus 1 via an interface. The computer program can also be supplied to the examination apparatus 1 from outside and stored in the examination apparatus 1. Here, however, other solutions are also possible.

The method, in particular the optical examination, is preferably performed with at least one sensor 7, preferably several sensors 7. Preferably, each sensor 7 corresponds to one measuring channel, each sensor 7 corresponds to one measuring channel and/or one measuring channel is assigned to each sensor 7.

A "measuring channel" in the sense of the present invention is preferably a transmission path for a signal S measured by a sensor 7, in particular a curve K measured by a sensor 7. Since in this sense the terms "measuring channel" and "sensor" are inseparably connected with each other, the following does not further differentiate between a sensor 7 and a measuring channel. Instead, the terms "measuring channel" and "sensor" will be used synonymously in the following, wherein the term "sensor" will be used primarily. In particular, the terms "measuring channel" and "sensor" are interchangeable.

Several curves K can be recorded simultaneously and/or one after the other via several sensors 7, preferably separately or independently of each other.

Preferably, each sensor 7 has at least one detector 6. Very particularly preferably, each sensor 7 has exactly one detector 6. Therefore, by selecting a sensor 7, a detector 6 is also selected and vice versa. In this respect, the terms "selection of a sensor" and "selection of a detector" are preferably synonymous and in particular interchangeable.

Furthermore, as already described above, each sensor 7 preferably has a sensor region 11. In other words, preferably each sensor 7 is assigned to a different measuring location or partial region of the sensing region 12 of the sensor device 4. In particular, each sensor 7 thus corresponds to a certain measurement location and/or sensor region 11 and/or partial region of the sensing region 12. A selection of a sensor 7 can therefore be understood as a selection of a measurement location and/or sensor region 11 and/or partial region of the sensing region 12. The terms "selection of a sensor", "selection of a measurement location", "selection of a sensor region" and "selection of a partial region of the sensing region" are therefore preferably synonymous with each other and in particular interchangeable.

Furthermore, one or more curves K is/are preferably recorded with each sensor 7. In other words, each curve K is assigned to a sensor 7. In particular, each curve K thus corresponds to a certain sensor 7. A selection of a curve K can therefore be understood as a selection of a sensor 7 and/or represents such. Indirectly, a selection of a curve K therefore also represents a selection of a measurement location and/or sensor region 11 and/or partial region of a sensing region 12. The terms "selection of a curve", "selection of a measurement location", "selection of a sensor region" and "selection of a partial region of the sensing region" are therefore preferably synonymous with each other and in particular interchangeable.

Further, in the examination apparatus 1 described above, the sensors 7 are preferably of the same kind or type, so that each sensor 7 performs the same measurement in principle and the measurements differ only in that they are measured at different locations, resulting in different (simultaneously) measured signals S or curves K.

Figure 10:
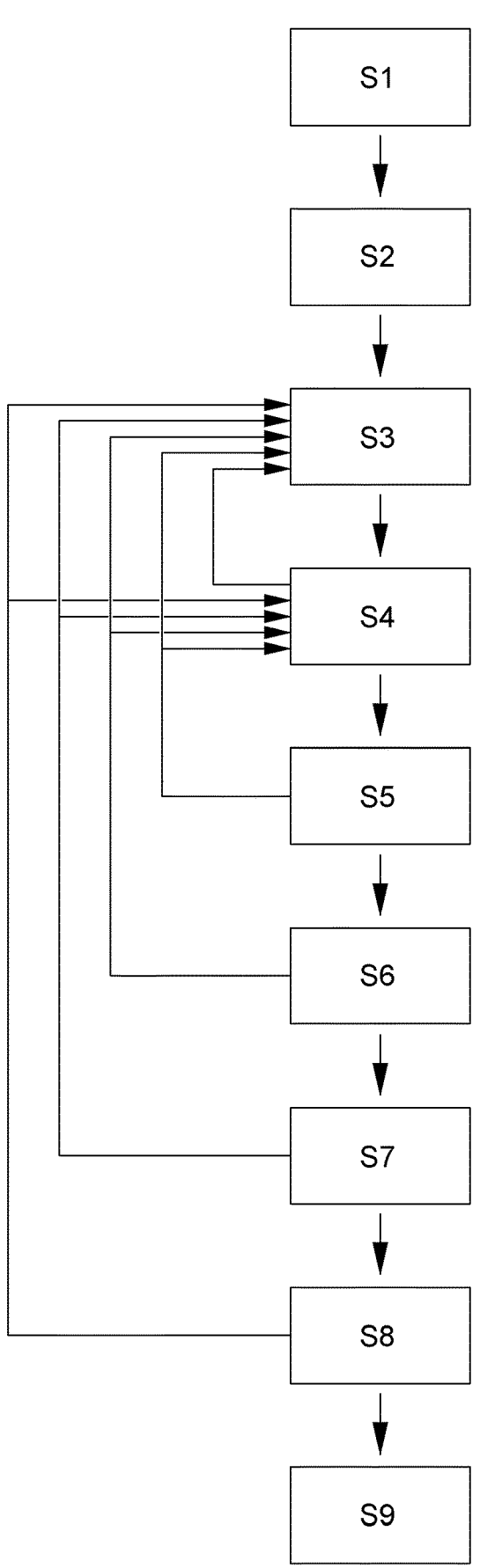
FIG. 10 is a schematic representation of a sequence of a
method according to the invention.

FIG. 10 shows a schematic overview of the general sequence of the method.

The method preferably has several steps S1 to S9, which are shown schematically in FIG. 10. In the following, at first a rough overview of the steps S1 to S9 is given. Subsequently, the steps S1 to S9 are described in more detail.

The method according to the invention does not necessarily include all steps S1 to S9. In particular, individual steps S1 to S9 or individual aspects of steps S1 to S9 can be realizable independently of each other or in different combinations.

In the method according to the invention, the animal T is medically examined Preferably, a pulse transit time PTT and/or blood pressure BP of the animal T is determined in the method according to the invention.

The animal T is preferably placed on the examination apparatus 1 for examination. Preferably, the animal T is not fixed on the examination apparatus 1, but can move freely, in particular relative to the sensor device 4 and/or the electrodes 15.

In step S1, it is preferably determined whether the animal T is located on the examination apparatus 1 and/or positioned on the examination apparatus 1 in such a way that the medical examination can be performed by means of the examination apparatus 1. However, step S1 is only optional and can be omitted.

In step S2 it is preferably determined whether a paw 2 is positioned on or above the sensor device 4 in such a way that the optical examination, in particular photoplethysmography, can be performed by means of the sensor device 4. Alternatively, or additionally, in step S2 it is determined over which of the sensors 7 the paw 2 is located or by means of which of the sensors 7 the examination can be performed. Preferably, only those sensors 7 are selected and/or used over which the paw 2 is located and/or by means of which the examination can be performed. Step S2 can also be performed simultaneously with step S1 or replace it. Step S2 is optional and can also be omitted.

Preferably, a selection of a sensor 7 or a subset of sensors 7 with which the examination is performed takes place in step S3. This is in particular advantageous if the sensor device 4 has a plurality or large number of sensors 7. In this way, the effort required for measurement and/or evaluation can be reduced considerably, in particular by excluding and/or not selecting sensors 7 and/or detectors 6, above which the paw 2 is not located, from a measurement or evaluation. Step S3 can also be performed simultaneously with step S1 and/or step S2. However, step S3 is in principle optional and can also be omitted.

On the other hand, the step S3 or a selection of a sensor 7 or a subset of the sensors 7 can be advantageous even without the subsequent steps and in particular can form an invention without the subsequent steps.

In step S4, a curve K comprising information about an arterial blood flow BF of the animal T, in particular a photoplethysmogram (PPG), is recorded. It is preferable to record a cardiogram KG, in particular at the same time as the curve K is recorded.

It is particularly preferred to record several curves K simultaneously, in particular at the same time as the cardiogram KG. Alternatively, or additionally, several curves K and/or cardiograms KG can be recorded one after the other, in particular with a temporal distance. In step S4, preferably the quality of the measurements and/or the usefulness of the recorded curve K and/or the cardiogram KG is also checked.

In step S5, the curve(s) K comprising information about an arterial blood flow BF is/are preferably cut or divided into curve sections KA. This is done in particular in such a way that the curve sections KA correspond to heartbeats, particularly preferably in such a way that each curve section KA corresponds to exactly one heartbeat. Preferably, the curve K is cut into curve sections KA using information from the cardiogram KG. However, other solutions are also possible here.

In step S6, preferably a selection of curve sections KA is made for further evaluation, in particular for the determination of a curve feature M and/or a blood pressure BP. For this purpose, some of the curve sections KA can be discarded in step S6. The selection of curve sections KA preferably constitutes a selection of one or more sensors 7, in particular if only curve sections KA are selected from a single sensor 7 or a subset of sensors 7. However, the step S6 is optional and can also be omitted.

In step S7, an averaging or average determination based on the curve sections KA is preferably performed. Preferably, one or more curve mean values KM are determined on the basis of the curve sections KA. A bootstrap method is preferably used or applied.

In step S8, a curve feature M is preferably determined. For this purpose, preferably several curve features M are determined first. In particular, a curve feature M is determined separately for each sensor 7, each curve section KA and/or each curve mean value KM. Particularly preferably, in addition to each curve feature M, an assigned measure of dispersion, is determined in each case. Particularly preferably, the curve feature M with the lowest measure of dispersion is selected as the final result of the curve feature M determined in step S8. This selected curve feature M then represents the curve feature M determined in step S8. The determined curve feature M can then be output and/or used as the basis for the determination of the blood pressure BP.

In step S9, preferably a blood pressure BP is determined, in particular from the curve feature M determined in step S8. This is done in particular by means of a preferably empirically determined correlation function F.

During one or more of the steps S5, S6, S7 and/or S8, a check can be made, in particular for the usefulness of a cardiogram KG and/or a curve K.

A check of a cardiogram KG for usefulness is preferably performed shortly after the start of the examination or recording of the cardiogram KG, in particular after a few seconds, preferably after at most about 5 seconds, particularly preferably after about 2 seconds.

A check of the curve K for usefulness is preferably performed after checking the cardiogram KG for usefulness. It is particularly preferred to check the usefulness of the curve K after at least about 5 s and/or at most about 45 s, particularly preferred after about 10 s and/or about 30 s. It is particularly preferred that a check of the curve K for usefulness is performed several times and/or after two different time periods, in particular a first check is performed after about 10 s and a second check after about 30 s.

The (first and/or second) check of the curve K for usefulness is preferably performed during the recording of the curve K or parallel thereto.

If it is determined that measurements are not useful and/or further measurements are required, after these steps S5, S6, S7 and/or S8 a return to step S4 can be made and/or a new and/or additional measurement can be made, as indicated by arrows in FIG. 10.

Alternatively, or additionally, it is also possible to return to step S3 after one of the steps S4, S5, S6, S7 and/or S8 and/or to make a new and/or different selection of sensors 7.

After a return to step S3 or to step S4, the following steps S4 to S9 or S5 to S9, respectively, are preferably run through again completely or partially.

Returning to a previous step and performing one or more steps more than once and/or again in particular has the consequence that the examination, in particular the determination of the blood pressure BP, of the animal T can be performed accurately and reliably even if the animal T moves during the examination or the paw 2 moves during the examination. In particular, the repetition of one or more steps allows cumulative measurements or recordings to be made until a sufficient number of data or curves K have been measured or are available. Hereby, measurement errors and/or movement artifacts can be compensated and a movement of the animal T or paw 2 during the examination is made possible. Since the animal T can preferably move freely during the examination, the examination is very pleasant for the animal T and therefore stress-free. This is conducive to an accurate and reliable examination, in particular blood pressure determination.

The steps S1 to S9 are described in more detail below.

Step S1

Preferably, in step S1 a presence of the animal T on the examination apparatus 1 is determined.

The examination apparatus 1 is preferably designed to identify a (potential) presence of an animal T, in particular a paw 2, on the examination apparatus 1 or at the examination apparatus 1, in particular on the rest surface 3, on at least one of the electrodes 15 and/or on the sensor device 4.

In principle, different methods can be used and/or different sensors can be provided for this purpose. For example, the examination apparatus 1 can have a presence sensor such as a light barrier, a motion detector or the like (not shown). However, the use of one or more components of the examination apparatus 1, in particular sensors including electrodes, which also serve another purpose, is particularly preferred.

Very particularly preferably, the sensor device 4 or one or more of the sensors 7 and/or detectors 6, the force sensor 18A and/or one or more electrodes 15 are used to detect the presence of the animal T or paw 2 on the examination apparatus 1 and/or the sensor device 4.

Particularly preferably, the examination apparatus 1 identifies the contact of the paw 2 with one or more of the electrodes 15, in particular by measuring an impedance or a resistance between electrodes 15. The resistance measured with the electrodes 15 changes in particular depending on whether or not the electrodes 15 are contacted by a paw 2 or the animal T. In this way, the presence of the animal T and/or a correct positioning of the paws 2 on the electrodes 15, in particular a positioning of the paws 2 in such a way that a cardiogram KG can be recorded by means of the electrodes 15, can be identified.

Alternatively, or additionally, the force sensor 18A and/or the scale 18 can be used to identify the presence of this animal T. In particular, a force or weight threshold value can be specified or specifiable for this purpose. In this case, the force or weight threshold value is preferably selected in such a way that it is exceeded when a domestic cat or a domestic dog or any other animal T to be examined is placed on the examination apparatus 1. Therefore, exceeding a weight threshold value is an indication of the presence of the animal T. Falling below the weight threshold value is an indication that no animal T is positioned on the examination apparatus 1 and/or that the animal T is only partially or not positioned on the examination apparatus 1 in the intended manner.

By means of an appropriate arrangement of the force sensor(s) 18A it is preferably also possible to determine by means of the force sensor(s) 18A whether and/or which of the electrodes 15 and/or sensor device(s) 4 are contacted by the animal T.

Alternatively, or additionally, the sensor device 4 or one or more of the sensors 7 and/or detectors 6 can be used to identify or determine the presence of the animal T. In particular, it can be determined by means of the sensor device 4 whether a paw 2 or any other part of the body of the animal T is located directly above the sensor device 4 and/or whether it is arranged in such a way that the paw 2 and/or the body part can be examined optically by means of the sensor device 4, in particular whether a photoplethysmography can be performed. This is preferably done by comparing the signals S measured by the sensors 7 of sensor device 4.

In this connection, on the one hand, it can be exploited that radiation R emitted by one or more of the emitters 5 reaches one of the detectors 6 at least essentially only in the presence of an object, i.e. preferably the animal T, in particular by reflection or scattering. On the other hand, it can be exploited that by a paw 2 positioned on the sensor device 4 the ambient light is at least partially shielded and/or only reaches some of the sensors 7. Therefore, an information about the presence of the animal T can be gathered from the signal S measured by the respective detector 6 or sensor 7, in particular without the need for a detailed evaluation of signals S. For example, it is sufficient to identify a certain signal level, e.g., by comparing a signal level with a threshold value or by comparing it with signals S measured by other sensors 7 or the like.

The presence detection or presence determination can be performed continuously, but for energy efficiency it is preferably performed intermittently.

The result of the presence detection or presence determination is preferably saved. The result is preferably a binary information, because it is either that the animal T is present or a presence could be determined (positive result) or that the animal T is not present or no presence could be determined (negative result). In particular, the result or the information is encoded in a signal of one or more of the sensors 7 and/or detectors 6 and/or the electrodes 15, in particular in a bit, most preferably the least significant bit. Such a method is also known as "lead-off detection".

Preferably, the presence detection or presence determination is repeated and/or (again) performed automatically, continuously and/or at regular intervals, for example at intervals of less than two seconds or less than one second, during performance of the examination and/or recording of the curve K and/or the cardiogram KG.

If a (potential) presence of an animal T or its paw 2 is determined on the examination apparatus 1, the examination apparatus 1 can be switched on (automatically), in particular it can switch from a power saving mode to an operating mode. The examination apparatus 1 can therefore support a power saving mode and be designed to leave this power saving mode as soon as the presence of the animal T or its paw 2 is detected.

The determination of the presence of the animal T or the paw 2 and in particular the control of the power supply of the examination apparatus 1 thereby is advantageous, but in principle, and in particular for further steps of the present invention, not mandatory, since—although less convenient—an activation of the examination apparatus 1 can be effected alternatively or additionally in particular by a switch or other operating device of the examination apparatus 1.

Step S2

Preferably, the examination apparatus 1 checks in step S2 whether and/or at which position a paw 2 is located on the sensor device 4 or the examination apparatus 1 is designed for this purpose, in particular by means of the sensor device 4.

To enable the proposed examination, the paw 2 of the animal T should rest on or against the sensor device 4 in such a way that the optical examination—as described above—can be performed. Particularly preferably, the paw 2 abuts directly on the sensor device 4 and in particular on the cover 14 for this purpose. In this case, a reliable optical examination can be performed. Alternatively, or additionally, the paw 2 of the animal T should have direct electrical or galvanic or, if applicable, capacitive contact with the electrode(s) 15, so that the recording of the cardiogram KG can be performed reliably.

In step S2, it is, preferably automatically, checked whether the paw 2 is resting on the sensor device 4 or is in contact with the sensor device 4 in an appropriate manner, so that the examination, in particular the optical examination and/or the recording of the cardiogram KG, is made possible.

On the one hand, it can be provided that signals S measured by the sensor(s) 7 are evaluated. This can consist of simply determining whether the signal S or the signals S correspond to a light incidence. In this way, a shadowing by the animal T or the paw 2 can be determined and thus a position of the paw 2 on the sensor device 4 can be detected.

Particularly advantageous is the measurement of electromagnetic radiation R emitted by the emitter(s) 5 by the detector(s) 6. When the emitter(s) 5 is (are) activated, it is also possible to determine, by evaluating one or more signals S from the detector(s) 6, whether an object and in particular the paw 2 of the animal T is arranged in such a way that radiation R emitted by the emitter(s) 5 reaches the detector(s) 6. In this case—or depending on the intensity—the presence of the paw 2 on the sensor device 4 can be deduced.

The determination of the presence and/or position of the paw 2 above the sensor device 4 is preferably done by comparing the signals S measured by the sensors 7 of the sensor device 4.

The comparison of signals S measured with the sensors 7 and/or detectors 6 is preferably done with activated or switched-on or emitting emitters 5, but can also be done with switched-off emitters 5.

By comparing the signals S from different sensors 7 and/or detectors 6 it can preferably be determined in which position, in particular relative to the sensor device 4 and/or the different sensors 7 and/or detectors 6, the paw 2 is located. In particular, it can be determined which of the sensors 7 and/or detectors 6 of the sensor device 4 the paw 2 is located over and thus by which sensors 7 and/or detectors 6 the examination, in particular the determination of the blood pressure BP, can be performed. In particular, the shape and/or positioning of the paw 2 can preferably be modelled.

If a paw 2 is located on the sensor device 4, preferably some areas of the sensor device 4 and/or some sensors 7 are covered by the paw 2 and other areas and/or sensors 7 are not covered by the paw 2. In particular, this leads to differences in the brightness and/or radiation R measured by the individual sensors 7. For the examination by means of the sensor device 4, it is preferably intended that a paw 2 is positioned over the sensor device 4 in such a way that the sensor 7 or at least one sensor 7 is completely covered by the paw 2. In this way, no ambient light can reach the sensor 7 or its detector 6, but only radiation R that was emitted by the emitter 5 or one of the emitters 5 of the sensor 7 and scattered in the paw 2 towards the detector 6.

The comparison of the different sensors 7 and/or the signals S measured with the sensors 7 is preferably done by forming differences between the signals S of different sensors 7.

Alternatively, or additionally, a position or presence determination by means of the sensor device 4 can be carried out by examining a signal S measured by means of the sensor device 4 to see whether it exceeds or falls below a threshold value, in particular an absolute signal strength.

Preferably, the threshold value represents an absolute brightness. In this way, it can in particular be determined whether a paw 2 and/or any other body part of the animal T is located above a sensor 7 of the sensor device 4 and/or above which sensors 7 of the sensor device 4 a paw 2 or any other body part is located.

In particular, exceeding the threshold value is an indication that no part of the body of the animal T is above the sensor device 4 or the sensor 7 and/or falling below the threshold value is an indication that the paw 2 or another part of the body of the animal T is located above the sensor device 4 and/or the sensor 7 in such a way that the curve K can be recorded.

Alternatively, or additionally, it can be provided that the wavelength of the radiation R measured by detector 6 or sensor 7 is analyzed. Preferably, the emitters 5 are designed to emit radiation R of a certain wavelength or in a narrow wavelength range. In other words, the emitters 5 preferably have a narrow spectrum. In contrast, ambient light, such as sunlight and/or artificially generated light for indoor lighting, usually has a wide spectrum, i.e. a plurality of different wavelengths, which are particularly outside the wavelength range emitted by the emitter 5. Therefore, by spectral analysis of the radiation R detected by the detector 6 or sensor 7, it can preferably be determined whether the sensor 7 is covered by a paw 2 or ambient light is measured.

If it is determined that the paw 2 is located only above some sensors 7 of the sensor device 4, in particular thus not over all sensors 7 of the sensor device 4, these sensors 7 can be selected for performing the examination and/or for recording a curve K comprising information about the arterial blood flow BF.

For presence and/or position determination by means of the sensor device 4, in particular a scan or search run can be performed by means of the sensors 7, in which different sensors 7 and/or emitters 5 are activated or switched on one after the other. In particular, the influence of ambient light can be determined hereby and/or by comparing a signal S measured with the emitter 5 switched on with a signal S measured with the emitter 5 switched off.

For the determination of the position of the paw 2 above and/or relative to the sensor device 4, in particular a center of mass or gravity of the signals S measured by the sensors 7 and/or detectors 6 is calculated or determined. The signals S are preferably proportional to the intensity of the radiation R measured by the respective sensor 7 and/or detector 6.

The determination of the center of mass or gravity of the measured signals S is done in particular as follows:

First, preferably each emitter 5, detector 6 and/or sensor 7 is assigned a position, preferably wherein the position is represented by two coordinates x, y. The position of each emitter 5, detector 6 and/or sensor 7 can thus be specified or defined by a pair of coordinates $(x_i, y_i)$, wherein the index i counts the emitters 5, detectors 6 and/or sensors 7. This is in particular shown in FIG. 4 as well.

The position of the paw 2 or the center of mass or gravity of the signals S is given by the coordinate pair $(x_c, y_c)$ with $$x_c = \frac{1}{S_{tot}} \Sigma_i S_i x_i$$

and $$y_c = \frac{1}{S_{tot}} \Sigma_i S_i y_i.$$

Here, $S_i$ is a value that corresponds to a signal strength $S_{orig,i}$ of signal S measured at the respective coordinate $x_i$ or $y_i$, respectively, or the sum of the signal strengths $S_{orig,i}$ measured at the respective coordinate $x_i$ or $y_i$, respectively. The factor $$\frac{1}{S_{tot}}$$

is a normalization factor and can be omitted if necessary. Preferably, $S_{tot} = \Sigma_i S_i$.

The signal strength $S_{orig}$ is preferably a value of the signal S measured by the sensor 7 and/or detector 6, for example a voltage, current or the like, in particular the DC value measured by the sensor 7 and/or detector 6.

A value $S_i$ corresponding to the signal strength $S_{orig,i}$ is preferably a value that is directly linked to the signal strength $S_{orig,i}$, for example the value of the signal strength $S_{orig,i}$ itself ($S_i = S_{orig,i}$). Particularly preferably, the value $S_i$ is the difference between the signal strength $S_{orig,i}$ and the mean value or median $S_m$ of the signal strengths $S_i$ ($S_i = S_{orig,i} - S_m$) or the absolute value thereof ($S_i = |S_{orig,i} - S_m|$).

After the determination of the position of the paw 2 or the center of mass or gravity ($x_c$, $y_c$), one or preferably several sensors 7, emitters 5 and/or detectors 6 are preferably selected or used for the medical examination, in particular photoplethysmography, on the basis of the determined position or the determined center of mass gravity. Preferably, sensors 7, emitters 5 and/or detectors 6 are selected or used which are closest to the determined position and/or are located in a certain area around the determined position. For example, sensors 7, emitters 5 and/or detectors 6 are selected which lie in a square, rectangle, (regular) hexagon, (regular) octagon or the like around the center of mass or gravity ($x_c$, $y_c$).

It is preferred that during the optical examination and/or during one or more of the subsequent steps, in particular during one of the steps S3 and/or S4, it is checked whether the position of the paw 2 has changed, in particular during a measurement and/or after the initial position determination, and/or the determination of the position of paw 2 is repeated. This position check is preferably done automatically, continuously and/or at regular intervals, preferably at intervals of less than two seconds or less than one second.

In order to check whether the position of paw 2 has changed after the initial position determination, the signals S measured by the sensors 7, emitters 5 and/or detectors 6, in particular those selected or used for the examination, or a control value $S_{new}$ determined from these signals S are compared with a reference value $S_{ref}$.

The reference value $S_{ref}$ is preferably a value that is measured and/or determined and during the initial determination of the position of the paw 2 preceding the check and is preferably stored.

The control value $S_{new}$ is preferably determined in the same way as the reference value $S_{ref}$ and/or on the basis of signals S that were measured with the same sensors 7, emitters 5 and/or detectors 6 as those signals S used to determine the reference value $S_{ref}$. In other words, the only difference between the control value $S_{new}$ and the reference value $S_{ref}$ is that they are recorded or determined at different times, namely the reference value $S_{ref}$ at the initial determination of the position of paw 2 or before the medical examination and the control value $S_{new}$ after the initial determination of the position of paw 2 or during the medical examination, in particular photoplethysmography.

Preferably, the reference value is $S_{ref}$ a value that is determined on the basis of signals S or signal strengths $S_{orig}$ measured by the selected sensors 7, emitters 5 and/or detectors 6. Particularly preferably, the reference value $S_{ref}$ is the sum of the values $S_i$ of the (selected) sensors 7, emitters 5 and/or detectors 6

$$\left(S_{ref} = \sum_{i=1}^{n} S_i\right)$$

or the average of the values $S_i$ of the (selected) sensors 7, emitters 5 and/or detectors 6

$$\left(S_{ref} = \frac{1}{n}\sum_{i=1}^{n} S_i\right),$$

wherein $S_i$ is the value explained above, the index i runs through the—preferably selected—sensors 7, emitters 5 and/or detectors 6 and n is the number of (selected) sensors 7, emitters 5 and/or detectors 6.

When comparing the control value $S_{new}$ with the reference value $S_{ref}$, preferably a deviation of the control value $S_{new}$ from the reference value $S_{ref}$, a ratio between the control value $S_{new}$ and the reference value $S_{ref}$, a difference between the control value $S_{new}$ and the reference value $S_{ref}$ or the like is determined or calculated.

Particularly preferably, the control value $S_{new}$ is compared with the reference value $S_{ref}$ by determining the quotient $S_{new}/S_{ref}$ between the control value $S_{new}$ and the reference value $S_{ref}$.

Further preferably, in order to obtain the result of the comparison, it is checked whether a value determined in the comparison, e.g., the difference between the control value $S_{new}$ and the reference value $S_{ref}$ and particularly preferably the quotient $S_{new}/S_{ref}$ is greater than or equal to a specified or specifiable threshold value.

The result of the comparison of the control value $S_{new}$ with the reference value $S_{ref}$ is preferably either that the position of the paw 2 has changed or that the position of the paw 2 has not changed.

If the value determined in the comparison, in particular the quotient $S_{new}/S_{ref}$, is greater than or equal to a specified threshold value, the result of the comparison is preferably that the position of the paw 2 has not changed. The threshold value can be 0.5, for example.

If the result of the comparison of the control value $S_{new}$ with the reference value $S_{ref}$ is that the position of the paw 2 has changed (from the position initially determined), the position of the paw 2 is preferably determined again, in particular by means of the method described above.

The comparison of the control value $S_{new}$ with the reference value $S_{ref}$ preferably takes place at regular (time) intervals, for example every second, every two seconds, every three seconds or the like.

If it is found that the position of paw 2 has been changed and/or the value determined in the comparison of reference value $S_{ref}$ with the control value $S_{new}$ is greater than or equal to the threshold value, the determination of the position of the paw 2, in particular the search run or scan, is preferably performed again, in particular automatically.

As an alternative or in addition to the presence and/or position determination by means of the sensor device 4, one or more of the electrodes 15 can be used to detect the presence of the paw 2 on the sensor device 4. In this case, a measurement is preferably performed to determine whether an electrically conductive, in particular a direct (galvanic) or capacitive electrical connection, exists between the paw 2 and an electrode 15 assigned to the sensor device 4 or arranged as part of or on the sensor device 4. If an electrical connection exists, this indicates the presence of the paw 2.

The measures can be combined in a particularly advantageous way. In particular, a sufficient presence of the paw 2 is automatically detected if both a contact with the electrode(s) 15 and either a shading of one or more detectors

6 or the identification of electromagnetic radiation coming from emitter(s) 5 with the detector(s) 6 is registered.

It is preferred that the presence detection takes place in an energy-saving manner. For example, the presence detection of the paw 2 on the sensor device 4 can be performed in several steps.

The measures can build on one another. For example, an—in particular intermittent and/or energy-saving—measure can be used first and if a (potential) presence of the animal T is detected, this can be verified with one or more of the other measures.

In a first step, the emitters 5 can be deactivated to save power. If then a shadowing is detected with a detector 6 and/or an electrical contact is detected with an electrode 15, it can be verified in a further step by another of the above-mentioned measures and/or by activating the emitter(s) 5 that the paw 2 also rests on or lies against the sensor device 4 in such a way that the examination can be performed.

In principle, it is therefore particularly preferable to use several of the devices provided by the examination apparatus 1 for performing the examination in addition for the determination of the presence of the paw 2 on the sensor device 4.

Preferably, the further steps of the method are only carried out if the presence of the paw 2 on or at sensor device 4 has been identified accordingly. Otherwise, it must be expected that energy and computing power will be expended without meaningful results being expected.

In principle, however, the proposed method can also do without step S2, in particular if in certain cases the additional effort of accepting an evaluation of possibly not correspondingly information-bearing signals is acceptable and/or if, on the basis of an evaluation at a later point in time of the proposed method, suitable signals S or parts thereof are selected and/or unsuitable ones are discarded.

In principle, step S1 can be supplemented or replaced by step S2. This is because the identification or detection of the presence of a paw 2 on the sensor device 4 is preferably accompanied by a detection of the animal T on the examination apparatus 1. This means that the evaluation of one or more signals S from one or more of the detector(s) 6 and/or the use of one or more electrodes 15 of the examination apparatus 1 for the determination of an electrical contact with a paw 2 can also be used to determine the presence of the animal T on the examination apparatus 1.

Step S2, in particular the determination of the position of the paw 2 above the sensor device 4 and/or the checking whether the position of the paw 2 has changed, can also be performed several times and/or simultaneously with a measurement or recording of a cardiogram KG and/or one or more curves K and/or simultaneously with an evaluation of the measurements or recordings. Particularly preferably, it is checked automatically, continuously or regularly and/or at short intervals, for example at intervals of less than two seconds or one second, whether the paw 2 has been moved. In particular, the step S2 can thus be performed simultaneously with one or more of the steps S4, S5, S6, S7, S8 and/or S9.

In particular, this allows the animal T to be examined to move during the examination and/or the paw 2 to be moved during the examination. Measurement errors and/or movement artifacts caused hereby can be compensated by the position determination, in particular in connection with a selection of sensors 7 and/or a discarding of unusable curves K or curve sections KA. In particular, it is possible that during and/or after a movement of the animal T or the paw

2, the examination is sustained or continued with one or more other sensors 7 or a different subset of sensors 7 than before the movement. The fact that the animal T can preferably move freely during the examination makes the examination very pleasant and stress-free for the animal T. This is conducive to an accurate and reliable examination, in particular blood pressure determination.

Step S3

Very particularly preferably, detectors 6 and/or sensors 7 are selected. In particular, a selection of detectors 6 or a selection of signals S measured with sensors 7 also represents or constitutes a selection of sensors 7 or vice versa. In particular, a pre-selection of sensors 7 is made, so that further steps and in particular an evaluation of the signals S measured by the sensors 7 is performed, if also information and/or an evaluability for the determination of a curve feature M and/or a blood pressure BP is/are to be expected.

A selection of a sensor 7 thus takes place in particular in that with this sensor 7 measurements are made, in particular signals S and/or curves K are recorded, and in particular are fed to a further evaluation. Alternatively, or additionally, a selection of a sensor 7 can also be made by operating and/or switching-on the emitter(s) 5 of the sensor 7 and/or by recording the measured signals S.

A non-selection of a sensor 7 takes place in particular in that no signals S are measured and/or no curves K are recorded with the sensor 7 and/or that signals S measured or curves K recorded with the sensor 7 are not considered in the further evaluation. In particular, signals S from unselected sensors 7 are thus rejected.

Figure 11:
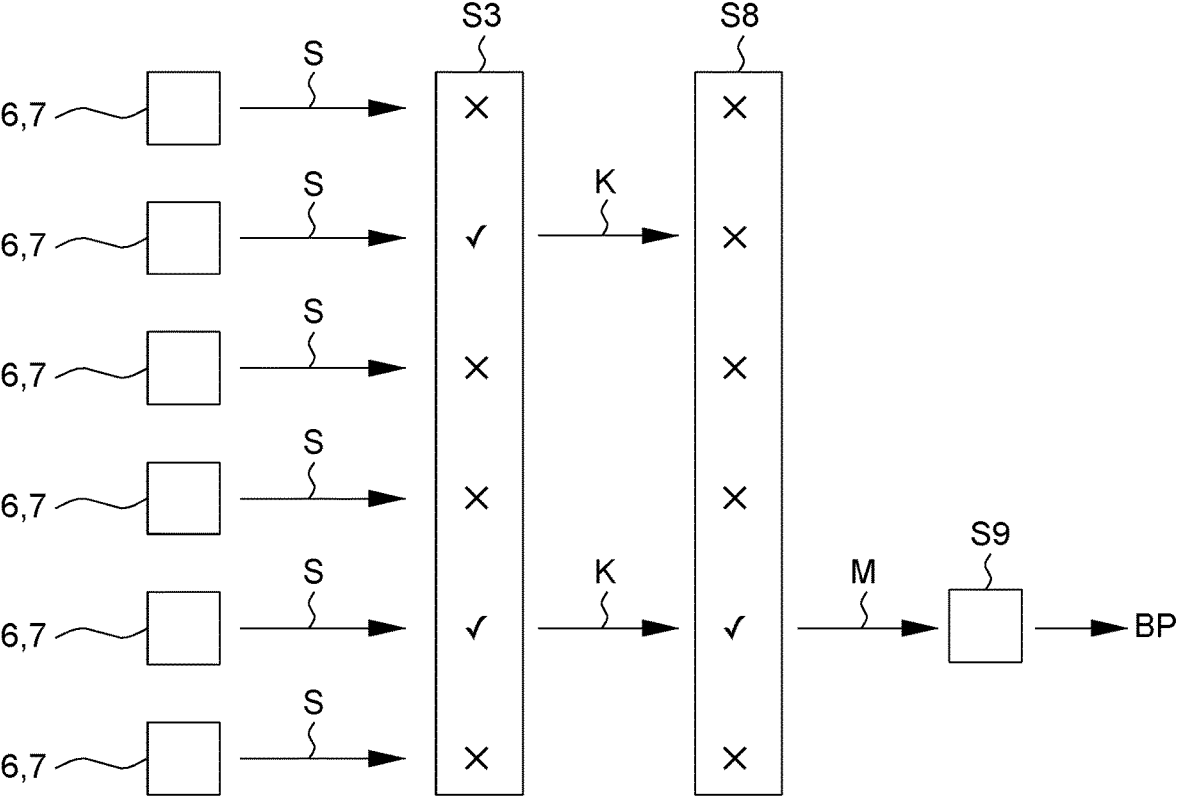
FIG. 11 is a schematic representation of a selection of
sensors and/or curves.

The selection of detectors 6 and/or sensors 7 is shown schematically in FIG. 11, wherein a cross symbolizes that the respective detector 6 or sensor 7 is not selected and the hook symbolizes that the respective detector 6 or sensor 7 is selected. In the example in step S3, two of the six shown detectors 6 and/or sensors 7 are selected and four detectors 6 and/or sensors 7 are not selected.

In this context, it should be taken into account that in order to perform the optical examination, in particular the photoplethysmography, a part of the paw 2 that has at least one artery A should be arranged in a sensor region 11 of a sensor 7, so that the optical examination and in particular the photoplethysmography can be performed. This is shown schematically in FIG. 7.

For the optical examination, in particular for performing a photoplethysmography, it is therefore preferred that a body part, in particular the paw 2, is placed on the sensor device 4 and/or the cover 14 in such a way or vice versa that an arterial blood flow BF is examined by means of the sensor device 4 and/or that the signals S comprise information about the arterial blood flow BF. In other words, the body part, in particular the paw 2, is in particular placed in such a way that the signals S comprise information about the arterial blood flow BF.

For the optical examination, in particular for performing a photoplethysmography, it is particularly preferred that a ball/pad of the paw 2 is put on/against the sensor device 4 and/or the cover 14. In particular, the hairless areas on the underside of the paw 2 are called pads. It has been shown that in the area of the pads the optical examination is particularly well feasible. It has also turned out that outside the pads the hairs located there make it difficult to perform the optical examination or photoplethysmography.

Accordingly, it is preferably detected or determined which of the sensors 7 and/or detectors 6 are located below the paw 2, in particular below a pad, and are therefore particularly suitable for carrying out the optical examination. These detectors 6 and/or sensors 7 or signals S measured with them are preferably selected. In this way, the further evaluation can be limited to signals S or sensors 7, respectively, which potentially lead to curves K that show useful or evaluable information about an arterial blood flow BF and/or on the basis of which a photoplethysmography can be performed and in particular a determination of a pulse transit time PTT and/or a blood pressure BP can be performed. This allows the examination to be performed in a particularly energy-saving manner.

By the selection of the signals S and/or sensors 7, preferably—at least indirectly—a selection of parts of the sensor device 4, of subsets of the sensors 7 and/or detectors 6 and/or of subsets of the sensing region 12 or of sensor regions 11 and/or detection regions 10 is performed, so that preferably only information or signals S or curves K originating from the selected parts or regions are recorded and/or evaluated and/or processed in the further course.

The selection and/or selective evaluation of information and/or signals S is particularly advantageous because both computing power and thus energy consumption can be saved and the computing power to be provided can be reduced, thus saving resources as a result.

The step S3 can be performed together or simultaneously with the step S2 and/or the step S1. In particular, measures based on each other can enable on the one hand the determination of the presence and/or positioning of the animal T on the examination apparatus 1 and the presence and/or position of the paw 2 on the sensor device 4 and on the other hand, preferably based on each other or simultaneously or based on the same signals S, the selection of detectors 6 and/or sensors 7. In principle, however, the further steps of the method can also be realized without such a selection and/or separately.

The selection of detectors 6 and/or sensors 7 in step S3 is performed in particular automatically and/or on the basis of the determination of the position of the paw 2 performed in step S2, in particular by means of the search run or scan. Thus, preferably those detectors 6 and/or sensors 7 are selected in step S3 for which it was determined in step S2 that the paw 2 is located above these detectors 6 and/or sensors 7 or that the paw 2 covers these detectors 6 and/or sensors 7.

The step S3 can also be performed repeatedly, in particular if in step S2 or through a new position determination it is found that the position of the paw 2 over the sensor device 4 has changed, for example through a movement of the paw 2 during the measurement and/or examination and/or recording of a curve K. In this case, preferably one or more other sensors 7 or a different subset of sensors 7 is selected than before. In particular, this allows the animal T to be examined to move during the examination or the paw 2 to be moved during the examination. Measurement errors and/or movement artifacts caused by this can be compensated for by selecting the sensor 7 again and/or by a different selection of sensors 7, in particular in connection with determining the position (again) and/or discarding of unusable curves K or curve sections KA. In particular, it is possible that during or after a movement of the animal T or the paw 2, the examination is sustained or continued with one or more other sensors 7 or a different subset of sensors 7 than before the movement. The fact that the animal T can preferably move freely during the examination makes the examination very pleasant and stress-free for the animal T. This is conducive to an accurate and reliable examination, in particular blood pressure determination.

Furthermore, the step S3 or the measures carried out in step S3 can also be realized and advantageous independently of the further steps S4 to S9.

Step S4

In the step S4, preferably one or more measurements are performed, in particular by means of the sensor device 4. In particular, one or more curves K containing information about an arterial blood flow BF, in particular photoplethysmograms (PPGs), are recorded.

This can be done with one or more detectors 6 and/or sensors 7. Accordingly, the curve(s) K preferably correspond(s) to the electromagnetic radiation R detected by the detector(s) 6, in particular an intensity of this radiation.

The electromagnetic radiation R preferably originates from the emitter(s) 5. In this context, the curve K shows preferably comprises the information about the arterial blood flow BF by the fact that the detected electromagnetic radiation R varies with the arterial blood flow BF, in particular in its intensity.

The radiation R emitted by the emitters 5 is scattered and/or reflected within the paw 2 during the examination of the paw 2 and can thus reach a detector 6. This is shown as an example in FIG. 7. The signal S measured by the detector 6 thus corresponds to the scattering, reflection and/or absorption of the radiation R emitted by the emitters 5 within the paw 2. Here, the scattering, reflection and/or absorption depends among other things on the volume of the blood in the blood vessels running in the paw 2 and/or on the oxygen saturation of the blood.

The scattering, reflection and/or absorption and thus the curve K measured by the detector 6 and/or sensor 7 are composed of a temporally at least approximately constant component and a temporally varying component.

The temporally constant the time course of the signal S recorded by a detector 6 or sensor 7 is caused in particular by the tissue surrounding the blood vessels, such as muscles, nerves, tendons, bones and/or skin, as the scattering and/or absorption by this tissue preferably does not change or only changes to a small extent. In particular, this temporally at least approximately constant component is not correlated with the heartbeat of animal T. The blood flowing through the veins can also contribute to this at least approximately constant component.

The temporally varying component is preferably caused, at least essentially, by the temporal change of the arterial blood flow BF, i.e. the blood flowing through arteries A. Arteries A are blood vessels through which the blood is carried away from the heart. The blood volume or volume flow through the arteries A and the oxygen saturation of the blood in arteries A change in a way correlated with the heartbeats. In particular, the absorption and/or scattering of blood in the arteries A does not only depend on the blood volume or blood flow in the arteries A, but also on the oxygen content or oxygen saturation of the blood in the arteries A.

In this context, the time course of a coherent and/or continuously recorded signal S is denoted as curve K. In a graphical representation of the signal S, as shown in FIG. 9, the curve K is the corresponding graph in the diagram.

However, the curve K can also be formed or represented by an equivalent of a graph or course of the signal S, in particular a data equivalent. Even if the curve K is preferably a continuous course, it can be represented or formed by single points or data points to be connected in thought, by vector trains or the like. The curve K can be or have a digitized analog signal S originating from the detector(s) 6 and/or sensor(s) 7.

Particularly preferably, the curve K is a digital signal S in the form of individual data points and/or the curve K is converted into individual data points for further evaluation after acquisition.

Preferably, a curve K starts with the beginning of the measurement of a signal S or the beginning of the recording of a signal S. Preferably, a curve K ends with the end or an interruption of the measurement or the recording of the signal S.

A "recording" of a signal S or a curve K is in particular a, preferably temporary, storage or intermediate storage of the signal S or the curve K. In particular, the term "recording" means the measurement and simultaneous storage or intermediate storage of a signal S or a curve K. The term "recording" therefore also includes a measurement, in particular a photoplethysmography.

Different curves K can be generated by carrying out different measurements, each of which is recorded, or by recording, storing and/or using (continuously) measured signals S only partially or section by section.

Preferably, several curves K are recorded simultaneously, in particular by means of different sensors 7 and/or detectors 6 of the sensor device 4. Alternatively, or additionally, several curves K can be recorded one after another with the same sensor 7 and/or detector 6 and/or several curves K can be recorded one after another with different sensors 7 and/or detectors 6.

According to a particularly preferred aspect, several curves K are thus recorded simultaneously, in particular with different sensors 7. Here, the different sensors 7, as explained above, preferably correspond to different areas of the sensor device 4 or the paw 2, so that as a result curves K from different areas of the sensor device 4 or the paw 2 are recorded. Preferably, curves K are only recorded with the detectors 6 and/or sensors 7 selected in step S3. However, this is not mandatory.

According to another aspect, several curves K are recorded one after the other with one detector 6 and/or sensor 7. However, simultaneously and/or with a time delay to the recording of the curve K with this sensor 7, further curves K can be recorded by other sensors 7.

In other words, the sensors 7 are—even if, as described above, some of the emitters 5 preferably form a part of several sensors 7—preferably separate from each other, so that with each sensor 7 several curves K can be recorded or are recorded one after the other and independently of this, one or more curves K can be recorded or are recorded simultaneously with the other sensors 7.

However, the sensors 7 are particularly preferably synchronized, so that the curves K are recorded simultaneously with the sensors 7.

It is particularly preferred, although not mandatory, that a cardiogram KG, in particular an electrocardiogram and/or impedance cardiogram, is recorded simultaneously with the curve K or curves K. The cardiogram KG is in particular recorded by means of the electrodes 15. In principle, however, the cardiogram KG can also be recorded with another detection element, for example a microphone or the like, or be a phonocardiogram.

For recording the cardiogram KG, particularly preferably an electrode 15 is used, which contacts the paw 2 at which the optical examination by means of the sensor device 4 is performed as well. Preferably, an or the (first) electrode 15A, which is assigned to the sensor device 4, is used for this purpose, wherein the (first) electrode 15A is preferably designed and arranged in such a way that when the paw 2 is placed on the sensor device 4, a photoplethysmography is made possible and at the same time an electrical coupling of the paw 2 with the electrode 15A takes place. In the illustration example, the first electrode 15A is arranged or formed on or in the immediate vicinity of the sensor device 4.

Preferably, the cardiogram KG is checked for usefulness, in particular automatically or in an automated manner. The check for usefulness can be performed during or after the recording of the cardiogram KG.

For the recording of the cardiogram KG, preferably several electrodes 15 are used, of which one electrode 15A can be, but need not be, the electrode 15A assigned to the sensor device 4. Furthermore, the examination apparatus 1 has one or more electrodes 15, so that the animal T or its different paws 2 or other body parts are preferably electrically coupled or contacted by different electrodes 15.

Here, one of the electrodes 15, in particular the third electrode 15C, can function as a collecting electrode or reference electrode for one or more other electrodes 15. Preferably, a unipolar and/or bipolar lead is used, in particular following the lead system according to Frank Norman Wilson of 1934, the lead system according to Emanuel Goldberger of 1942 and/or the lead system according to Willem Einthoven of 1913. However, other approaches are also possible here.

The collection electrode or reference electrode 15C can be used, in order to compensate for a DC voltage or to set an electric potential, to introduce a current into the animal T or to set an electrical voltage. The collecting electrode or reference electrode 15C is preferably serves for the measurement of an averaged potential or reference potential which forms a reference point for the potentials measured with the other electrodes 15.

In principle, a single-channel cardiogram KG and/or two electrodes 15 are sufficient. The use of at least a third electrode 15 is particularly preferred, allowing several cardiograms KG, in particular ECG channels, to be recorded. Furthermore, these can be used as alternatives to each other or in combination.

Preferably, the cardiogram KG is preprocessed, in particular with the preprocessing device 27. In particular, the cardiogram KG can be filtered, particularly preferably bandpass filtered. Here, a frequency range of lower frequencies and a frequency range of higher frequencies adjacent to a middle frequency range is attenuated. Alternatively, or additionally, a notch filter and/or bandstop filter can be used to filter the cardiogram KG. Here, certain frequencies or frequency bands are attenuated or suppressed. Especially disturbances from the power grid can be suppressed, for example disturbances with a frequency of 50 Hz.

If the cardiogram KG is not useful, i.e. does not meet the check criteria for usefulness, the cardiogram KG is preferably discarded. In particular, if the cardiogram KG is not useful, any K curve(s) recorded at the same time as the cardiogram KG will also be discarded. Preferably, a further evaluation is performed exclusively on curves K and/or cardiograms KG which have not been discarded.

Particularly preferably, if the cardiogram KG is not useful, a new cardiogram KG and, preferably, one or more new curves K corresponding to the new cardiogram KG are recorded, preferably at the same time as the new cardiogram KG is recorded.

The check for usefulness is preferably performed on a cardiogram KG or a section of a cardiogram KG that has or corresponds to more than 2, preferably more than 4, and/or less than 20, preferably less than 15, in particular less than 10, most preferably about 6 to 8, heartbeats and/or QRS complexes.

The check for usefulness is hereby or alternatively or additionally preferably performed on a cardiogram KG or a section of a cardiogram KG whose length is or corresponds to more than 0.5 s, preferably more than 1 s, and/or less than 10 s, in particular less than 5 s, particularly preferably less than 3 s. Most preferably, the length of the cardiogram KG or the section, respectively, is about 2 s. The length of the cardiogram KG or section is in particular the duration of the measurement of the cardiogram KG or section.

Preferably, one or more criteria are checked when checking the usefulness of the cardiogram KG. The cardiogram KG is preferably useful if all of the criteria explained below are met. In principle, however, other methods are also possible in which only some of the criteria explained below are checked and/or a cardiogram KG is also considered useful if only one or a subset of the criteria are met. Alternatively, or in addition, other criteria than those described below may also be provided for.

According to a first criterion, preferably a peak-to-peak amplitude of the cardiogram KG is determined. A filtered and/or preprocessed cardiogram KG is preferably used for this purpose. The peak-to-peak amplitude is the difference between the value of an absolute maximum and the value of an absolute minimum of the cardiogram KG. If the peak-to-peak amplitude is greater than or equal to a specified or specifiable threshold value, the criterion is considered fulfilled. Otherwise, the criterion is considered not fulfilled.

According to a second criterion, preferably a power spectral density or power distribution of the cardiogram KG is determined. In particular, it is checked whether the quotient of an integral over the power density spectrum in a first interval and an integral over the power density spectrum in a second interval is greater than or equal to a lower threshold value and/or less than or equal to an upper threshold value. The criterion is considered fulfilled if the quotient is greater than or equal to the lower threshold value and/or less than or equal to the upper threshold value. Otherwise, the criterion is considered not fulfilled.

According to a third criterion, preferably a skewness and/or kurtosis of an amplitude distribution function of the cardiogram KG is examined. The criterion is considered fulfilled if the kurtosis and/or skewness is greater than or equal to a specified or specifiable threshold value. Otherwise, the criterion is considered not fulfilled.

According to a fourth and fifth criterion, preferably a Pan-Tompkins plot of the cardiogram KG is examined.

The Pan-Tompkins algorithm is an algorithm for the detection of QRS complexes in a cardiogram KG, in particular an electrocardiogram. According to the Pan-Tompkins algorithm, the cardiogram KG is filtered, derived, squared and then convoluted and/or integrated. The curve resulting from these steps or the application of the Pan-Tompkins algorithm to the cardiogram KG is called Pan-Tompkins plot. The QRS complexes and/or R peaks of the cardiogram KG can be reliably determined from the Pan-Tompkins plot.

In the context of the present invention, it has turned out that also the usefulness of the cardiogram KG can be checked by means of the Pan-Tompkins plot.

According to the fourth criterion, a minimum and/or mean amplitude of the peaks of the Pan-Tompkins plot is examined. The criterion is considered fulfilled if the minimum and/or mean amplitude of the Pan-Tompkins plot is/are greater than or equal to a specified or specifiable threshold value. Otherwise, the criterion is considered not fulfilled. Different threshold values may be provided for the minimum amplitude and the mean amplitude.

According to the fifth criterion, a minimum, maximum and/or mean distance of the peaks of the Pan-Tompkins plot is examined. The criterion is considered fulfilled if the minimum, maximum, and/or mean distance of the peaks of the Pan-Tompkins plot is greater than or equal to a lower threshold value and/or less than or equal to an upper threshold value. Otherwise, the criterion is considered not fulfilled. Different thresholds may be provided for the minimum distance, the maximum distance, and the average distance.

According to a sixth criterion, a saturation of the cardiogram KG or the signals measured by the electrodes 15 is examined A saturation of the signal or cardiogram KG is present when the signal takes the maximum or minimum value possible when the signal is measured with the electrode 15. Preferably, the sixth criterion is used to determine the proportion, in particular the time proportion, of the signal or cardiogram KG measured with the electrode 15 that is saturated. The criterion is considered fulfilled if the proportion is less than or equal to a specified or specifiable threshold value. Otherwise the criterion is considered not fulfilled. For example, the threshold value can be 0.15 or 15%, so that the criterion is not fulfilled if more than 15% of the cardiogram KG is saturated.

As an alternative or in addition to checking the cardiogram KG for usefulness, the curve K can be checked for usefulness. This check for the usefulness of the K curve is preferably performed after the measurement or recording of the curve K, in particular on the basis of individual curve sections KA, and preferably if the cardiogram KG fulfills the criteria for its usefulness.

The check for the usefulness of curve K is preferably performed in step S6 and is therefore described in more detail below in connection with step S6. In principle, however, it is also possible that a (basic) usefulness check of the curve K also or additionally forms a part of the step S4 and/or that the usefulness check is performed during recording of the curve K. In order to check the usefulness of the curve K, it is preferable to assess it with respect to a criterion, for example an expected basic shape, an expected spectrum, an expected amplitude or the like.

The check for the usefulness of the curve K is preferably performed after the measurement or recording of the curve K, in particular on the basis of individual curve sections KA, and preferably if the cardiogram KG meets the criteria for its usefulness.

In principle, it is not mandatory to check the usefulness of the cardiogram KG and/or the curve K. However, it has proven to be particularly advantageous for the examination of animals T, in particular domestic dogs or domestic cats, because by this in a simple and/or fast way useless measurements, i.e. measurements which do not contain any useful information and/or do not contribute to a reliable result of an evaluation, can be sorted out and/or ignored or remain unconsidered for further evaluation. In particular, the usefulness check preferably contributes to the fact that a medical examination, in particular blood pressure determination, of the animal T can be performed even if the animal T is not fixed relative to the examination apparatus 1, in particular relative to the sensor device 4 and/or the electrodes 15, or moves or can move relative to the examination apparatus 1, in particular relative to the sensor device 4 and/or the electrodes 15, during the examination. In particular, by the usefulness check, measurements during which the animal T has moved can be detect and preferably sorted out or not be taken into account in the further evaluation. In this way, the examination can be made particularly pleasant and stress-free for the animal T. This is conducive to a reliable and accurate examination, in particular the determination of blood pressure BP.

Preferably, the duration of a measurement or recording of a curve K is more than 30 seconds and/or less than 60 seconds, in particular about 45 seconds. Here, several curves K and/or a cardiogram KG are preferably recorded simultaneously.

Particularly preferably, it is determined whether and/or when the animal T, in particular the paw 2, is moved during the recording of a curve K and/or cardiogram KG, preferably this taking place by means of the checking of the position of the paw 2 already explained in step S2. Segments of curve(s) K and/or cardiogram KG in which the animal T and/or paw 2 was moved are preferably removed or cut out from curve(s) K and/or cardiogram KG. Segments in which no movement of the animal T or paw 2 has occurred or been detected and which have a length of less than or at most 5 seconds are preferably also cut out of the curve K and/or cardiogram KG.

The remaining segments of the curves K and/or the cardiogram KG, i.e. the segments in which no movement of the animal T or paw 2 was detected and/or which were not removed, are preferably joined together, in particular to form a new curve K.

Preferably, the curve K or the curves K KG combined in this way and/or the cardiogram KG combined in this way forms/form the basis for the further evaluation or medical examination, in particular determination of the blood pressure. In other words, the further steps S5 to S9 are preferably performed with the curve(s) K and/or cardiogram KG from which segments have been removed in which the animal T and/or the paw 2 has been moved.

The removal of segments in which the animal T and/or the paw 2 has been moved is preferably performed in addition to and/or after the (previously explained) usefulness check of the cardiogram KG.

It is preferable that the curve K and/or the cardiogram KG combined in this way have a length of at least 20 seconds, particularly preferably at least 30 seconds, and/or consist exclusively of segments which have a length of more than 3 seconds, preferably more than 5 seconds. If these requirements are not met after cutting out the segments in which movement has occurred, the recording of the curve(s) K and/or the cardiogram KG is preferably restarted or repeated.

Furthermore, it is possible that a curve K is composed of segments of several curves K which were measured or recorded with different detectors 6 and/or sensors 7, in particular if during a recording of several curves K the position of the paw 2 was changed and/or due to such a change of a position of the paw 2 curves K were recorded with different detectors 6 and/or sensors 7.

It is particularly preferred that during the step S4 or during the recording of the curve(s) K and/or the cardiogram KG, the presence determination performed or described in particular in step S1, the position determination described in particular in step S2 and/or the position check described in particular in step S2 are performed. This is performed in particular automatically, continuously and/or at regular intervals, preferably with intervals of less than 2 seconds or less than 1 second. In particular, it is possible to determine in this way if the animal T is moved or moves and/or the position of one or more paws 2 changes. When the animal T or its paw(s) 2 has been found to move, the presence and/or position determination shall preferably be repeated, in particular automatically, and preferably new sensors 7 and/or detectors 6 shall be selected and with these newly selected sensors 7 and/or detectors 6 the measurement or recording of the curve(s) K shall be continued or further or new curve(s) K shall be recorded, in particular automatically. This is explained below for different situations or phases P1 to P7 which may occur during an examination of the animal T.

Figure 14:
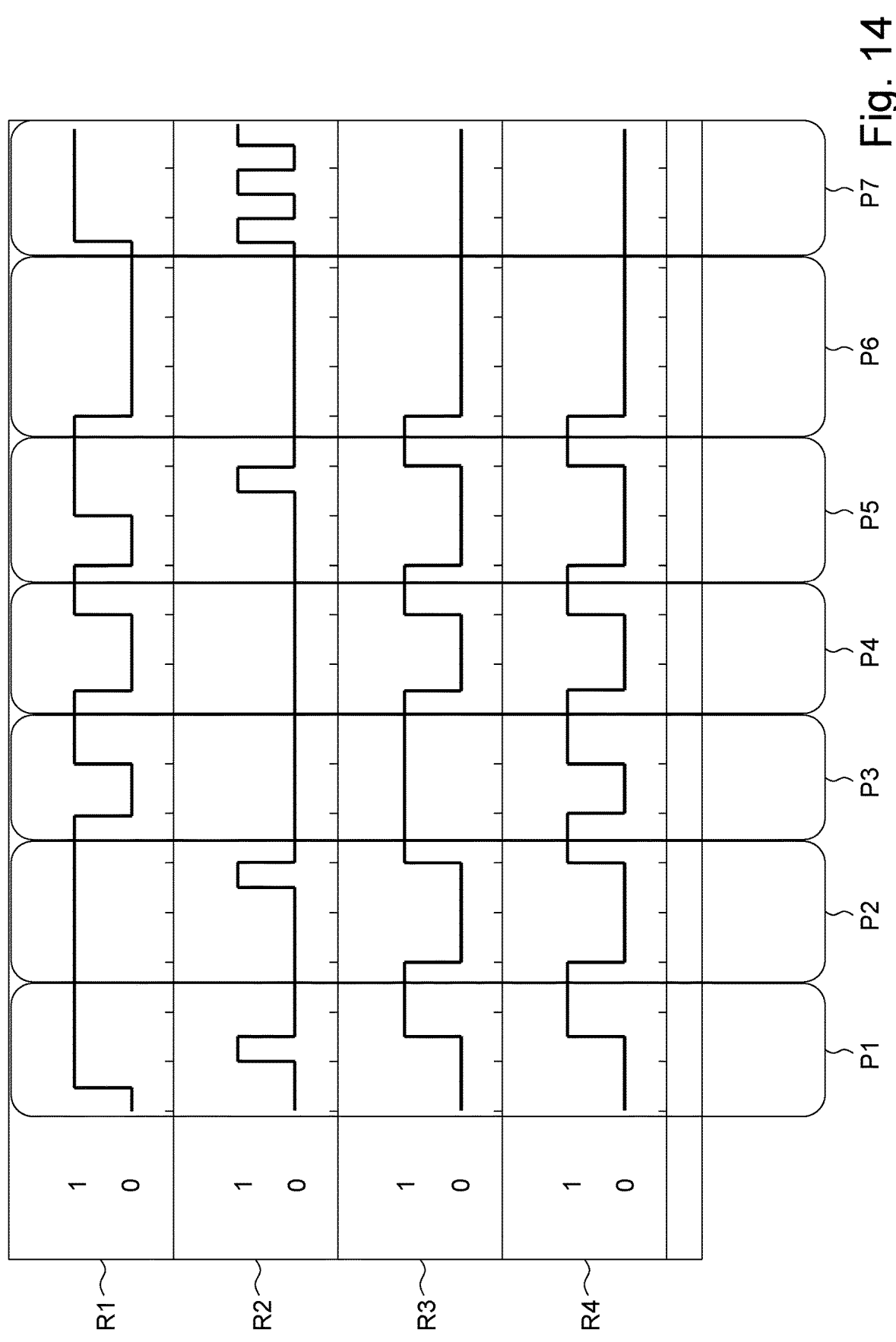
FIG. 14 is a schematic representation of different phases
of a medical examination of an animal.

In FIG. 14, various possible phases P1 to P7 during a measurement or recording of a cardiogram KG and/or a curve K are shown schematically and by way of example. The sequence of the phases P1 to P7 is therefore purely exemplary for illustration purposes and does not represent a mandatory sequence of the phases P1 to P7. Rather, the phases P1 to P7 can occur in any order and the phases P1 to P7 can occur several times and/or not at all during an examination or recording of the curve(s) K and/or the cardiogram KG.

In the following explanation of the phases P1 to P7 it is assumed that the examination apparatus) has (at least) two electrodes 15, in particular an electrode 15A for the left (fore-)paw and an electrode 15B for the right (fore-)paw of the animal T. It is further assumed that the examination apparatus 1 has only or exactly one sensor device 4, wherein the sensor device 4 is assigned to the left (fore-)paw or is positioned under the left (fore-)paw of the animal T during the examination. Preferably, the presence of the animal T is determined by means of the electrodes 15A, 15B and the position of the paw 2, in particular the left forepaw, is determined and checked with the sensor device 4 and the curve K is recorded. Of course, other versions of the examination apparatus 1 are also possible, in which case the following explanations apply accordingly.

FIG. 14 shows in four rows R1 to R4 different actions or results of actions which are performed during phases the P1 to P7. The abscissa or X-axis of the diagram in FIG. 14 represents in particular a time axis.

In the row R1, in particular the result of the presence determination, which is performed in particular in step S1, is shown. During the presence determination, it is preferably determined, as described, whether a paw 2 of the animal T, in particular the right forepaw, is placed on the assigned electrode 15A, 15B in such a way that a cardiogram KG can be recorded. Here, the value "1" means that the presence determination was or is successful or that the right forepaw is placed correctly (positive result). The value "0" means that the presence could not be determined or that the right forepaw is not correctly placed (negative result).

In the row R2, carrying out of a determination of the position of the paw 2, in particular the left forepaw, is shown. The position determination is carried out in particular as described above in step S2, preferably by carrying out a search run or scan with the sensors 7 and/or by determining the center of mass or gravity of the measured signals S. Here, the value "1" means that the position determination and/or the search run or scan is carried out. The value "0" means that no position determination or search run or scan is carried out.

In the row R3, the result of a check of the position of the paw 2, in particular the left forepaw, which is preferably performed as explained above in step S2, is shown. In particular, as described, it is checked continuously and/or regularly whether the position of the left forepaw has changed compared to the position initially or previously determined. The value "1" means that the position has been successfully detected or has not changed from the position determined initially or previously (positive result). The value "0" means that no position has been detected or the position has changed compared to the initially previously detected position (negative result).

In the row R4, the performance of a measurement or examination, in particular the recording of a curve K and a cardiogram KG, is shown. The recording of the curve K is performed in particular by means of the sensor device 4 on the left forepaw of the animal T. The recording of the cardiogram KG is performed by means of the electrodes 15A, 15B, wherein one electrode 15A contacts the left forepaw and one electrode 15B contacts the right forepaw of the animal T. The value "1" means that a curve K and a cardiogram KG are being recorded. The value "0" means that no curve K and/or no cardiogram KG is being recorded.

The phase P1 is in particular a starting phase. In the phase P1, the animal T is placed on the examination apparatus 1 for examination. In the phase P1, a presence determination of the animal T or paw 2 is preferably performed first. When the presence of the animal T has been successfully determined or detected (value in R1 jumps from 0 to 1), a search run and/or position determination is preferably performed with the sensors 7 to determine the position of the left forepaw (value in R2 jumps from 0 to 1). When the position of the left forepaw has been determined successfully and thus the search run and/or position determination is finished (value in R2 jumps from 1 to 0 and value in R3 jumps from 0 to 1), the measurement begins and/or at least one curve K and a cardiogram KG are recorded (value in R4 jumps from 0 to 1).

In phase P2, the position of the left forepaw is changed without removing or lifting the left forepaw from the sensor device 4. During this, the right forepaw remains in contact with the assigned electrode 15B. The result of the presence detection during the entire phase P2 is that the animal's paw 2 is present (value in R1 is 1). During the position check, it is determined that the position of the left forepaw has changed compared to the originally determined position (value in R3 jumps from 1 to 0). Accordingly, the recording of the curve K and cardiogram KG is interrupted or terminated (value in R4 jumps from 1 to 0) and a new position determination is performed (value in R2 jumps from 0 to 1). When the (new) position of the left forepaw has been determined successfully (value in R2 jumps from 1 to 0 and value in R3 jumps from 0 to 1), a new recording of the curve K and the cardiogram KG starts or the recording of the curve K and the cardiogram KG is continued (value in R4 jumps from 0 to 1).

In phase P3, the right forepaw is first lifted off the assigned electrode 15B and then placed back on the electrode 15B. During this, the position of the left forepaw is not changed. Accordingly, the result of the presence detection is negative when or after lifting the right forepaw (value in R1 jumps from 1 to 0). Since the position of the left forepaw does not change, the result of the position check is positive and no new position determination is performed (value in R3 is constant 1 and value R2 is constant 0). Since the right forepaw was lifted off the electrode 15B, no cardiogram KG can be recorded, so that recording of the curve K and the cardiogram KG is interrupted or terminated (value in R4 jumps from 1 to 0). After the right forepaw has been placed back on the electrode 15B, the result of the presence detection is positive again (value in R1 jumps from 0 to 1). Accordingly, the recording of the curve K and the cardiogram KG is continued (value in R4 jumps from 0 to 1).

In phase P4, the left forepaw is lifted off the sensor device 4 and the assigned electrode 15A and then placed in the same position on the sensor device 4 and the assigned electrode 15A again. When or after lifting the left forepaw, the result of the presence detection is negative (value in R1 jumps from 1 to 0). In addition, the result of the position check is negative (value in R3 jumps from 1 to 0). Accordingly, the recording of the curve K and the cardiogram KG is interrupted or stopped (value in R4 jumps from 1 to 0). When the left forepaw is placed on the assigned electrode 15A and the sensor device 4 again (in the same position as before), the result of the presence detection is positive again (value in R1 jumps from 0 to 1) and the result of the position check is also positive (value in R3 jumps from 0 to 3). Since there have been no changes compared to the previously determined or last saved position of the left forepaw, no new position determination is performed (value in R2 is constant 0). After the left forepaw 2 has been put on again, a new recording of the curve K and the cardiogram KG begins or the recording of the curve K and the cardiogram KG is continued (value in R4 jumps from 0 to 1).

In phase P5, the left forepaw is lifted off the electrode 15A and/or the sensor device 4 and then placed again in a changed position on the sensor device 4 and the assigned electrode 15A. After lifting the left forepaw, the result of the presence detection and the position check is negative (value in R1 and R3 jumps from 1 to 0), so that the recording of the curve K and the cardiogram KG is interrupted or terminated (value in R4 jumps from 1 to 0). As soon as the paw is put back on, the result of the presence detection is positive (value in R1 jumps from 0 to 1). Since the position has been changed, the result of the position check remains negative at first (value in R3 is still 0), so the position of the left forepaw is determined again (value in R2 jumps from 0 to 1). When the new position of the left forepaw has been successfully determined and the position determination has been completed (value in R2 jumps from 1 to 0 and value in R3 jumps from 0 to 1), a new recording of curve K and cardiogram KG begins or recording of curve K and cardiogram KG is continued (value in R4 jumps from 0 to 1).

In phase P6, the animal T or both forepaws are removed from the assigned electrodes 15A, 15B. Accordingly, the result of the presence detection and the position check is negative (value in R1 and R3 jumps from 1 to 0) and the recording of the curve K and the cardiogram KG is interrupted or terminated (value in R4 jumps from 1 to 0). The value in R2 is constantly 0, since no renewed presence of the animal T is detected.

In phase P7, the forepaws are brought into contact with the assigned electrodes 15A, 15B, but the left forepaw is placed in such a way that the position cannot be determined and/or no meaningful measurement can be made. Accordingly, the result of the presence detection is positive (value in R1 jumps from 0 to 1). A position determination is repeatedly performed, but this does not lead to a successful result (value in R2 alternates between 0 and 1, value in R3 is 0). Accordingly, no curve K and no cardiogram KG is recorded (value in R4 is 0).

The step S4 or the recording of one or more cardiograms KG and/or curves K and/or checking for usefulness can also be carried out several times or several times in succession, in particular even after an evaluation or partial evaluation of curves K has already been carried out, in particular according to one of the steps S5, S6, S7, S8 and/or S9. For example, the evaluation may reveal that there are not enough useful curve sections KA, so that further curves K must be included. This can be caused by a movement of the animal T or the paw 2, for example.

In particular, multiple recording of cardiograms KG and/or curves K or a repetition of the step S4 allows the animal T to be moved during the examination and/or the paw 2 to be moved during the examination. Measurement errors and/or movement artifacts caused by this can be compensated by the multiple recording of cardiograms KG and/or curves K, in particular in connection with the multiple presence detection and/or selection of sensors 7 and/or discarding of unusable curves K or curve sections KA. In particular, it is possible that during or after a movement of the animal T or the paw 2, the examination is sustained or continued with one or more other sensors 7 or a different subset of sensors 7 than before the movement. The fact that the animal T can preferably move freely during the examination makes the examination very pleasant and stress-free for the animal T. This is conducive to an accurate and reliable examination, in particular blood pressure determination.

Step S5

In step S5, the curve(s) K is/are preferably cut into curve sections KA, in particular in such a way that the curve sections KA correspond to one heartbeat each. Particularly preferably, each curve section KA corresponds to exactly one heartbeat.

A cutting or slicing of the curve K in the sense of the present invention is preferably to be understood as a division or partitioning of the curve K along the time axis. The curve K is thus divided into temporal sections. This can be realized by data processing in such a way that the beginnings and/or ends of curve sections KA are identified and/or marked. In principle, it is possible to separate the curve sections KA from each other. In the further processing, the curve sections KA are also preferably treated separately. Against this background, however, the "slicing" or "cutting" does not necessarily imply a physical separation of the resulting curve sections KA from each other.

As can be seen from the curve K shown in FIG. 9 as an example, which corresponds to a photoplethysmogram actually measured on a cat, usually and in particular in contrast to a cardiogram KG, a regularity or periodicity, in particular correlation with heartbeats, of the curve K cannot be directly seen. Therefore, it is advantageous to cut the curve K by means of information from a cardiogram KG and then to perform a further evaluation based on individual curve sections KA.

In the following, the cutting or slicing of curves K is explained using the example of a single curve K. Preferably, all recorded curves K are cut into curve sections KA in the same way.

The cutting of the curve K into curve sections KA is preferably automated or takes place in an automated manner.

Particularly preferably, the curve K is cut into the curve sections KA using information from the cardiogram KG recorded at the same time as the curve K. In principle, however, other methods are also conceivable here.

The use of the cardiogram KG to slice/cut the curve K into curve sections KA is particularly advantageous because the times TH of heartbeats can be determined particularly easily and reliably in a cardiogram KG and the curve K can be cut at or based on these times TH.

Preferably, the times TH of heartbeats are determined on the basis of the cardiogram KG and the curve K at these times TH is cut into curve sections KA. Preferably, each curve section KA starts at the time TH of one heartbeat and ends at the time TH of the immediately following next heartbeat.

Generally, however, the exact determination of the end of the curve sections KA is not decisive, since the curve sections KA serve in particular for an exact or reliable determination of the curve feature M. For this purpose, it is of primary importance to choose the time TH of a heartbeat as exactly as possible as the beginning of the curve section KA and/or to choose the same point relative to the time TH of the heartbeat for each curve section KA as exactly as possible.

Preferably, the curve sections KA are of equal length and/or the curve K is cut into curve sections KA that each have the same length. Preferably, the length of the curve sections KA corresponds to the average heart rate or corresponds to the duration between the times TH of two (immediately) consecutive heartbeats at this heart rate or corresponds hereto. It has been shown that this simplifies the determination of the usefulness or quality of curves K or curve sections KA and that the determination of blood pressure BP can be performed with higher accuracy.

The average heart rate is preferably, in particular arithmetic, the mean and/or median of the heart rate, in particular wherein the heart rate is determined by means of the cardiogram KG. The term "heart rate" means in particular the (average) number of heartbeats per unit of time, in particular per minute. For example, if the average heart rate is 120 bpm, this corresponds to an (average) duration of a heartbeat of 0.5 s or to an (average) interval of 0.5 s between two heartbeats.

The length L of a curve section KA is preferably determined by the formula $L=d_{HB}\cdot a$, wherein $d_{HB}$ is the average duration of a heartbeat, determined in particular on the basis of the average heart rate, and a is a factor which preferably has a value greater than or equal to 1. By means of the factor a, the length L of the curve section KA can also be selected to be greater than the average duration of a heartbeat. This has proven to be advantageous for determining the usefulness or quality of curves K or curve sections KA and for determining blood pressure BP.

The length of the curve sections KA can thus be or be selected independently of the concrete/respective duration between the times TH of two consecutive heartbeats.

Since, as described, the curve sections KA preferably each start at the time TH of a heartbeat and are of equal length, it is possible that the curve sections KA overlap and/or that segments of the curve K are contained in several curve sections KA. This is in particular the case if the length of a curve section KA is greater than the distance between two adjacent heartbeats.

Particularly preferably, the cardiogram KG is an electrocardiogram. In particular on the basis of an electrocardiogram, various characteristic structures, which can be assigned to or result from different phases of the heart's activity, can be identified. For the present method, the so-called QRS complex is particularly relevant.

In FIG. 9, different QRS complexes of a cardiogram KG are marked. One QRS complex preferably represents one heartbeat.

Preferably, the positions of one or more of the QRS complexes of the cardiogram KG are used to cut the curve K into curve sections KA. In particular, the QRS complexes of the cardiogram KG are used to determine the time TH of heartbeats, preferably wherein the curve K is cut into curve sections KA at the times TH determined by means of the QRS complexes. In other words, the QRS complexes or parts thereof are information by means of which cut the curve K is cut into sections KA.

A QRS complex preferably has three peaks, in particular a Q peak, an R peak and an S peak.

As Q peak is denoted the first, in particular negative or downward pointing, deflection or peak of the QRS complex.

As R peak is denoted the, in particular negative or downward pointing, deflection or peak of the QRS complex which follows the Q peak.

As S peak is denoted the, in particular positive or upward pointing, deflection or peak of the QRS complex which follows the R peak.

In particular, the position of the R peak or of the maximum of the R peak can be used as time TH of the heartbeat. This is shown by way of example in FIG. 9.

As an alternative to using the R peak as the time TH of the heartbeat, it is also conceivable to use another structure or another characteristic point of the cardiogram KG as the time TH of the heartbeat, for example the Q peak, the S peak, a midpoint or inflection point between two peaks, in particular the R peak and the S peak, or the like.

The determination of the R peaks or their positions is preferably done by means of a Pan-Tompkins plot of the cardiogram KG, in particular as explained in detail below.

For the determination of the R peaks, preferably all local peaks, in particular all local maxima of the Pan-Tompkins plot, are determined first.

As explained above, the cardiogram KG and thus also the Pan-Tompkins plot is preferably present as a set of discrete data points $d_i$, where d is the value of the Pan-Tompkins plot at position i. The index i counts through the data points $d_i$ and preferably corresponds to a time at which the respective data point $d_i$ was measured. In particular, a local maximum of the Pan-Tompkins plot is thus represented by a data point $d_i$ and/or some of the data points $d_i$ represent local maxima of the Pan-Tompkins plot.

A data point $d_i$ represents a local maximum in particular if $d_i > d_{i-1}$ and $d_i > d_{i+1}$ applies, i.e. if the value of the data point $d_i$ is greater than the value of the neighboring data points.

From the data points $d_i$ that represent local maxima, in a next step preferably only those are selected for which no data point with a higher value exists within a certain interval around the data point $d_i$. The interval preferably has a width of more than 200 ms, in particular more than 300 ms, and/or less than 600 ms, preferably less than 500 ms, in particular less than 400 ms. Particularly preferably, the interval has a width between 300 and 400 ms, for example about 372 ms.

For the peaks or data points $d_i$ of the Pan-Tompkins plot determined or selected in this way, the embrasure height or prominence is preferably determined.

Preferably, only those peaks or data points $d_i$ are selected or determined as R peaks of the Pan-Tompkins plot whose autonomous height or prominence is greater than or equal to a specified or specifiable threshold value.

The threshold value is preferably an adaptive threshold value. An adaptive threshold value in the sense of the present invention is preferably a threshold value which is not the same for all data points $d_i$ or which is different for different data points $d_i$. For example, an individual threshold value $t_i$ can be determined for each point of time i or each data point $d_i$. Preferably, the adaptive threshold value(s) $t_i$ is/are determined by determining and/or calculating the convolution between the Pan-Tompkins plot and a window function, in particular for each point i. The threshold value $t_i$ is then in particular the value of the convolution of the Pan-Tompkins plot with the window function at position i.

In principle, any window function can be used. Particularly preferably, the window function is a Blackman-Nuttall window. Preferably, a window width of 0.6 s and/or a gain factor of 3 is used. However, other values are also possible here.

Preferably, the position of the R peaks determined in this way is still corrected. It is, namely, possible that the positions of the R peaks in the Pan-Tompkins plot are slightly shifted compared with the positions of the R peaks in the original cardiogram KG and/or that shifts of the peaks result from the convolution with the window function. The positions of the R peaks determined by the Pan-Tompkins plot may therefore be "incorrect" or may differ from the positions of the R peaks in the raw signal of the cardiogram KG and/or the filtered cardiogram KG.

By correcting the positions of the R peaks, potential shifts caused by applying the filters to generate the Pan-Tompkins plot and/or inadvertently using the Q peak instead of the R peak are prevented. Correcting the positions of the R peaks is therefore conducive to the accurate determination of heartbeats, thus enabling a reliable or accurate examination of the animal T, in particular blood pressure.

The correction of the positions of the R peaks preferably takes place on the basis of the filtered and/or preprocessed cardiogram KG, but can also be based on the unprocessed cardiogram KG or, in other words, on the "raw signal" of the cardiogram KG.

Preferably, for the correction of the position of an R peak, starting from the position determined by means of the Pan-Tompkins plot, the position of this R peak is preferably searched for or determined in the cardiogram KG, in particular in the filtered and/or preprocessed cardiogram KG. This position in the cardiogram KG, in particular in the filtered and/or preprocessed cardiogram KG, is then preferably used as the position of the R peak and in particular replaces the position of the R peak determined by the Pan-Tompkins plot.

Particularly preferably, the gradient or the slope or the derivative of the cardiogram KG at the position of the R peak determined by means of the Pan-Tompkins plot is determined in the cardiogram KG, and on this basis the next maximum of the cardiogram KG is searched for and/or determined. Preferably, if the gradient or slope or derivative is positive, it is preferable to go right in the cardiogram KG and/or to examine the next data point in the cardiogram KG. If the gradient or slope or derivative is negative, it is preferable to go left in the cardiogram KG and/or to examine the previous data point. At this point, in particular at the next or previous data point, the gradient or slope or derivative of the cardiogram KG is preferably determined again and compared in particular with the previous value of the gradient or slope or derivative. These steps are preferably repeated until the position is found where the gradient or slope or derivative has a minimum value or amount. This position is then the position of the R peak.

In a more descriptive explanation, thus, based on the gradient, the cardiogram KG is sampled or scanned in the direction of the maximum until the gradient or its absolute value reaches the value zero and/or a minimum and thus the maximum of the cardiogram KG is found.

This method for determining the position of the maximum and/or R peak in the cardiogram KG has the advantage that the position can be calculated quickly and the corresponding algorithm is easy to implement, while at the same time the position is reliably determined.

However, other methods or algorithms are also conceivable for determining and/or correcting the position of the maximum and/or R peak in the cardiogram KG.

For example, the maximum value of the cardiogram KG can be determined in an interval around the position of the R peak determined by the Pan-Tompkins plot.

Alternatively, or additionally, the three highest peaks can be determined in an interval around the position of the R peak determined by the Pan-Tompkins plot and it can be checked whether the first and third of these peaks point in a different direction than the second or middle peak, i.e., the first and third peak represent a maximum and the second peak represents a minimum or vice versa (first and third peak represent minimum and second peak represents maximum). In the affirmative, the second or middle peak represents the R peak, so that its position is determined as the searched or corrected position of the R peak.

Generally, different methods for determining a maximum or R peak in the cardiogram KG are thus conceivable in order to correct the position of the R peak determined by the Pan-Tompkins plot.

The determination of the R peaks of the cardiogram KG is preferably performed after step S4. Alternatively, or additionally, however, the determination of the R peaks can also be performed before and/or during step S4, in particular the usefulness checking of the cardiogram KG.

Preferably, saturated sections of the cardiogram KG are removed, in particular for the purpose of determining the blood pressure BP and/or the pulse transit time PTT. A section is particularly saturated if the signal in the section assumes the maximum or minimum theoretically possible signal value. Saturated signals can occur, for example, if the paw 2 is moved and/or removed during the measurement.

Preferably, a saturated section of the cardiogram KG is removed if the section reaches or exceeds a certain minimum length. The minimum length is preferably more than 10 ms and/or less than 20 ms, for example 12 ms or 15 ms.

In addition, preferably (already determined) R peaks that fall below a temporal minimum distance from the saturated section, for example less than 200 ms or 100 ms before or after the saturated section, are removed from the cardiogram KG.

If a saturated section is removed from the cardiogram KG, a section of the curve K corresponding to the saturated section of the cardiogram KG is preferably also removed. A corresponding section in this sense means in particular a section of the curve K that was recorded or measured at the same time as the saturated section of the cardiogram KG.

Preferably, (already determined) R peaks are removed from the cardiogram KG, which are below a temporal minimum distance from an adjacent R peak. Here, it is preferred that both of the R peaks that are have less than the minimum distance are removed from the cardiogram KG.

The minimum distance is preferably determined or defined on the basis of a measure of dispersion of the distribution of the R peaks of the cardiogram KG, for example on the basis of the interquartile range or the standard deviation. In particular, the minimum distance is determined in such a way that those R peaks are removed which are too far below a mean or average distance of the R peaks.

For example, the minimum distance is defined or determined by the formula $MA = Q1 - f \cdot IQR$, wherein MA is the minimum distance, Q1 is the value of the lower quartile (0.25 quartile), IQR is the interquartile range, i.e. the difference between the upper quartile (0.75 quartile) and the lower quartile, and f is a factor that preferably has a value greater than or equal to 1, for example 1.5.

If R peaks or a section with R peaks is/are removed from the cardiogram KG, a section of the curve K corresponding thereto is preferably also removed. The corresponding section in this sense is understood to be, in particular, a section of the curve K that was recorded or measured at the same time as the section of the cardiogram KG that is removed from the cardiogram KG.

Step S5 can be performed multiple times and/or repeatedly, in particular if one or more of the previous steps S1, S2, S3 and/or S4 are performed multiple times and/or repeated. This is conducive to an accurate and reliable examination, in particular blood pressure determination, in particular if the animal T or the paw 2 is moved during the examination.

Step S6

The curve K is preferably filtered. This is preferably done at least partially already in the preprocessing device 30 assigned to the detector 6 and/or sensor 7. Alternatively, or additionally, the filtering can also be done before or after the formation of the curve sections KA. By filtering, disturbing influences, which lie in frequency ranges that are not due to effects caused by the pulse wave, can be eliminated in an advantageous way, whereby the parts of the curve K or the curve sections KA that comprise information about the arterial blood flow BF are selected. The filtering can be performed in connection with the present step S6 or even in advance, but is not mandatory.

Before further evaluation, in particular determination of a curve feature M by means of the curve sections KA, preferably some curve sections KA or a subset of the curve sections KA are selected and in particular the unselected curve sections KA are discarded.

Usually it is not possible to tell directly from the course of a curve section KA whether the curve section KA is useful or not. This is in particular apparent from the curve shown in FIG. 9, which at first sight might seem chaotic and might seemingly not contain any useful information. Here, it is to be stressed that the curve K depicted in FIG. 9 is not a randomly chosen curve K but corresponds to a photoplethysmogram actually measured on a cat.

In the context of the present invention, however, it has turned out in a surprising way that a reliable determination of the curve feature M can nevertheless be achieved by the proposed measures, preferably in combination. In particular, by the selection and/or rejection of curve sections KA, motion artifacts can be compensated for, so that the examination can be carried out and, in particular, the blood pressure BP can be reliably determined even if the animal T or the paw 2 moves during the examination with the sensor device 4, in particular relative to the sensor device 4.

Particularly preferably, a selection of curve sections KA on the basis of certain criteria explained in more detail below is performed. In particular, the usefulness of the curve K or the curve sections KA can be assessed and the result of the evaluation can be improved by discarding unusable curve sections KA.

In particular, a more precise determination of the curve feature M can be achieved if unusable curve sections KA are sorted out or discarded or are no longer considered.

The curve sections KA are preferably checked for usefulness, in particular by means of check criteria. Preferably, useful curve sections KA are selected and/or unusable curve sections KA are discarded. Discarded curve sections KA are not used for further evaluation.

Preferably, a subset of (usable) curve sections KA is selected for further evaluation and a subset of (not usable) curve sections KA is discarded.

The check of curve sections KA for usefulness in particular constitutes a check of the usefulness of the curve K from which the curve sections KA were generated. The rejection of individual curve sections KA of a curve K or the rejection of a subset of curve sections KA of a curve K therefore in particular constitutes a partial rejection of the curve K. Similarly, a rejection of all curve sections KA of a curve K constitutes a rejection of the (complete) curve K.

Alternatively, or additionally, potentially suitable curve sections KA are selected or chosen on the basis of the check of curve sections KA for usefulness. Selected or chosen curve sections KA are used for further evaluation. Not selected or chosen curve sections KA, however, are not used as a basis for further evaluation, i.e., they are discarded.

The curve sections KA that are checked for usefulness and are selected or discarded can originate from different curves K. In this case, it is possible that the curve sections KA originate from different curves K which were successively recorded with the same sensor 7 and/or detector 6.

Alternatively, or additionally, it is possible that the curve sections KA originate from curves K which were—simultaneously or successively—recorded with different sensors 7 and/or detectors 6.

Preferably, one or more criteria are checked during the check for the usefulness of a curve section KA. The curve section KA is preferably useful if one, several or all of the criteria explained below are fulfilled.

According to a first criterion, preferably the amplitude of the first extremum, in particular the amplitude of the absolute maximum, of the curve section KA is determined. If the amplitude of the first extremum or its absolute value is greater than or equal to a specified or specifiable threshold value, the criterion is preferably considered fulfilled. Otherwise, the criterion is preferably considered not fulfilled.

As an alternative or in addition to the amplitude of the first extremum, according to the first criterion the peak-to-peak amplitude of the curve section KA can be determined and preferably compared with a specified or specifiable threshold value. The peak-to-peak amplitude is the difference between the values of an absolute maximum and an absolute minimum of the curve section KA. If the peak-to-peak amplitude or its absolute value is greater than or equal to a specified or specifiable threshold value, the criterion is preferably considered fulfilled. Otherwise, the criterion is preferably considered not fulfilled.

Through the first criterion, in particular curve sections KA having a particularly flat course can be discarded. It has been shown that such curve sections KA do not contain any useful information and that in particular an exact or reliable determination of a maximum and thus a pulse transit time PTT and/or other curve features M is particularly difficult. Therefore, the accuracy and/or reliability of the evaluation is improved if such curve sections KA are discarded.

According to a second criterion, it is preferably checked whether a reasonable value for a curve feature M, in particular the pulse transit time PTT, results or can result from the curve section KA. In particular, to this end, the position of the first, preferably absolute, maximum of the curve section KA is determined, which preferably corresponds to the pulse transit time PTT. The criterion is considered fulfilled if this position is greater than or equal to a lower specified or specifiable threshold value and/or less than or equal to an upper specified or specifiable threshold value. Otherwise, the criterion is considered not fulfilled.

Here, the lower threshold value preferably corresponds to a minimum pulse transit time PTT and/or the upper threshold value to a maximum pulse transit time PTT.

In this way, curve sections KA can be rejected that lead to biologically, physically or anatomically unrealistic, in particular too low and/or too high, pulse transit times PTT. Because of biological, physical or anatomical principles, the pulse transit time PTT can only be within a certain interval. For example, there is a certain minimum time between the heartbeat and the arrival of the pulse wave caused by the heartbeat at a certain location in an artery A. Therefore, very small pulse transit times PTT that are below the lower threshold value are not realistic. On the other hand, an upper threshold value can be used, which corresponds to a pulse transit time PTT that is not realistic to reach or exceed.

For a domestic cat for an examination at the (fore-)paw 2, for example, the lower threshold value can be defined as 20 ms and/or the upper threshold value can be defined as 175 ms. For other animal species or body parts, however, other threshold values and/or minimum and/or maximum pulse transit times PTT may be reasonable or specifiable.

According to a third criterion, the course of the curve K in the curve section KA is preferably examined or checked. For this purpose, the curve K is in particular smoothed and the first derivative of the preferably smoothed curve K as well as the zeros of the first derivative are calculated. The criterion is considered fulfilled if the number of zeros of the first derivative of the, preferably smoothed, curve K is at least 2 and/or at most 4 and the slope of the first derivative of the curve K or the second derivative of the curve K at the first position of the first zero of the first derivative is negative. Otherwise, the criterion is considered not fulfilled.

By the third criterion, it is in particular checked whether the curve K essentially has a wave-like course with a distinct maximum and a distinct minimum, wherein first a maximum and then a minimum is assumed. Such an "optimal" course is shown as an example in FIG. 12 on the right.

The first, second and third criteria are preferably absolute criteria, i.e. criteria for which a curve section KA is considered or analyzed or checked for usefulness in isolation, in particular without considering other curve sections KA in this check.

The further criteria explained below are preferably relative criteria, i.e. criteria for which the usefulness of a curve section KA is checked by taking other curve sections KA into account and/or by comparison with other curve sections KA or with results determined on the basis of other curve sections KA, such as mean values.

According to a fourth, fifth and/or sixth criterion it is preferably checked as to whether a certain curve section KA deviates too much from other curve sections KA. In particular, the fourth to sixth criterion serves to sort out or discard extreme outliers.

The fourth, fifth and/or sixth criterion is preferably checked for each curve K and/or for each sensor 7 and/or detector 6 separately. In particular, only curve sections KA that are assigned to the same curve K and/or the same sensor 7 and/or detector 6 are taken into account or used when checking a curve section KA of the fourth, fifth and/or sixth criterion.

In the fourth, fifth and/or sixth criterion, the curve sections KA are preferably scaled, in particular normalized. This allows the curve sections KA, in particular those selected in step S5, to have the same amplitudes, mean values, maxima and minima and/or peak-to-valley values. This makes it easier to compare the curve sections KA.

Subsequently, a curve mean value KM is preferably determined from the curve sections KA, i.e. a mean value of the course of the curve sections KA. The curve mean value KM is in particular the mean or average course of a curve section KA or the curve K in a curve section KA. In particular, the curve mean value KM is determined by calculating the mean value of the curve sections KA for the respective point in time of the curve sections KA or at this point in time. This mean value is preferably the arithmetic mean or the median, but can also be another mean value.

As an illustration, the averaging of the curve sections KA or the determination of the curve mean value KM preferably corresponds to a superimposition of the curve sections KA and a subsequent determination of the average course of the superimposed curve sections KA.

An averaging on the basis of several curve sections KA in this sense is shown graphically in FIG. 12 as an example, wherein on the left side in FIG. 12 different curve sections KA are shown, in the middle in FIG. 12 the curve sections KA were superimposed and on the right side in FIG. 12 the curve mean value KM determined from the curve sections KA is shown.

In another view, the curve mean value KM is the sum or superposition of the curves K or curve sections KA.

The curve sections KA are preferably each present in the form of individual data points $$\left(t_i^{(KA_j)}, k_i^{(KA_j)}\right).$$

Preferably, the j-th curve section KA is thus represented by the data points $$\left(t_i^{(KA_j)}, k_i^{(KA_j)}\right).$$

or consists of it. Here, i is an index that counts the data points.

Here, $$t_i^{(KA_j)}$$

is in particular the x-coordinate of the i-th data point $$\left(t_i^{(KA_j)}, k_i^{(KA_j)}\right).$$

The x-coordinate or the quantity $$t_i^{(KA_j)}$$

is referred to in the following as the position of the i-th data point. The position $$t_i^{(KA_j)}$$

preferably corresponds to the time of the data point $$\left(t_i^{(KA_j)}, k_i^{(KA_j)}\right),$$

in particular, thus to the (temporal) distance of the data point $$\left(t_i^{(KA_j)}, k_i^{(KA_j)}\right)$$

from the beginning of the curve section KA.

Further, $$k_i^{(KA_j)}$$

is in particular the y-coordinate of the i-th data point, i.e., in particular the value or measured value of the curve section KA at the position $$t_i^{(KA_j)}.$$

The y-coordinate or the quantity $$k_i^{(KA_j)}$$

is referred to in the following as the value of the i-th data point.

For the formation of the curve mean value KM, the values $$k_i^{(KA_j)}$$

present for a certain position or a certain point in time $$t_i^{(KA_j)}$$

are added together. The result is preferably normalized. The curve mean value KM thus preferably consists of data points $$\left(t_i^{(KM)}, k_i^{(KM)}\right),$$

in particular wherein $$k_i^{(KM)}$$

is the arithmetic mean of the values $$k_i^{(K)}$$

of the curve sections KA at the position or at the time $$t_i^{(KM)}.$$

Preferably, therefore $$k_i^{(KM)} = \frac{1}{m}\sum_{j=1}^{m} k_i^{(KA_j)}$$

with m being the number of curve sections KA.

Analogous to the designation of the quantities $$t_i^{(KA_j)}, k_i^{(KA_j)}$$

of data points of a curve section KA, preferably the quantity $$t_i^{(KM)}$$

is referred to as the position of the i-th data point of the curve mean value KM and the quantity $$k_i^{(KM)}$$

is referred to as the value of the i-th data point of the curve mean value KM.

After the determination of the curve mean value KM, an, in particular empirically determined, correlation coefficient (also called product-moment correlation coefficient), in particular the Pearson correlation coefficient or Pearson product-moment correlation coefficient, of the curve section KA to be checked for usefulness with the mean curve section is calculated for the curve section KA to be checked. The criterion is considered fulfilled if the correlation coefficient reaches or exceeds a specified or specifiable threshold value. Otherwise, the criterion is considered not fulfilled. For example, the threshold value can be 0.5.

The correlation coefficient is preferably calculated using the formula:

$$r_j = \frac{\sum_{i=1}^{n} \left(k_i^{(KM)} - \overline{k}^{(KM)}\right)\left(k_i^{(KA_j)} - \overline{k}^{(KA_j)}\right)}{\sqrt{\sum_{i=1}^{n}\left(k_i^{(KM)} - \overline{k}^{(KM)}\right)^2 \sum_{i=1}^{n}\left(k_i^{(KA_j)} - \overline{k}^{(KA_j)}\right)^2}}$$

with $\overline{k}^{(KM)} = \frac{1}{n}\sum_{i=1}^{n} k_i^{(KM)}$ and $\overline{k}^{(KA_j)} = \frac{1}{n}\sum_{i=1}^{n} k_i^{(NA_j)}$.

Here, $r_j$ is the correlation coefficient of the j-th curve section KA, $\overline{k}^{(KM)}$ is the mean value, in particular the arithmetic mean, of the values $$k_i^{(KM)}$$

of the curve mean value KM, $$\overline{k}^{(KA_j)}$$

is the mean value, in particular the arithmetic mean, of the values $$k_i^{(KA_j)}$$

of the j-th curve section KA, and n is the number of data points of a curve section KA.

In the fourth criterion, preferably a deviation of the distance between two extrema of a curve section KA compared to the distance between the extrema of the remaining curve sections KA is examined. The distance between two extremes or peak-to-peak distance is understood here in particular as the temporal distance or the distance of the positions of the, in particular absolute, extrema, in particular thus the distance of the extrema on the x-axis. As can be seen, for example, from FIG. 12, the curve sections KA preferably each have two absolute extrema, in particular an absolute maximum and an absolute minimum. The distance between the extrema is in particular the difference between the position PM2 of the minimum and the position PM1 of the maximum, or the absolute value of this difference.

In particular, in the fourth criterion, for each curve section KA the distance of the extrema (peak-to-peak distance) and a lower quartile (0.25-quartile), an upper quartile (0.75-quartile) and the interquartile range, i.e. the difference between the upper quartile and the lower quartile, the peak-to-peak distances or the distribution of the peak-to-peak distances. The criterion is preferably considered fulfilled if the peak-to-peak distance of the curve section KA to be examined reaches or exceeds an upper specified or specifiable threshold value and/or reaches or falls below a lower specified or specifiable threshold value. The upper threshold value is preferably the sum of the upper quartile or its position and the product of a factor f and the interquartile range, i.e. UTV=Q3+f·IQR, wherein UTV is the upper threshold value, Q3 is the upper quartile or its position and IQR is the interquartile range. The lower threshold value is preferably the difference between the lower quartile or its position and the product of a factor f and the interquartile range, i.e. LTV=Q1−f·IQR, wherein LTV is the lower threshold value, Q1 is the lower quartile or its position and IQR is the interquartile range. The factor f is preferably greater than 1 and particularly preferably has the value 1.5.

According to the fourth criterion, in particular those curve sections KA can be sorted out or discarded which (compared to other curve sections KA) have a particularly large and/or a particularly small peak-to-peak distance.

In the fifth criterion, preferably a deviation of the variance or sample variance of the values $$k_i^{(KA_j)}$$

of a curve section KA compared to the variance of the values of the other curve sections KA is examined.

In particular, in the fifth criterion, the variance or sample variance of the values $$k_i^{(KA_j)}$$

and a lower quartile (0.25-quartile), an upper quartile (0.75-quartile) and the interquartile range, i.e. the difference between the upper quartile and the lower quartile, of the variances or the distribution of the variances are calculated for every curve section KA.

The variance of the values of the j-th curve section KA is preferably calculated by the formula $$V = \frac{1}{n} \sum_{i=1}^{n} \left( k_i^{(KA_j)} - \bar{k}^{(KA_j)} \right)^2$$

$$\text{with } \bar{k}^{(KA_j)} = \frac{1}{n} \sum_{i=1}^{n} k_i^{(KA_j)},$$

wherein V denotes the variance. In the formula for V, instead of the factor $$\frac{1}{n}$$

before the sum also the factor $$\frac{1}{n-1}$$

can be used.

The fifth criterion is preferably considered fulfilled if the variance of the values of the curve section KA to be examined reaches or exceeds an upper specified or specifiable threshold value and/or reaches or falls below a lower specified or specifiable threshold value. The upper threshold value is preferably the sum of the upper quartile or its position and the product of a factor f and the interquartile range. The lower threshold value is preferably the difference between the lower quartile or its position and the product of a factor f and the interquartile range. The factor f is preferably greater than 1 and has the value 1.5, which is particularly preferred.

According to the fifth criterion, in particular curve sections KA can be sorted out or rejected, whose values show a particularly large and/or a particularly small variance.

In the sixth criterion, preferably the difference between the curve section KA and the curve mean value KM is calculated, in particular thus for each position $$t_i^{(KA_j)}$$

the difference $$k_i^{(KA_j)} - k_i^{(KM)}.$$

Subsequently, the spectral power density for a specified or specifiable frequency range, for example 15 Hz to 40 Hz, is calculated for the resulting curve or difference curve. The criterion is considered fulfilled if the integral over the spectral power density over this frequency range is smaller or equal to a specified or specifiable threshold value. Otherwise, the criterion is considered not fulfilled.

By selecting curve sections KA on the basis of the described criteria, it is preferably possible to determine the curve feature M on the basis of a maximum of 200, preferably a maximum of 100, in particular a maximum of 60, particularly preferably a maximum of 45, particularly preferably a maximum of 30 heartbeats or curve sections KA. This, in turn, makes it possible to keep the time required to measure or record the curve(s) K and/or the cardiogram KG as short as possible.

All or a part of the criteria can be applied. Alternatively, or additionally, other criteria can be used to check the curve K or the curve sections KA for usefulness.

The curve section KA is preferably discarded and/or not used for the further evaluation if the or one of the explained criteria is not fulfilled. If the curve section KA fulfills all or all applied criteria, the curve section KA is preferably selected or used for further evaluation.

Preferably, a curve section KA is only selected if it meets all of the criteria explained. In principle, however, other methods are also possible in which only one or some of the criteria explained is/are checked and/or a curve section KA is selected even if only one or some of the criteria is/are fulfilled. Alternatively, or additionally, other criteria than those described may be provided.

Alternatively, or additionally, the result of a measurement with the force sensor 18A and/or the scale 18 can be taken into account for the evaluation of the usefulness of a curve section KA or for the usefulness check. For example, a low measurement value can be an indication that the animal T or a paw 2 is not correctly positioned on the sensor device 4 and the curve section KA is discarded accordingly.

By checking the usefulness of curve sections KA and/or by selecting useful curve sections KA and/or discarding unusable curve sections KA, the number of curve sections KA required for the evaluation and thus the measuring time can be reduced or minimized. This is advantageous to make the examination as fast and pleasant as possible and thus stress-free for the animal T. This is in particular beneficial for an accurate and reliable examination, in particular blood pressure determination. Also the probability of a meaningful measurement between movements of the animal T is increased.

The number of required curve sections KA is reduced in particular by the fact that the variation or dispersion of curve sections KA is reduced by discarding unusable curve sections KA. In particular, this improves the statistics.

If there is a wide variation or dispersion of measurements, i.e. if the measurement results are very different, a particularly high number of measurements is required to determine a reliable mean value or the like. The better the measurements are in accordance, the fewer measurements are needed for good statistics. In this way, sorting out unusable curve sections KA leads, in a synergistic way, to fewer curve sections KA being required for evaluation from the outset.

The step S6 can be performed multiple times and/or repeatedly, in particular if one or more of the preceding steps S1, S2, S3, S4 and/or S5 are performed multiple times and/or repeatedly. This is conducive to an accurate and reliable examination, in particular blood pressure determination, in particular if the animal T or the paw 2 is moved during the examination.

In particular, it is possible to return to one of the steps S1, S2, S3 and/or S4 if it is found in step S6 that too many curve sections KA of one or more sensors 7 and/or in total too many curve sections are unusable or do not meet/fulfill the usefulness criteria or too few of the curve sections are useful or meet/fulfill the usefulness criteria.

By returning to a previous step, it is in particular made possible that the animal T moves during the examination or that the paw 2 is moved during the examination. Measurement errors and/or movement artifacts generated hereby can be compensated by discarding unusable curves K or curve sections KA, in particular in connection with a multiple presence detection and/or selection of sensors 7 and/or multiple recording of cardiograms KG and/or curves K. In particular, it is possible that during or after a movement of the animal T or the paw 2, the examination is sustained or continued with one or more other sensors 7 or a different subset of sensors 7 than before the movement. The fact that the animal T can preferably move freely during the examination makes the examination very pleasant and stress-free for the animal T. This is conducive to an accurate and reliable examination, in particular blood pressure determination.

Step S7

In step S7, averaging is preferably performed on the basis of several curve sections KA. In particular, only the curve sections KA selected or not discarded in step S6 are used for this averaging.

An "averaging" in this sense is in particular the determination of an average or mean course of a set of several curve sections KA or an average or mean course of the curve K during a heartbeat.

During averaging, in particular a curve mean value KM is determined. The averaging or determination of the curve mean value KM from curve sections KA is preferably carried out as already described above in step S6. For the determination of the curve mean value KM, preferably the values $$k_i^{(KA_j)}$$

present for a certain position or for a certain point in time $$t_i^{(KA_j)}$$

of the curve sections KA are thus added together. The result is preferably normalized. The curve mean value KM thus preferably consists of data points $$\left(t_i^{(KM)}, k_i^{(KM)}\right),$$

in particular wherein $$k_i^{(KM)}$$

is the arithmetic mean of the values $$k_i^{(K)}$$

of the curve sections KA at the position or at the time $$t_i^{(KM)}.$$

Preferably, therefore $$k_i^{(KM)} = \frac{1}{m} \sum_{j=1}^{m} k_i^{(KA_j)},$$

wherein m is the number of curve sections KA.

In particular, in step S7 only those curve sections KA selected or not discarded in step S6 for the determination of the curve mean value KM or the curve mean values KM are used. While the method for determining a curve mean value KM from curve sections KA is thus preferably identical in step S6 and S7, the curve mean value(s) KM determined in step S6 and the curve mean value(s) KM determined in step S7 differ in that different quantities of curve sections KA are used or taken as a basis for determining the curve mean value KM.

To determine the curve mean value KM, the curve sections KA are preferably scaled and/or normalized, in particular so that all curve sections KA used to determine the curve mean value KM have the same value range, for example from −1 to 1 or similar.

Preferably, a resampling method is used in step S7. For this purpose, so-called subsamples are preferably generated from the curve sections KA.

In a resampling method, statistical properties of sample statistics, such as a mean value, a variance, a measure of dispersion or the like, can be determined on the basis of a repeated drawing of subsamples from an initial sample.

The resampling method can, for example, be a bootstrap method, a jackknife method, a cross-validation or a permutation test or randomization test. Particularly preferably, however, the resampling method is a bootstrap method in the present invention. In the following, the bootstrap method is explained in more detail.

When using the bootstrap method, the subsample can also be called bootstrap sample. In particular, the term "subsample" used in the following in connection with the bootstrap method is also interchangeable with the term "bootstrap sample".

In the present method, the initial sample is preferably formed by the entirety of the curve sections KA—possibly selected in step S6—, in particular one or more curve(s) K and/or sensors 7. In particular, the initial sample has N curve sections KA. N is therefore the number of curve sections KA in the initial sample.

The initial sample preferably has only curve sections KA of the same curve K or the same sensor 7.

The basic principle of the proposed bootstrap method is to create one or more subsamples from the initial sample, i.e. in this case the curve sections KA, by "drawing with replacement".

A subsample is created by selecting M curve sections KA from the N curve sections KA of the initial sample.

The number M of curve sections KA of the subsample preferably corresponds to the number N of curve sections KA of the initial sample (M=N).

In particular, the selection of the M curve sections KA is random. The curve sections KA that are selected for the subsample are preferably selected independently from each other. This means that the first of the M curve sections KA for generating a subsample is randomly selected from the N curve sections KA of the initial sample. Then, a further curve section KA is selected from the N curve sections KA of the initial sample. In particular, the further curve section KA is selected from the same set of curve sections KA as the first curve section KA. Afterwards, further curve sections KA are selected in the same way from the same set of curve sections KA until M curve sections KA have been selected.

In other words, curve sections KA that have already been selected once from the initial sample to generate the subsample, are taken into account again when selecting further curve sections KA, so that the subsample can contain the same curve section KA several times. This means that curve sections KA that have already been selected once for the generation of the subsample can also be selected again for subsequent drawings of curve sections KA from the initial sample.

From a statistical or probability theory point of view, this corresponds to a "sampling with replacement", wherein—as an illustration—curve sections KA are "drawn" from a set of curve sections KA one after the other and are "put back" again before drawing the next curve sections KA. The drawing of a curve section KA is therefore always made from the same set of curve sections KA. This means that the same curve section KA can be drawn several times during several drawings and curve sections KA cannot be drawn at all.

With the present method, it is therefore in principle possible in extreme cases that a subsample comprises the same curve section KA M times. It is also possible, in principle, that the subsample does not have the same curve section KA twice, so that the subsample corresponds exactly to the initial sample.

Usually, however, a subsample will contain some curve sections KA of the initial sample several times and some curve sections KA of the initial sample will not be contained at all.

Preferably, less than 1000, preferably less than 500, in particular less than 250, particularly preferably less than 100, very particularly preferably less than 75, and/or more than 10, preferably more than 30, particularly preferably about 50, subsamples are generated.

Usually, when using resampling methods or bootstrap methods, a very large number of subsamples is generated, for example 1000 or more subsamples. Generally, the accuracy and/or reliability of sampling functions can be increased by increasing the number of subsamples generated.

With the number of subsamples, however, the computational effort required for the generation and evaluation of curves K or curve sections KA increases, too. This has a negative effect on the one hand on the energy consumption of the system used for the execution of the method, in particular the examination apparatus 1, and on the other hand on the computing capacity and/or computing time needed for the execution of the method. It is therefore advantageous to keep the number of generated subsamples as low as possible.

In the context of the present invention it has been shown in a surprising way that with the aforementioned relatively small number of subsamples a sufficiently reliable and/or exact result, in particular a curve feature M, can already be achieved or determined.

However, if very little computing power is available, it may also be possible or preferable to generate an even smaller number of subsamples, for example less than 30, in particular only 15. Tests have shown that meaningful results can be achieved already with such a small number of subsamples.

The number of subsamples created or to be created is preferably fixed. In particular, the same number of subsamples is thus generated for each analysis of a curve K or curve sections KA, for example for curves K successively recorded and/or curves K measured with different sensors 7.

In step S7, a curve mean value KM is preferably determined by means of the curve sections KA of the initial sample.

Preferably, as described above under step S6, the curve mean value KM of the curve sections KA is determined, wherein each curve section KA of the initial sample is included exactly once in the calculation of the curve mean value KM.

Preferably, a curve mean value KM is also determined from the subsamples (each), in particular in the same way as for the initial sample. For this purpose, each of the M curve sections KA of a subsample is considered exactly once when calculating the curve mean value KM of the bootstrap sample. In this sense, the M curve sections KA of the subsample represent different curve sections KA, even if some of the M curve sections KA—due to a multiple selection of these curve sections KA from the initial sample when generating the subsample—should be identical.

In other words, the averaging on the basis of several curve sections KA can in particular be performed taking into account subsamples. In particular, the curve mean value KM is determined for each of the subsamples and preferably also for the initial sample.

As mentioned above, the initial sample preferably has only curve sections KA that originate from the same curve K and/or were measured with the same sensor 7 and/or detector 6. However, it is also possible that the initial sample may have curve sections KA that were measured with different sensors 7 and/or detectors 6, in particular successively and/or time-shifted. This may be the case in particular if the animal T moved during the examination or recording of one or more curves K or the paw 2 was moved and/or thereupon one or more sensors 7 were selected again, in particular another subset of sensors 7.

Basically it is advantageous to use a resampling method or bootstrap method, but not mandatory.

Step S8

In the step S8, a curve feature M is preferably determined. The determination of the curve feature M is based in particular on the curve mean value(s) KM determined in step S7.

Preferably, the curve feature M is thus determined on the basis of the curve sections KA and/or the subsamples.

For this purpose, several curve features M, preferably of the same kind, can be determined first, of which a curve feature M is formed or selected at the end of step S8. This curve feature M selected and/or formed at the end of step S8 is referred to as the curve feature M determined in step S8.

The determination of the curve feature M can be done separately for each curve K or each sensor 7 and/or detector 6. In particular, only curve sections KA that originate from the same curve K or different curves K of the same sensor 7 and/or detector 6 are taken into account for the determination of curve feature M. However, other methods are also possible here.

Particularly preferably, the curve feature M is determined for the initial sample and for each subsample, in particular of a curve K and/or of a sensor 7 and/or detector 6.

It is therefore particularly preferred to determine the same curve feature M for each of the curve mean values KM determined previously, in particular in step S7. From these same curve features M, which can in principle take a different value for each curve mean value KM, a curve feature mean value is preferably calculated, in particular the arithmetic mean of the curve features M.

Since the curve mean values KM are preferably determined separately for each sensor 7 and/or detector 6, i.e., when calculating a curve mean value, preferably only curve sections KA are used which were measured with the same sensor 7 and/or detector 6, the calculation of the curve feature mean value is preferably performed separately for each sensor 7 and/or detector 6. In this way, a curve feature mean value is preferably available for each sensor 7 and/or detector 6. Preferably, (at the end of step S8) one of these curve feature mean values is selected, whereby in particular a sensor 7 and/or detector 6 is selected. This selected curve feature mean value is referred to as the curve feature M determined in step S8.

In principle, however, it is also possible that curve sections KA of curves K that were measured with different of the sensors 7 and/or detectors 6 are used to calculate a curve mean value KM. Here, the curve sections KA measured with different sensors 7 and/or detectors 6 can be taken from curves K measured simultaneously or, Alternatively, or additionally, from curves K measured successively and/or with a time delay.

The curve feature M is preferably a feature of the curve K or a curve section KA. The curve feature M is preferably a feature that is related to a pulse waveform delay PTT and/or a blood pressure BP and/or is correlated with a pulse waveform delay PTT and/or a blood pressure BP. Alternatively, or additionally, the curve feature M can correspond to a course of curve mean value. In particular, the curve feature M is a feature that can be used to determine the blood pressure BP.

In the following, some characteristics of the curve K or the curve section KA that can represent a curve feature M are explained by way of example. However, further characteristics or characteristics other than those explained below can also represent a curve feature M.

Furthermore, the determination of the curve feature M is explained below with the aid of a curve mean value KM. In principle, however, it is also possible to do without the determination of a curve mean value KM or the curve mean values KM and to determine the curve feature M directly using a curve section KA. In this case, the curve feature M is preferably determined separately for each curve section KA and preferably a curve feature mean value is determined from this subsequently.

Particularly preferably, the curve feature M is or corresponds to the pulse transit time PTT.

Preferably, the pulse transit time PTT corresponds to a time or a position PM1 of an extremum, in particular a maximum, of a curve mean value KM.

FIG. 12 shows an example of a curve mean value KM or its course. The curve mean value KM is preferably wavelike. In particular, the curve mean value KM has two successive extrema, in particular an (absolute) maximum and an (absolute) minimum, particularly preferably wherein first the maximum and then the minimum is assumed.

The time or position PM1 of the maximum of the curve mean value KM preferably corresponds to the pulse transit time PTT. The curve feature M is therefore preferably the position PM1 of the maximum of the curve mean value KM.

In particular, the time or position PM1 of the maximum of the curve mean value KM corresponds to the pulse transit time PTT, if the curve section start point corresponds to the time TH of the heartbeat. If, as explained at the beginning, the curve K has been cut on the basis of the cardiogram KG at times corresponding to the times TH of heartbeats, the pulse transit time PTT can thus be read off directly. Otherwise, a correction can be made based on the time difference between the beginning of the curve and the heartbeat, or the later intended blood pressure determination can take place on the basis of a relative pulse transit time PTT. Thus, the pulse transit time PTT does not necessarily have to be the absolute value of the time difference between heartbeat and arrival of the pulse wave at the measurement location, but can also only (directly) correspond thereto.

Alternatively, or additionally to the determination of the pulse transit time PTT, the pulse wave velocity can be determined. The pulse wave velocity is the quotient of the distance travelled by the pulse wave and the pulse transit time PTT required to travel this distance. In particular, the pulse wave velocity can be used instead of the pulse transit time PTT as a variable in a correlation function F to determine the blood pressure BP from the pulse transit time PTT and/or can be considered in the correlation function F in addition to the pulse transit time PTT.

Alternatively, or additionally, the curve feature M is the time or position PM2 of the first and/or absolute minimum of the curve mean value KM.

Alternatively, or additionally, the curve feature M is the time or position of a maximal negative slope of the curve mean value KM. In this case, the curve mean value KM is preferably smoothed first and the curve feature M or the position of the maximal negative slope is determined using this smoothed curve mean value KM. Preferably, a smoothing filter such as a von-Hann window is used to smooth the curve mean value KM. The position of the maximal negative slope is between the absolute maximum and the absolute minimum in the illustration example according to FIG. 12.

Alternatively, or additionally (preferably instead of the position of the maximal negative slope), the absolute value of the maximal negative slope is used. In this case, the curve mean value KM is preferably smoothed first and the curve feature M or the value or absolute value of the maximal negative slope is determined using this smoothed curve mean value KM. Preferably, a smoothing filter such as a von-Hann window is used to smooth the curve mean value KM.

Alternatively, or additionally, the curve feature M is the distance or time difference between the position of PM1 of the absolute maximum and the position PM2 of the absolute minimum.

Alternatively, or additionally, the curve feature M is the distance between the positions at which the second derivative of the curve mean value KM takes a (local) maximum in each case. This distance corresponds to the distance between the positions where the curve mean value KM has the strongest curvatures.

Alternatively, or additionally, the curve feature M is an instantaneous harmonic phase shift. This is preferably determined as follows: A, preferably discrete, Fourier transformation is applied to the curve mean value KM. Subsequently, the phase of the first harmonic oscillation and the phase of the second harmonic oscillation are calculated, in particular by calculating the real and imaginary part of the arctangent of the Fourier transform of the curve mean value KM. The difference between the phase of the first harmonic oscillation and the phase of the second harmonic oscillation is referred to as instantaneous harmonic phase shift.

Alternatively, or additionally, the curve feature M is a section ratio. The section ratio is the ratio between the length of different sections of the curve mean value KM. For this purpose, first a first and a second section of the curve mean value KM are determined. Preferably, the first section starts at the position of the first zero of the first derivative of the curve mean value KM and the first section ends at the position of the second zero of the first derivative of the curve mean value KM. Preferably, the second section starts at the position of the first zero of the second derivative of the curve mean value KM or at the position of the first maximum of the first derivative of the curve mean value KM, respectively, and the second section ends at the position of the second zero of the first derivative of the curve mean value KM. Preferably, the quotient of the length of the first segment and the length of the second segment is formed.

Alternatively, or additionally, the curve feature M is a curviness of the curve K or the curve section KA. This is shown in particular in FIG. 15.

Figure 15:
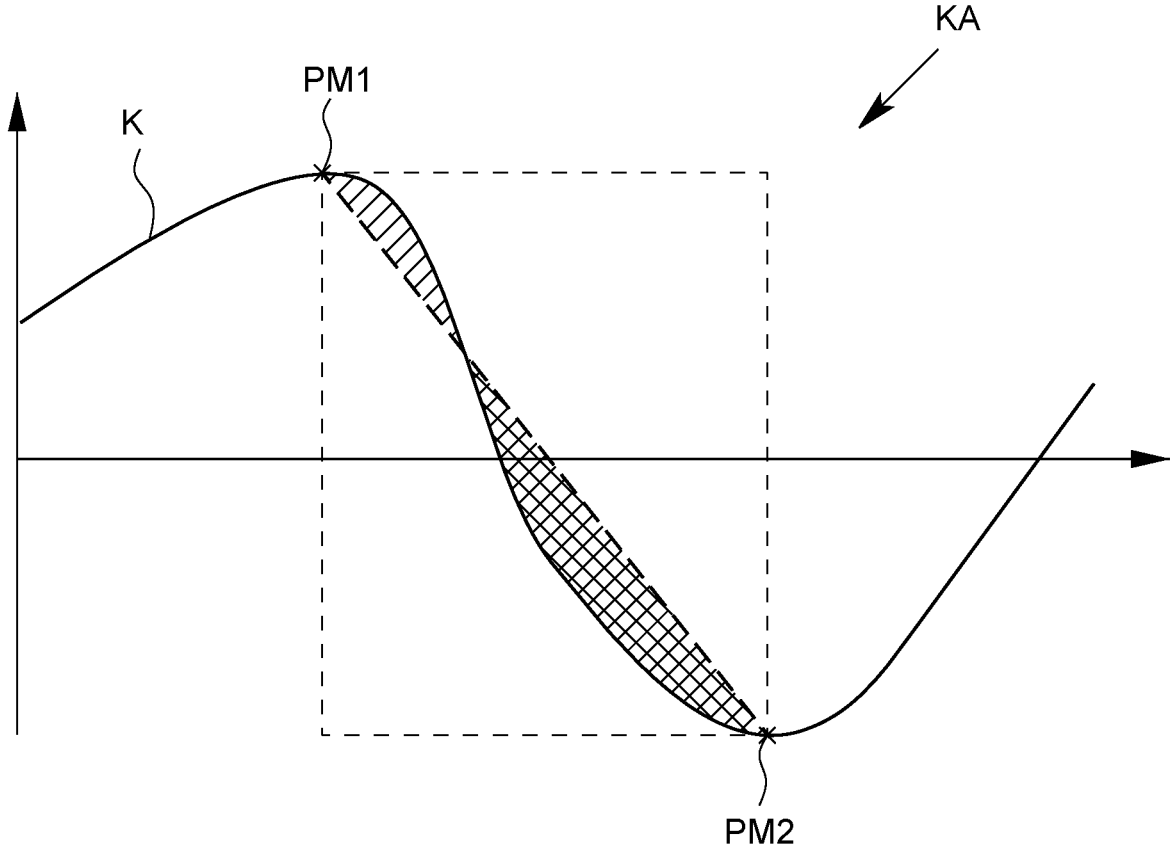
FIG. 15 is an illustration for explaining the calculation of
a curviness of a curve.

The curviness of the curve K is in particular a measure of how much the curve K deviates from a straight line in the curve section KA, in particular between the position PM1 of the first maximum and the position PM2 of the first minimum For determining the curviness, preferably the area of the surface that the curve K includes between the position PM1 of the first maximum and the position PM2 of the first minimum with a straight line running from the first maximum to the first minimum is determined. The surface may consist of several unconnected sections, as shown in FIG. 15, where the surface consists of two sections, namely the single hatched section above the straight line and the double hatched section below the straight line. This enclosed surface is preferably normalized to or divided by the area of a rectangle which extends from the first maximum to the first minimum and/or of which the first maximum and the first minimum of the curve K form two opposite corner points, as shown in particular in FIG. 15. The line from the first maximum to the first minimum preferably forms a diagonal of the rectangle. The sides of the rectangle run parallel to the x-axis and y-axis.

The curviness is thus in particular the quotient of the surface or area which the curve encloses, between the first maximum and the first minimum, with a straight line running from the first maximum to the first minimum, and the area of a rectangle of which the sides are parallel to the x-axis and y-axis and of which the straight line from the first maximum to the first minimum forms a diagonal.

To determine the curviness it is possible to count the areas or surfaces (single hatched in FIG. 15) that lie above the straight line with a positive sign and to count the areas or surfaces (double hatched in FIG. 15) that lie below the straight line with a negative sign. In this case, for example, the curviness would have a value of 0 if the enclosed surfaces above and below the straight lines each had the same area.

Alternatively, or additionally, it is however possible to determine the absolute curviness, which is a measure for the deviation of the curve K from a straight line. For the determination of the absolute curviness, preferably the absolute values of the areas of all surfaces that are enclosed between the curve K and the straight line running from the first maximum to the first minimum are added in order to determine the surface or area enclosed between straight line and the curve K. In other words, these areas preferably enter with the same sign. Thus, when calculating the absolute curviness, it is preferably not taken into account whether the surfaces are above or below the straight line.

The determination of the absolute curviness is particularly preferred.

Alternatively, or additionally, the curve feature M is the position or x-coordinate of the intersection point between a horizontal or straight line passing through the first maximum with a zero slope and a straight line or tangent through the point of greatest gradient between the first maximum and the first minimum, the tangent having the slope of the curve K or the curve section KA at that point. This point of intersection is also called tangent intersection point for short.

In summary, the curve feature M is therefore preferably one or a combination of several of the following values of the curve mean value KM:

the position PM1 of the first maximum or pulse transit time PTT, the position PM2 of the first minimum, the distance between the position PM1 of the first maximum and the position PM2 of the first minimum, the position of the maximal negative slope, the distance of the positions where the second derivative takes local maxima, the value or absolute value of the maximal negative gradient the instantaneous harmonic phase shift, the section ratio, the curvature of the curve K, the tangent intersection point.

The curve feature M is preferably checked for plausibility. In particular, it is checked whether the curve feature M exceeds a specified or specifiable upper threshold value and/or falls below a specified or specifiable lower threshold value. This was explained in more detail above using the example of the pulse transit time PTT, which can only lie within certain intervals due to anatomical conditions. Similarly, for curve features M other than the pulse transit time PTT, corresponding threshold values can be specified, the falling below or exceeding of which is not plausible, for example due to anatomical, biological and/or physical laws.

This plausibility check of the curve feature M includes in particular the check of the position PM1 of the first maximum and/or the determined pulse transit time PTT for plausibility. If a measure of dispersion, especially the interquartile range, of the position PM1 of the first maximum and/or the pulse transit time PTT reaches or exceeds a specified or specifiable upper threshold value, the curve K or the sensor 7 and/or detector 6 with which the curve K was recorded is preferably discarded or not selected. For example, the threshold value can be 5 ms or correspond to a measure of dispersion, in particular interquartile range, of the pulse transit time PTT of 5 ms. In this way, curves K or sensors 7 and/or detectors 6 in particular can be discarded or not selected for which no consistent or uniform pulse transit time PTT can be determined on the basis of the curve sections KA.

Preferably, only a single one of the various curve features M explained above is determined, in particular for each curve mean value KM, and preferably used for the determination of the blood pressure BP. However, it is also possible that several of the curve features M, in particular for each curve mean value KM, are determined and preferably used for the determination of the blood pressure BP.

Preferably, a curve feature mean value, in particular the arithmetic mean of the curve features M, is determined from the curve features M of the initial sample and the sub-samples. The curve feature mean value is therefore in particular the mean value, preferably the arithmetic mean, of the curve feature M of the initial sample and the curve features M of the subsamples.

Particularly preferably, thus, one of the previously explained curve features M is determined for the initial sample as well as for each of the subsamples and subsequently a mean value of these curve features M is determined.

Preferably, a measure of dispersion of the curve features M is also determined, in particular an interquartile range, a standard deviation and/or an (empirical) variance. The measure of dispersion and/or the interquartile range, the standard deviation and/or the (empirical) variance is assigned to the curve feature mean value.

A measure of dispersion is in particular a measure that represents the dispersion of values, in this case in particular the dispersion of the curve features M of the initial sample and the subsamples.

The interquartile range of the curve features M is in particular the distance between the lower quartile (0.25 quartile) and the upper quartile (0.75 quartile). The inter-quartile range is therefore preferably the width of the interval in which the middle 50% of the determined curve features M lie. In principle, however, a different quantile range can also be used.

As an alternative to the interquartile range, the measure of dispersion can also be a variance, in particular empirical variance, and/or standard deviation. However, the use of the interquartile range has proven to be very robust and therefore particularly advantageous.

Preferably, for each curve K or each sensor 7 and/or detector 6, a measure of dispersion assigned to this curve K or this sensor 7 and/or detector 6 is determined separately. In particular, thus, only those curve features M are taken into account in the determination of a measure of dispersion that are assigned to the initial sample and the subsample of the same curve K or the same sensor 7 and/or detector 6.

The curve feature M is preferably determined separately for each sensor 7 and/or detector 6. In particular, thus, only curve mean values KM of a single sensor 7 and/or detector 6 are used for the determination of the curve feature M.

As a result, for each sensor 7 and/or detector 6 a curve feature mean value assigned to this sensor 7 and/or detector 6 can thus be determined separately.

In particular, the determined values of the curve features M and/or curve feature mean values of the different sensors 7 and/or detectors 6 may differ.

Preferably, one of the curve feature mean values is subsequently selected. In particular, one of the sensors 7 and/or detectors 6 and/or one of the curves K is selected hereby.

The selection of the curve feature mean value and/or the curve K and/or the sensor 7 and/or detector 6 is preferably based on or under consideration of the measure of dispersion determined (in step S8), in particular the interquartile range, the (empirical) variance and/or the standard deviation.

One possibility to select a curve feature mean value and/or a curve K and/or a sensor 7 and/or detector 6 is to select the curve feature mean value that has the lowest measure of dispersion, in particular the lowest interquartile range, the lowest (empirical) variance and/or the lowest standard deviation.

A further possibility, which has proved to be particularly preferred in the context of the present invention, is to use, in addition to the measure of dispersion or interquartile range, the amplitude of the maxima of the curve mean values KM of the initial sample and/or subsamples in order to select a curve feature mean value.

In this case, it is preferred to proceed as follows—in particular for each sensor 7 and/or detector 6 separately:

First, as described above, for each subsample and preferably for each initial sample the curve feature M, in particular the pulse transit time PTT, and possibly one or more further curve features M are determined. Then, the curve feature(s) M is/are checked for plausibility, as described above—separately for each subsample and preferably the initial sample. If the curve feature M is plausible or if all tested curve features M are plausible, the respective sample is considered plausible overall. In addition, the amplitude of the curve mean value KM of the respective sample, in particular the value of the first maximum, is determined.

Furthermore, the interquartile range of the curve features M, in particular pulse transit times PTT, determined for the individual samples or subsamples is preferably determined ("IQR"). In addition, the mean value or median of the amplitudes or values of the first maximum of the curve mean values KM of the individual samples or subsamples is determined ("meanA"). Moreover, the number of samples or subsamples that were considered plausible overall is determined ("num_S_plausible").

From these values IQR, meanA and num_S_plausible, the value of $$L = \frac{IQR}{meanA \ num\_S\_plausible},$$

i.e., the quotient of the interquartile range IQR and the product of the amplitude mean value or median meanA and the number num_S_plausible of plausible samples, is preferably determined, in particular for each detector 6 and/or sensor 7 of which the curves were evaluated.

In this way, a value L can be assigned separately to each sensor 7 and/or detector 6.

Preferably, the curve feature mean value is then selected to which the smallest value L corresponds. Since the curve feature mean value was preferably determined on the basis of curves K or curve sections KA of a single sensor 7, this selection preferably corresponds to the selection of a sensor 7.

If the amplitude mean value or amplitude median meanA is less than or equal to a specified or specifiable threshold value, the curve K and/or the sensor 7 and/or detector 6 with which the curve K was measured is preferably discarded and/or not selected. The threshold value can have the value 0.2, for example. As explained above, normalized curve sections are preferably used to determine the curve feature M and/or the curve mean values KM, so that the amplitude or value of the first maximum in each curve section KA is 1. Accordingly, the amplitude mean or amplitude median meanA is a measure of how well the positions and/or courses or shapes of the first maximum of the curve sections KA match in a (plausible) sample, because if the positions and/or courses or shapes of the first maximum would match perfectly, the amplitude mean or median meanA would have the value 1 and the value is the lower the more the positions and/or courses or shapes of the first maximum vary.

If the proportion of subsamples for which the determination of the curve feature M leads to a realistic pulse transit time PTT is less than or equal to a specified or specifiable threshold value, the curve K and/or the sensor 7 and/or detector 6 with which the curve K was measured is preferably discarded and/or not selected. A realistic pulse transit time PTT is preferably a pulse transit time PTT that is greater than or equal to a lower threshold value, for example 20 ms, and/or less than or equal to an upper threshold value, for example 175 ms, as explained above. The threshold value for the proportion of subsamples where the determination of the curve feature M leads to a realistic pulse transit time PTT can have the value 0.8, for example. In particular, this means that a curve K and/or a sensor 7 and/or detector 6 is discarded and/or not selected if the proportion of subsamples that lead to a realistic pulse transit time PTT is less than or equal to 80%.

The curve feature mean value selected, preferably taking into account the measure of dispersion and/or the amplitude of the maximum or the maxima of the curve mean values KM of the initial sample and/or subsamples, is preferably the curve feature M determined in step S8.

As a result, it is preferred that a curve feature M to be used for the determination of blood pressure BP, in particular a curve feature mean value, is selected from several, previously (preferably for different sensors 7) determined curve features M or curve feature mean values (the curve features M or curve feature mean values in particular being of the same kind).

The selection can be made from curve features M or curve feature mean values that each correspond to one detector 6 and/or sensor 7. Alternatively, or additionally, the selection can be made from curve features M or curve feature mean values that have been determined in connection with the previous step S7 by using subsamples.

Alternatively, or additionally, the selection can be made from curve features M or curve feature mean values that have been formed by combining curve sections KA of different sensors 7 and/or detectors 6. However, it is also possible that only one curve feature M or curve feature mean value is determined and used in the following.

The selection of curve features M or curve feature mean values in step S8 thus in particular constitutes a selection of a sensor 7 and/or detector 6. This is shown as an example in FIG. 11. For the sake of clarity, only steps S3 and S8 are shown in FIG. 11, in which a selection of sensors 7 and/or detectors 6 is or can be made. However, this does not mean that steps S4 to S7 are necessarily omitted. As shown in FIG. 11, preferably both the preselection of sensors 7 and/or detectors 6 in step S3 and the selection of curves K or curve features M or curve feature mean values in step S8 constitute a selection of sensors 7 and/or detectors 6.

The selection of sensors 7 is therefore preferably done in several steps, in particular in step S3 and step S8. Preferably, (in particular in step S3) a (first) selection of sensors 7 is made before the optical examination, in particular photoplethysmography, and/or recording of the curve(s) K with the sensor device 4. Further preferably (Alternatively, or additionally, in particular in step S3), a (further) selection of sensors 7 is made after the optical examination, in particular photoplethysmography, and/or recording of the curve(s) K with the sensor device 4. If in step S6 all curve sections KA of the curve(s) K of a sensor 7 should be discarded, this is preferably also a selection of sensors 7, in particular that is to say that in this case only those sensors 7 are selected whose curve sections KA are not completely discarded.

Preferably, a curve K and/or a sensor 7 and/or detector 6 with which the curve K was recorded is discarded and/or not selected if, after the usefulness check of the curve sections KA explained in step S6, the number of remaining and/or not discarded curve sections KA of the curve K is less than or equal to a specified or specifiable threshold value. The threshold value can be 30, for example, so that curves K with 30 or less useful curve sections KA are rejected and/or not selected. This step of rejecting and/or not selecting curves K with too few useful curve sections KA does not necessarily take place only in step S8, but can also take place after step S6 and/or before step S7 or as a partial step of one of the steps S6 and S7. Preferably, the averaging in step S7 is only carried out with curves K that have sufficient useful curve sections KA or where the number of useful curve sections KA is greater than or equal to the above-mentioned threshold value.

In particular, it is possible to return to one of the steps S1, S2, S3 and/or S4 if it is found in the step S8 that the determined curve feature M or several or all of the determined curve features M is/are too inaccurate or unreliable, for example because the determined value L is too small or a measure of dispersion assigned to the curve feature(s) M is too large.

In particular, by returning to a previous step, it is made possible that the animal T to moves during the examination or the paw 2 is moved during the examination. Measurement errors and/or movement artifacts generated hereby can be compensated by discarding unusable curves K or curve sections KA, in particular in connection with a multiple presence detection and/or selection of sensors 7 and/or a multiple recording of cardiograms KG and/or curves K. In particular, it is possible that during or after a movement of the animal T or the paw 2, the examination is sustained or continued with one or more other sensors 7 or a different subset of sensors 7 than before the movement. The fact that the animal T can preferably move freely during the examination makes the examination very pleasant and stress-free for the animal T. This is conducive to an accurate and reliable examination, in particular blood pressure determination.

Step S9

In step S9, preferably a, in particular systolic, diastolic and/or mean, blood pressure BP is determined, in particular from the curve feature M determined in step S8. The blood pressure BP is preferably determined using a preferably empirically determined correlation function F.

The correlation function F therefore preferably represents a link between the curve feature(s) M determined, in particular in step S8, and the blood pressure BP or assigns a blood pressure BP to the curve feature M.

In particular, the correlation function F preferably does not explicitly take account of the arm length or leg length between the paw 2 and the heart of the animal T. In other words, it is preferably not necessary to determine the arm length or leg length explicitly.

Rather, in the context of the present invention it has been shown in a surprising way that for different animals T of the same species or breed, in particular for different domestic cats, the same correlation function F can be used and leads to meaningful results. However, preferably different correlation functions F are used for different animal species or breeds.

The correlation function F is preferably determined by means of a study in which the blood pressure BP is determined by means of an established method for determining the blood pressure BP and is assigned to the curve feature M determined by means of the method according to the invention. The correlation function F is then determined by adapting parameters of the correlation function F in such a way that the blood pressure BP determined by means of the method according to the invention at least substantially corresponds to the blood pressure BP determined by means of the established method.

The correlation function F is preferably a scalar field dependent on at least two variables.

Preferably, the curve feature M, in particular the pulse transit time PTT, constitutes a variable of the correlation function F.

It is preferred that in addition to the curve feature M, in particular the pulse transit time PTT, a heart rate constitutes a variable of the correlation function F. The heart rate describes the number of heartbeats in a certain time interval and is preferably determined from the cardiogram KG, in particular from the distance of QRS complexes or R peaks.

The correlation function F can thus, for example, take the functional form $$F(x,y)=a \cdot x+b \cdot y+c$$

wherein x represents the curve feature M, in particular the pulse transit time PTT and/or position PM1 of the first maximum, y represents the heart rate and a, b, and c are parameters to be determined.

Furthermore, the correlation function F can depend on further variables. Particularly preferably, the distance between the position PM1 of the first maximum and the position PM2 of the first minimum of a curve section KA or the curve mean value KM constitutes a further variable of the correlation function F.

The correlation function F can therefore also take the functional form $$F(x,y)=a \cdot x+b \cdot y+c \cdot z+d$$

wherein x represents the curve feature M, in particular the pulse transit time PTT and/or position PM1 of the first maximum, y represents the heart rate, z represents the distance between the position PM1 of the first maximum and the position PM2 of the first minimum, and a, b, c and d are parameters to be determined.

Furthermore, the correlation function F is preferably a nonlinear function. The correlation function F can thus depend in a nonlinear way on the curve feature M and/or the heart rate, in particular it can thus have higher order terms in x, y and/or z (such as $x^2$, $x^3$, $y^2$, $y^3$, $z^2$, $z^3$ etc.).

Furthermore, the correlation function F can be dependent on further variables or more than three variables x, y, z.

In particular, it is possible to take into account, in the determination of the blood pressure BP or as a variable in the correlation function F, the curviness of the curve K as an alternative or in addition to the already mentioned quantities It has been shown that, in particular in animals T from the subfamily of Felinae, for example cats, it is possible that changes in blood pressure BP alternatively or in addition to the pulse transit time PTT cause the curviness of the curve K to change. In other words, in some cases the blood pressure BP may be reflected in the curviness of the curve K, in particular without a changed blood pressure BP resulting in a changed pulse transit time PTT, so that it may be important to consider the curviness of the curve K as an alternative or in addition to the pulse transit time PTT in the correlation function F or in the determination of the blood pressure BP.

Various correlation functions F for the determination of a blood pressure from a pulse transit time and/or heart rate are described in M Sharma et al., Cuff-Less and Continuous Blood Pressure Monitoring: A Methodological Review, Technologies 2017, 5(2), 21. The correlation function F of the present invention may have the functional form of one of the mathematical models described there in chapters 3 and 4, in particular according to one of equations (6) to (10) or according to Table 3.

In the correlation function F, in particular its parameters, various other characteristics of the animal T can be taken into account Alternatively, or additionally, for example the size, weight, sex, age and/or a color and/or pigmentation of the paw(s) 2 or the pads of paw(s) 2.

In principle, the correlation function F can also depend on anatomical peculiarities of the respective animal T. For example, it may be provided that the size of the animal T and/or a measure corresponding to the size of the animal T, for example the body length, the shoulder height, a leg or arm length or any other parameter corresponding to a distance between the heart and the paw 2, is taken into account in the correlation function F, in particular in the form of one of the parameters a, b, c or d. A preferred parameter in this context may also be the weight of the animal T, since in many cases this allows to draw sufficiently accurate conclusions about the distance between heart and paw 2. In this respect, the correlation function F can thus have the weight of the animal T as a parameter or the weight of the animal T can be taken into account by one of the parameters a, b, c, d.

Complementarily, a parameter corresponding to the body fat percentage, such as the bioimpedance, can be taken into account. A respective measurement can be made using the electrodes 15 for determining the cardiogram KG and/or the scale 18. Especially the combination of the bioimpedance with the weight of the animal T can, taken into account in the correlation function F by implicit or actual conclusions about anatomical peculiarities of the animal T with regard to the distance between heart and paw 2, make possible a more reliable determination of the blood pressure BP from the curve feature M.

Taking into account properties of the animal T such as height, weight, body fat percentage or the like is preferably done in the correlation function F in the form of parameters (a, b, c, d) instead of variables (x, y, z). In other words, the respective property does not directly enter the correlation function F as a variable, but preferably only as a parameter or indirectly.

Preferably, the properties of the animal T are taken into account in the form of discrete parameters. A discrete parameter in this sense is in particular a parameter that can take a fixed number of different values, for example two, three or four different values. This makes it possible to take into account a property of the animal to be examined in the correlation function F without this property being explicitly included as a variable in the correlation function F.

In particular, a classification of the animal T into different groups according to a property such as height, weight, body fat percentage or the like can be made, wherein the property is taken into account in the correlation function F by using a discrete parameter, each of the different values of the parameter corresponding to one of the different groups.

It may be provided that the classification of the animal T and the selection between the possible discrete parameter values coming along therewith is done automatically. Alternatively, or additionally, it is possible that the classification of the animal T is done by a manual input or the like, in particular by an input at the examination apparatus 1 and/or before the examination or measurements are performed.

Particularly preferably, in one of the parameters of the correlation function F, in particular the parameter a linked to the curve feature M, the size and/or weight of the animal T, in particular the cat, is taken into account. Preferably, this is done in the form of a binary parameter. A binary parameter is in particular a parameter which can only take two different values. In other words, preferably two different values a1 and a2 are provided for the parameter a, wherein for large and/or heavy animals T the value a1 is used as parameter a in the correlation function F and for small and/or light animals T the value a2 is used as parameter a in the correlation function F. The subdivision into large and/or heavy animals T and small and/or light animals T is preferably done by means of a limit value, wherein if the limit value is exceeded, the animal T is classified as large and/or heavy animal and if the limit value is fallen below, the animal T is classified as small and/or light animal. Here, the limit value is preferably a value corresponding to the size and/or the weight of the animal T, such as for example an arm and/or leg length, a shoulder height, a total length of the animal T, the weight of the animal T or the like.

Preferably, the systolic and/or diastolic blood pressure BP is/are determined. Different correlation functions F are preferably used for the systolic and diastolic blood pressure BP, wherein the different correlation functions F preferably have the same functional form or depend on the same variables and/or differ only in the values of the parameters (a, b, c, d).

It is expressly pointed out that the method and/or the examination apparatus according to the present invention can in particular be used for the determination of the diastolic blood pressure as well. This has been shown in studies during the development of the present invention.

The blood pressure BP determined from the curve feature (s) M by means of the correlation function F can be output or transmitted, for example output or transmitted to the external device 23, for example to a mobile device, a smartphone, a server or a database or the like. Alternatively, or additionally, the determined blood pressure BP can be displayed using the examination apparatus 1, in particular the display device 19.

SUMMARY

Figure 13:
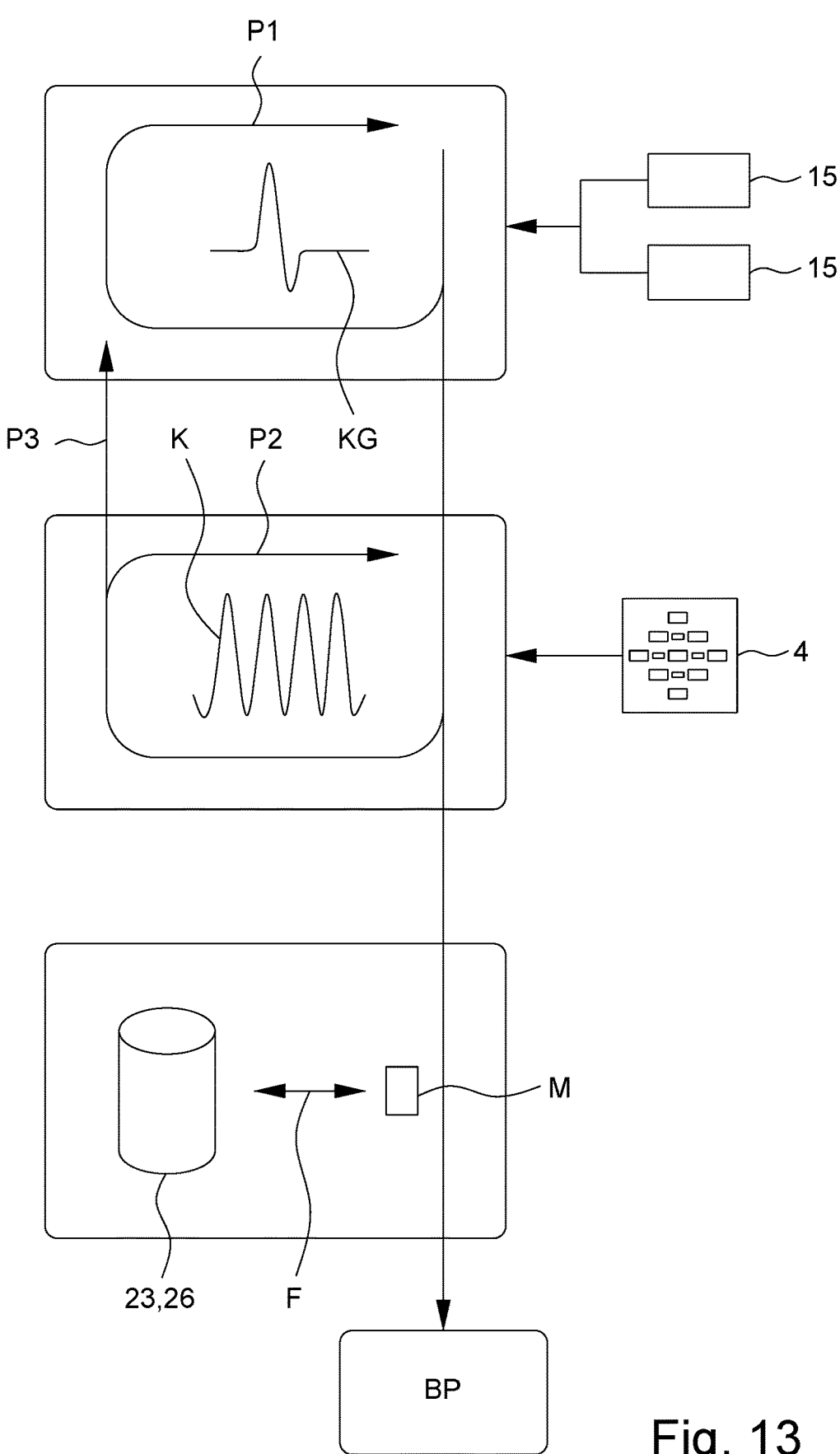
FIG. 13 is a further schematic representation of a
sequence of a method according to the invention.

In FIG. 13, the method according to the proposal or some steps of the method according to the proposal are again summarized graphically.

Preferably, a cardiogram KG is recorded. In particular, the cardiogram KG is an electrocardiogram and/or the cardiogram KG is recorded using the electrodes 15 of the examination apparatus 1.

Preferably, a usefulness check of the cardiogram KG is performed before any further measurement and/or evaluation. In particular, it is checked here whether heartbeats can be reliably identified in the cardiogram KG and/or whether the cardiogram KG contains useful information. The usefulness check of the cardiogram KG is preferably carried out on the basis of a cardiogram KG with a length of a few seconds and/or on the basis of a cardiogram KG which has or represents several heartbeats, for example between 5 and 10 heartbeats.

If the cardiogram KG is not useful or does not fulfill/meet the criteria of the usefulness check, a new cardiogram KG is preferably recorded. This is symbolized in FIG. 13 by the arrow P1.

In addition, a curve K comprising information about an arterial blood flow BF of animal T is preferably recorded. This is done in particular with the sensor device 4. The curve K is preferably recorded simultaneously with the cardiogram KG.

Preferably, the curve K is checked for usefulness. If the curve K is not useful, a new curve K is preferably recorded. This is symbolized in FIG. 13 by the arrow P2. Alternatively, or additionally, a new cardiogram KG can be recorded or the measurement of the cardiogram KG and/or the curve K can be started again. This is symbolized in particular by the arrow P3.

Subsequently, the curve K is preferably evaluated, in particular taking into account information from the cardiogram KG. For this purpose, the curve K is preferably cut into curve sections KA at times TH, wherein the times TH were determined on the basis of the cardiogram KG and correspond in particular to positions from its QRS complex, preferably the R peaks.

From the cardiogram KG and/or the curve K, a blood pressure BP is preferably determined. This is preferably done by determining at least one curve feature M from the curve K and determining the blood pressure BP from the curve feature M by means of a preferably empirical correlation function F.

The correlation function F can be preset, in particular stored in the storage medium 26 of the examination apparatus 1 or in the external device 23.

The blood pressure BP can be output, in particular with the display device 19 and/or the external device 23.

Further aspects of the present invention which are realizable independently or in combination with the aspects and features described above are in particular:

1. Method for medical examination, in particular determination of a blood pressure BP, of an animal T, in particular an animal T having a paw 2, particularly preferably an animal T from the subfamily of the Felinae, wherein a curve K comprising information about the arterial blood flow BF of the animal T, in particular a photoplethysmogram, is recorded, characterized in that the curve K is cut into several curve sections KA in such a way that each curve section KA corresponds to a heartbeat.

2. Method according to aspect 1, characterized in that for the evaluation an averaging is carried out on the basis of several curve sections KA and/or a curve mean value KM is determined from several curve sections KA.

3. Method according to aspect 1 or 2, characterized in that a subset of the curve sections KA is selected for evaluation, in particular wherein one or more curve sections KA are discarded.

4. Method according to one of the preceding aspects, characterized in that a resampling method, in particular bootstrap method, is used for evaluation, wherein subsamples, in particular bootstrap samples, are generated from the curve sections KA.

5. Method according to aspect 4, characterized in that a subsample has less than 200, preferably less than 100, in particular less than 60, and/or more than 15, preferably more than 30, particularly preferably about 45, curve sections KA.

6. Method according to aspect 4 or 5, characterized in that less than 1000, preferably less than 500, in particular less than 250, particularly preferably less than 100, very particularly preferably less than 75, and/or more than 10, preferably more than 30, particularly preferably about 50, bootstrap samples are generated.

7. Method according to one of the preceding aspects, characterized in that one or more curve features M, in particular a pulse transit time PTT and/or a value corresponding thereto or correlated therewith, is or are determined from the curve sections KA and/or subsamples.

8. Method according to aspect 7, characterized in that for each subsample the curve feature M, in particular the pulse transit time PTT, is determined and/or an mean value and/or curve feature mean value is calculated from curve features M, in particular pulse transit times PTT, in particular for each subsample and preferably an initial sample.

9. Method according to aspect 7 or 8, characterized in that a measure of dispersion of the curve feature M and/or curve feature mean value, in particular the pulse transit time PTT, in particular an interquartile range, is determined.

10. Method according to one of the preceding aspects, characterized in that several curves K are recorded simultaneously and/or successively, a measure of dispersion is determined for each of the curves K and, on the basis of the measure of dispersion, one of the curves K is selected for further evaluation, in particular determination of the blood pressure BP.

11. Method according to one of aspects 7 to 10, characterized in that the blood pressure BP is determined by means of a preferably empirically determined correlation function F from the curve feature M, in particular the pulse transit time PTT.

12. Procedure according to one of the preceding aspects, characterized in that a cardiogram KG is recorded simultaneously with the curve K.

13. Method according to aspect 12, characterized in that the curve K is cut into curve sections KA by means of information from the cardiogram KG.

14. Method according to aspect 12 or 13, characterized in that QRS complexes of the cardiogram KG, in particular the positions of R peaks of QRS complexes, are used to determine times TH of heartbeats, preferably wherein the curve K is cut into curve sections KA at the times TH determined by means of the QRS complexes.

15. Method according to one of the aspects 12 to 14, characterized in that the cardiogram KG is automatically checked for usefulness, wherein if the cardiogram KG is not usable, the cardiogram KG and curve K are discarded and a new cardiogram KG and a new curve K are recorded.

16. Method according to one of the preceding aspects, characterized in that the curve K or its curve sections KA is/are automatically checked for usefulness, wherein, if the curve K is not usable, the curve K is discarded and a new curve K is recorded.

17. Method according to one of the preceding aspects, characterized in that several curves K are recorded and curve sections KA from different of the several recorded curves K are used for evaluation.

18. Method for medical examination, in particular determination of a blood pressure BP, of an animal T, in particular an animal T having a paw 2, from the subfamily of the Felinae, particularly preferably an animal T from the subfamily of the Felinae, preferably where the method is designed according to one of the above aspects, wherein an arterial blood flow BF of the animal T is optically examined, in particular a photoplethysmography is performed, with a sensor device 4, wherein the sensor means 4 has one or more emitters 5 of the same kind for emitting electromagnetic radiation R and a plurality of detectors 6 of the same kind for detecting the radiation emitted by the emitter 5, so that the emitter/s 5 and the detectors 6 form a plurality of sensors 7 of the same kind, characterized in that a sensor 7 or a subset of sensors 7 is selected.

19. Method according to aspect 18, characterized in that the sensors 7 each have a sensor region 11, the sensor regions 11 of the sensors 7 each being located at different locations and together forming a sensing region 12, so that with each sensor 7 a different partial region of the sensing region 12 is sensed, a specific partial region of the sensing region 12 being selected for the medical examination.

20. Method according to aspect 18 or 19, characterized in that a presence determination is carried out, in particular wherein it is checked whether an animal T or a paw 2 is located on an examination apparatus 1 used for carrying out the method and/or above a sensor device 4 in such a way that the optical examination can be carried out by means of the examination apparatus 1 and/or sensor device 4.

21. Method according to one of the aspects 18 to 20, characterized in that a position determination is carried out, in particular wherein it is checked and/or determined above which sensors 7 of the sensor device 4 the paw 2, in particular a pad, is located and/or with which of the sensors 7 the optical examination can be carried out.

22. Method according to one of the aspects 18 to 21, characterized in that it is checked whether a paw 2 is located in a sensor region 11 of a sensor 7, wherein for this check a signal S measured with the sensor 7 is analyzed, in particular an absolute signal strength is examined for exceeding or falling below a threshold value.

23. Method according to one of the aspects 18 to 22, characterized in that a selection of a sensor 7 or a subset of sensors 7 is made before carrying out the optical examination with the sensor device 4 and/or before a curve K is recorded with the sensor device 4.

24. Method according to one of aspects 18 to 23, characterized in that a selection of a sensor 7 or a subset of sensors 7 is made after carrying out the optical examination with the sensor device 4 and/or after a curve K has been recorded with the sensor device 4, in particular by selection of a subset of curves K recorded with different sensors 7.

25. Method according to one of the preceding aspects, characterized in that curves K comprising information about an arterial blood flow BF, in particular photoplethysmograms, are recorded with the sensors 7, wherein at least one of the curves K is selected for evaluation, preferably wherein a quality of the recorded curves K is determined by means of a statistical analysis and the curve K with the highest quality is selected for evaluation.

26. Method according to one of the preceding aspects, characterized in that a curve K selected for evaluation is divided into curve sections KA, wherein a subset of the curve sections KA of the selected curve K is used for evaluation.

27. Method according to one of the preceding aspects, characterized in that several curves K are recorded successively and the curves K are divided into curve sections KA, wherein curve sections KA of curves K successively recorded with the same sensor 7 are used for evaluation.

28. Method according to one of the preceding aspects, characterized in that several curves K are recorded simultaneously and the curves K are divided into curve sections KA, wherein curve sections KA of curves K recorded simultaneously with different sensors 7 are used for evaluation.

29. Method according to one of the preceding aspects, characterized in that a curve feature M and/or curve feature mean value, in particular a pulse transit time PTT or a value corresponding thereto or correlated therewith, is determined by means of the curve K.

30. Method according to one of the preceding aspects, characterized in that by means of the curve K several different curve features M and/or curve feature mean values are determined, preferably wherein the different curve features M and/or curve feature mean values are or represent different features of the same curve K.

31. Method according to aspect 29 or 30, characterized in that the blood pressure BP is determined from the curve feature(s) M and/or curve feature mean value(s), in particular the pulse transit time PTT, by means of a preferably empirically determined correlation function F.

32. Method according to one of the preceding aspects, characterized in that the curves K are each cut into curve sections KA which correspond to a heartbeat, wherein a mean value is calculated from several curve sections KA, preferably wherein a cardiogram KG is recorded simultaneously with the curves K, wherein the curves K are cut into curve sections KA by means of information from the cardiogram KG.

33. Method according to one of the preceding aspects, characterized in that a diastolic blood pressure BP is determined.

34. Examination apparatus 1 for medical examination, in particular determination of a blood pressure BP, of an animal T, in particular an animal T having a paw 2, particularly preferably an animal T from the subfamily Felinae, with a sensor device 4 for the optical examination of an arterial blood flow BF of the animal T, in particular for performing a photoplethysmography, wherein the sensor means 4 has one or more emitters 5 of the same kind for emitting electromagnetic radiation R and a plurality of detectors 6 of the same kind for detecting the radiation R emitted by the emitter(s) 5 so that the emitter(s) 5 and the detectors 6 form a plurality of sensors 7 of the same kind, characterized in that the examination apparatus 1 has a control device 25 which is designed to select a sensor 7 or a subset of the sensors 7.

35. Examination apparatus according to aspect 34, characterized in that the sensors 7 each have several emitters 5.

36. Examination apparatus according to aspect 34 or 35, characterized in that the emitters 5 are each part of several sensors 7.

37. Examination apparatus according to one of the aspects 34 to 36, characterized in that each sensor 7 has a sensor region 11, the sensor regions 11 of the sensors 7 each being located at different locations and together forming a sensing region 12, so that each sensor region 11 forms a different partial region of the sensing region 12 and different partial regions of the sensing region 12 can be selected by means of the control or control device 25.

38. Examination apparatus according to one of the aspects 34 to 37, characterized in that the examination apparatus 1 and/or control device 25 is designed to carry out a method according to one of the aspects 1 to 33 and/or in that the examination apparatus 1 and/or control device 25 is designed to determine a diastolic blood pressure.

39. Examination apparatus 1 for carrying out a medical examination, in particular a photoplethysmography, preferably where the examination apparatus 1 is designed according to one of the aspects 35 to 38, with at least one emitter 5 for emitting electromagnetic radiation R and at least one detector 6 for detecting the radiation R emitted by the emitter 5, wherein the examination apparatus 1 has means adapted to execute the steps of the method according to any one of aspects 1 to 33.

40. Computer program comprising instructions which, when executed, cause the examination apparatus 1 to execute the steps of the method according to any one of aspects 34 to 39.

41. Computer-readable storage medium 26, having stored thereon the computer program according to aspect 40 is stored or having stored thereon instructions which, when executed, cause the examination apparatus 1 according to one of the aspects 34 to 39 to execute the steps of the method according to one of the aspects 1 to 33.

| List of reference signs: | |
| --- | --- |
| 1 | Examination apparatus |
| 2 | Paw |
| 3 | Rest surface |
| 4 | Sensor device |
| 5 | Emitter |
| 6 | Detector |
| 7 | Sensor |
| 8 | Limiting device |
| 9 | Emission region |
| 9A | Emission angle |
| 10 | Detection region |
| 10A | Detection angle |
| 11 | Sensor region |
| 12 | Sensing region |
| 13 | Barrier |
| 13A | Transparent area (barrier) |
| 13B | Shielding section |
| 13C | Aperture section |
| 13D | Barrier element |
| 14 | Cover |
| 15 | Electrode |
| 15 | First electrode |
| 15B | Second electrode |
| 15C | Third electrode |
| 16 | Transparent area (electrode) |
| 17 | Circuit board |
| 18 | Scale |
| 18A | Force sensor |
| 19 | Display device |
| 20 | Input device |
| 21 | Power supply device |
| 22 | Interface device |
| 23 | External device |
| 24 | Positioning aid |
| 25 | Control device |
| 26 | Storage medium |
| 27 | Preprocessing device |
| 28 | Common mode suppression device |
| 29 | A/D converter |
| 30 | Preprocessing device |
| 31 | Amplifier |
| 32 | Filter device |
| A | Artery |
| B | Width (examination apparatus) |
| BB | Width (barrier) |
| BF | Blood flow |
| BP | Blood pressure |
| D | Distance (emitter-detector) |
| DB | Distance (barrier-emitter/detector) |
| DE | Distance (electrodes) |
| DM | Distance (extrema) |
| F | Correlation function |
| G | Border |
| HB | Height (Barrier) |
| K | Curve |
| KA | Curve section |
| KG | Cardiogram |
| KM | Curve mean value |
| L | Length |

-continued

| List of reference signs: | |
|---|---|
| M | Curve feature |
| P | Processor |
| P1-P7 | Phase |
| PM1 | Position maximum |
| PM2 | Position minimum |
| PTT | pulse transit time |
| R | Radiation |
| R1-R4 | Row |
| S | Signal |
| S1-S9 | Step |
| T | Animal |
| TH | Time of heartbeat |
| X | Distance |

What is claimed is:

1. A method for blood pressure determination of an animal, comprising:

using a sensor device having a plurality of sensors which form a sensing region for measuring arterial blood flow and transmitting readings of the sensors to a recording device, said plurality of sensors being located in an area larger than that which would be contacted by the animal during said determination and wherein a specific partial region of the sensing region is selected for medical examination, recording a curve comprising information about an arterial blood flow of the animal with the recording device, and automatically cutting the curve into several curve sections in such a way that each curve section corresponds to a heartbeat, the curve sections being produced using different sensors of said plurality of sensors;

recording and using curve sections of curves recorded simultaneously with the different sensors for evaluation in a manner compensating for motion artifacts or errors caused by a movement of the animal during measurement or recording, and determining the blood pressure from readings of the curve sections using a resampling method in which statistical properties of sample statistics are determined based on a repeated drawing of subsamples from an initial sample, wherein the initial sample comprises the plurality of the curve sections and the subsamples are automatically created by selecting curve sections from the initial sample.

2. A method for blood pressure determination of an animal, comprising:

using a sensor device having a plurality of sensors which form a sensing region for measuring arterial blood flow and transmitting readings of the sensors to a recording device, said plurality of sensors being located in an area larger than that which would be contacted by the animal during said determination and wherein a specific partial region of the sensing region is selected for medical examination, recording a curve comprising information about an arterial blood flow of the animal with the recording device, and automatically cutting the curve into several curve sections in such a way that each curve section corresponds to a heartbeat;

determining the blood pressure from the curve sections using a resampling method in which statistical properties of sample statistics are determined on the basis of a repeated drawing of subsamples from an initial sample, wherein the initial sample comprises a plurality of the curve sections and the subsamples are automatically created from selected curve sections from the initial sample.

3. The method according to claim 2, further comprising carrying out an averaging on the basis of the several curve sections for evaluation of the information.

4. The method according to claim 2, wherein a subset of the curve sections is selected for evaluation.

5. The method according to claim 2, wherein a length of the curve sections is determined on the basis of an average heart rate.

6. The method according to claim 2, wherein the resampling method is a bootstrap method.

7. The method according to claim 2, wherein a curve feature is determined from at least one of (a) the curve sections or (b) subsamples, wherein at least one of (a) a curve feature is determined for each subsample or (b) a mean value is determined from several curve features.

8. The method according to claim 7, wherein a measure of dispersion of the curve feature is determined, wherein several curves are recorded and one of the curves is selected for further evaluation on the basis of the measure of dispersion.

9. The method according to claim 7, wherein the blood pressure is determined by means of a correlation function based on the curve feature.

10. The method according to claim 2, wherein a cardiogram is recorded simultaneously with the curve, wherein cutting of the curve into curve sections is performed by means of information from the cardiogram, wherein R peaks of QRS complexes of the cardiogram are used to determine times of heartbeats, wherein the curve is cut into curve sections at the times determined by means of the QRS complexes, wherein at least one of (a) a Pan-Tompkins plot of the cardiogram or (b) an adaptive threshold value are used for determining the R peaks or their positions, wherein the positions of the R peaks determined by means of the Pan-Tompkins plot are subsequently corrected.

11. The method according to claim 2, wherein a cardiogram is recorded simultaneously with the curve, wherein the cardiogram is automatically checked for usefulness, wherein, if the cardiogram is not useful, the cardiogram and the curve are discarded and a new cardiogram and a new curve are recorded.

12. The method according to claim 2, wherein the curve is at least one of (a) automatically or (b) repeatedly checked for usefulness, wherein, if the curve is not useful, the curve or individual curve sections are discarded and a new curve is recorded.

13. The method according to claim 2, wherein a diastolic blood pressure is determined.

14. The method for medical examination of an animal according to claim 1, wherein an arterial blood flow of the animal is optically examined by carrying out a photoplethysmography with said sensor device, wherein the sensor device comprises one or more emitters of the same kind for emitting electromagnetic radiation and several detectors of the same kind for detecting the radiation emitted by the emitter, so that the emitter/emitters and detectors form several sensors of the same kind.

15. The method according to claim 14, wherein the sensors each have a sensor region, the sensor regions of the sensors each being located at different locations and together forming said sensing region, so that with each sensor a different partial region of the sensing region is sensed.

16. The method according to claim 14, wherein the animal is one having paws, and wherein a location of a paw within the sensor region of the sensor is checked, wherein the check comprises analyzing a signal measured with the sensor.

17. The method according to claim 14, wherein the animal is one having paws, and wherein a position of a paw of the animal is determined relative to the sensor device or the sensors.

18. The method according to claim 17, wherein the determined position of the paw is stored and during a recording of at least one curve comprising information about the arterial blood flow with the selected sensor/sensors, it is at least one of (a) automatically, (b) continuously or (c) regularly checked whether the position of the paw has been changed.

19. The method according to claim 18, wherein a new or repeated position determination of sensors takes place when it has been determined that the position of the paw has been changed.

20. The method according to claim 14, wherein several curves comprising information about an arterial blood flow are recorded with the sensors, wherein at least one of the curves is selected for evaluation, wherein a quality of the recorded curves is determined by means of a statistical analysis and the curve with the highest quality is selected for evaluation.

\* \* \* \* \*